(12) United States Patent
Dall'Acqua et al.

(10) Patent No.: US 7,083,784 B2
(45) Date of Patent: Aug. 1, 2006

(54) MOLECULES WITH EXTENDED HALF-LIVES, COMPOSITIONS AND USES THEREOF

(75) Inventors: William Dall'Acqua, Gaithersburg, MD (US); Leslie S. Johnson, Germantown, MD (US); Elizabeth Sally Ward, Dallas, TX (US)

(73) Assignee: MedImmune, Inc., Gaithersburg, MD (US)

(*) Notice: Subject to any disclaimer, the term of this patent is extended or adjusted under 35 U.S.C. 154(b) by 138 days.

(21) Appl. No.: 10/020,354

(22) Filed: Dec. 12, 2001

(65) Prior Publication Data

US 2003/0190311 A1  Oct. 9, 2003

Related U.S. Application Data

(60) Provisional application No. 60/289,760, filed on May 9, 2001, provisional application No. 60/254,884, filed on Dec. 12, 2000.

(51) Int. Cl.
 *C07K 16/00* (2006.01)
 *A61K 39/395* (2006.01)
 *C12P 21/08* (2006.01)
 *C12N 1/00* (2006.01)

(52) U.S. Cl. ............... 424/130.1; 530/387.1; 530/387.7; 530/387.9; 435/810

(58) Field of Classification Search ............ 530/387.1, 530/387.7, 387.9; 424/130.1; 435/810
See application file for complete search history.

(56) References Cited

U.S. PATENT DOCUMENTS

| | | | |
|---|---|---|---|
| 4,703,039 A | 10/1987 | Hawiger et al. | |
| 5,624,821 A | 4/1997 | Winter et al. | |
| 5,648,260 A | 7/1997 | Winter et al. | |
| 5,739,277 A | 4/1998 | Presta et al. | |
| 5,747,035 A | 5/1998 | Presta et al. | |
| 5,824,307 A | 10/1998 | Johnson | |
| 5,869,046 A | 2/1999 | Presta et al. | |
| 6,121,022 A | 9/2000 | Presta et al. | |
| 6,165,745 A | 12/2000 | Ward et al. | |
| 6,194,551 B1 | 2/2001 | Idusogie et al. | |
| 6,277,375 B1 * | 8/2001 | Ward ............... | 424/133.1 |
| 6,528,624 B1 | 3/2003 | Idusogie et al. | |
| 6,538,124 B1 | 3/2003 | Idusogie et al. | |
| 6,572,856 B1 * | 6/2003 | Taylor et al. .......... | 424/130.1 |
| 6,737,056 B1 | 5/2004 | Presta | |
| 2001/0036459 A1 | 11/2001 | Ravetch | |
| 2003/0190311 A1 | 10/2003 | Dall'Acqua et al. | |
| 2004/0002587 A1 | 1/2004 | Watkins et al. | |

FOREIGN PATENT DOCUMENTS

| | | |
|---|---|---|
| EP | 0 368 684 | 5/1990 |
| EP | 0 327 378 | 12/1996 |
| WO | WO 89/07142 | 8/1989 |
| WO | WO 91/14438 | 10/1991 |
| WO | WO 93/22332 | 11/1993 |
| WO | WO 94/29351 | 12/1994 |
| WO | WO 96/32478 | 10/1996 |
| WO | WO 97/34631 | 9/1997 |
| WO | WO 97/43316 | 11/1997 |
| WO | WO 98/23289 | 6/1998 |
| WO | WO 99/43713 | 9/1999 |
| WO | WO 99/51642 | 10/1999 |
| WO | WO 00/09560 | 2/2000 |
| WO | WO 00/42072 | 7/2000 |
| WO | WO 01/58957 | 8/2001 |
| WO | WO 03/054213 | 7/2003 |
| WO | WO 04/016750 | 2/2004 |
| WO | WO 04/029207 | 4/2004 |
| WO | WO 04/035752 | 4/2004 |

OTHER PUBLICATIONS

U.S. Appl. No. 09/724,396, filed Nov. 28, 2000, Young et al.
U.S. Appl. No. 09/724,531, filed Nov. 28, 2000, Young et al.
U.S. Appl. No. 09/996,265, filed Nov. 28, 2001, Young et al.
U.S. Appl. No. 09/996,288, filed Nov. 28, 2001, Young et al.
Borvak et al., 1998, *Intern. Immunol.* 10(9):1289-1298.
Cianga et al., 1999, *Eur. J. Immunol.* 29(8):2515-2523.
Fields et al., 1996, *Immunotechnology* 2(4):270.
Firan et al., 2001, *Intern. Immunol.* 13:993-1002.

(Continued)

*Primary Examiner*—Christina Chan
*Assistant Examiner*—Michail A. Belyavskyi
(74) *Attorney, Agent, or Firm*—Jones Day

(57) ABSTRACT

The present invention provides molecules, including IgGs, non-IgG immunoglobulin, proteins and non-protein agents, that have increased in vivo half-lives due to the presence of an IgG constant domain, or a portion thereof that binds the FcRn, having one or more amino acid modifications that increase the affinity of the constant domain or fragment for FcRn. Such proteins and molecules with increased half-lives have the advantage that smaller amounts and or less frequent dosing is required in the therapeutic, prophylactic or diagnostic use of such molecules.

31 Claims, 11 Drawing Sheets

OTHER PUBLICATIONS

Ghetie et al., 2000, *Annual Rev. Immunol.* 18:739-766.
Ghetie et al., 1996, *Eur. J. Immunol.* 26:690-696.
Ghetie et al., 1997, *Nature Biotech.* 15(7):637-640.
Ho et al., 1989, *Gene* 15:51-59.
Israel et al., 1996, *Immunol.* 89:573-578.
Johnson et al., 1997, *J. Infectious Disease* 176:1215-1224.
Junghans, 1997, *Immunologic Research* 16(1):29-57.
Junghans et al., 1996, *Proc. Natl. Acad. Sci. USA* 93:5512-5516.
Junghans, 1997, *Blood* 90(10):3815-3818.
Junghans, 1997, *Trends in Biotechnology* 5(15):155.
Kabat et al., 1991, Sequences of Proteins of Immunological Interest, U.S. Public Health Service, National Institutes of Health.
Kim et al., 1994, *Scandinavian J. Immunol.* 40(4)457-465.
Kim et al., 1995, *Mol. Immunol.* 32(7):467-475.
Kim et al., 1994, *Eur. J. Immunol.* 24:542-548.
Kim et al., 1994, *Eur. J. Immunol.* 24:2429-2439.
Kim et al., 1994, *FASEB J.* 8:pA467.
Kim et al., 1994, *9th International Congress of Immunol.*, p. 469.
Kunkel et al., 1987, *Methods Enzymol.* 154:367-382.
Li et al., 1997, *J. Mol. Biol.* 269(3):385-394.
Martin and Bjorkman, 1999, *Biochemistry* 38:12639-12647.
Medesan et al., 1996, *Eur. J. Immunol.* 26:2533-2536.
Medesan et al., 1997, *J. Immunol.* 158:2211-2217.
Medesan et al., 1998, *Eur. J. Immunol.* 28(7):2092-2100.
Popov et al., 1996, *Mol. Immunol.* 33:493-502.
Popov et al., 1996, *Mol. Immunol.* 33:521-530.
Sanger et al., 1977, *Proc. Natl. Acad. Sci. USA* 74:5463-5467.
Schuck, et al., 1999, *Mol. Immunol.* 36:1117-1125.
Shields et al., 2001, *J. Biol. Chem.* 276:6591-6604.
Story et al., 1994, *J. Exp. Med.* 180:2377-2381.
Thatte et al., 1999, *J. Exp. Med.* 189(3):509-520.
van der Merwe et al., 1993, *EMBO J.* 12:4945-4594.
van der Merwe et al., 1994, *Biochemistry* 33:10149-10160.
Vaughn and Bjorkman, 1997, *Biochemistry*, 36:9374-9380.
Ward and Qadri, 1997, *Current Opinion Immunol.* 9(1)97-106.
Ward and Ghetie, 1995, *Ther. Immunol.* 2:77-94.
West and Bjorkman, 2000, *Biochemistry* 39:9698-9708.
Ahouse et al. Mouse MHC class I-like Fc receptor encoded outside the MHC. J Immunol. Dec. 1, 1993; 151(11):6076-88.
Burmeister et al. Crystal structure at 2.2 A resolution of the MHC-related neonatal Fc receptor. Nature. Nov. 24, 1994;372(6504):336-43.
Burmeister et al. Crystal structure of the complex of rat neonatal Fc receptor with Fc. Nature. Nov. 24, 1994;372(6504):379-83.
Chintalacharuvu et al. Hybrid IgA2/IgG1 antibodies with tailor-made effector functions. Clin Immunol. Oct. 2001;101(1):21-31.
Cianga et al. Identification and function of neonatal Fc receptor in mammary gland of lactating mice. Eur J Immunol. Aug. 1999;29(8):2515-23.
Dickinson et al. Bidirectional FcRn-dependent IgG transport in a polarized human intestinal epithelial cell line. J Clin Invest. Oct. 1999;104(7):903-11.
Ghetie et al. Multiple roles for the major histocompatibility complex class I—related receptor FcRn. Annu Rev Immunol. 2000;18:739-66. Review.
Kristoffersen et al. Co-localization of the neonatal Fc gamma receptor and IgG in human placental term syncytiotrophoblasts. Eur J Immunol. Jul. 1996;26(7):1668-71.
Martin et al. Characterization of the 2:1 complex between the class I MHC-related Fc receptor and its Fc ligand in solution. Biochemistry. Sep. 28, 1999;38(39):12639-47.
Raghavan et al. Investigation of the interaction between the class I MHC-related Fc receptor and its immunoglobulin G ligand. Immunity. Jul. 1994;1(4):303-15.
Raghavan et al. Analysis of the pH dependence of the neonatal Fc receptor/immunoglobulin G interaction using antibody and receptor variants. Biochemistry. Nov. 14, 1995;34(45):14649-57.
Rodewald R. pH-dependent binding of immunoglobulins to intestinal cells of the neonatal rat. J Cell Biol. Nov. 1976;71(2):666-9.
Sanchez et al. Stoichiometry of the interaction between the major histocompatibility complex-related Fc receptor and its Fc ligand. Biochemistry. Jul. 20, 1999;38(29):9471-6.
Simister et al. An Fc receptor structurally related to MHC class I antigens. Nature. Jan. 12, 1989;337(6203):184-7.
Vaughn et al. High-affinity binding of the neonatal Fc receptor to its IgG ligand requires receptor immobilization. Biochemistry. Aug. 5, 1997;36(31):9374-80.
Vaughn et al. Identification of critical IgG binding epitopes on the neonatal Fc receptor. J Mol Biol. Dec. 12, 1997;274(4):597-607.
Wallace et al. Studies on the immunoglobulin-G Fc-fragment receptor from neonatal rat small intestine. Biochem J. Apr. 15, 1980;188(1):9-16.
Kim et al., 1999, "Mapping the Site on Human IgG for Binding of the MHC Class I-Related Receptor, FcRn," Eur. J. Immunol., 29:2819-2825.

* cited by examiner

```
Glu Pro Lys Ser Cys Asp Lys Thr His Thr Cys Pro Pro Cys Pro Ala
 1           5                   10                  15
|------------------Hinge-----------------------------------|----
Pro Glu Leu Leu Gly Gly Pro Ser Val Phe Leu Phe Pro Pro Lys Pro
             20              25                  30
----------------------------------------------------------------
Lys Asp Thr Leu Met Ile Ser Arg Thr Pro Glu Val Thr Cys Val Val
             35              40                  45
----------------------------------------------------------------
Val Asp Val Ser His Glu Asp Pro Glu Val Lys Phe Asn Trp Tyr Val
     50              55                  60
                                               ----------CH2-----
Asp Gly Val Glu Val His Asn Ala Lys Thr Lys Pro Arg Glu Glu Gln
 65              70                  75                   80
----------------------------------------------------------------
Tyr Asn Ser Thr Tyr Arg Val Val Ser Val Leu Thr Val Leu His Gln
             85                  90                  95
----------------------------------------------------------------
Asp Trp Leu Asn Gly Lys Glu Tyr Lys Cys Lys Val Ser Asn Lys Ala
             100                 105                 110
----------------------------------------------------------------
Leu Pro Ala Pro Ile Glu Lys Thr Ile Ser Lys Ala Lys Gly Gln Pro
             115                 120                 125
--------------------------------------------|-------------------
Arg Glu Pro Gln Val Tyr Thr Leu Pro Pro Ser Arg Glu Glu Met Thr
             130                 135                 140
----------------------------------------------------------------
Lys Asn Gln Val Ser Leu Thr Cys Leu Val Lys Gly Phe Tyr Pro Ser
145              150                 155                 160
                                                      ----CH3-
Asp Ile Ala Val Glu Trp Glu Ser Asn Gly Gln Pro Glu Asn Asn Tyr
             165                 170                 175
----------------------------------------------------------------
Lys Thr Thr Pro Pro Val Leu Asp Ser Asp Gly Ser Phe Phe Leu Tyr
             180                 185                 190
----------------------------------------------------------------
Ser Lys Leu Thr Val Asp Lys Ser Arg Trp Gln Gln Gly Asn Val Phe
             195                 200                 205
----------------------------------------------------------------
Ser Cys Ser Val Met His Glu Ala Leu His Asn His Tyr Thr Gln Lys
             210                 215                 220
----------------------------------------------------------------
Ser Leu Ser Leu Ser Pro Gly Lys
225              230
----------------------------|
```

FIG.2

```
Met Gly Val Pro Arg Pro Gln Pro Trp Ala Leu Gly Leu Leu Leu Phe
 1           5                   10                  15
Leu Leu Pro Gly Ser Leu Gly Ala Glu Ser His Leu Ser Leu Leu Tyr
            20                  25              30
His Leu Thr Ala Val Ser Ser Pro Ala Pro Gly Thr Pro Ala Phe Trp
        35                  40              45
Val Ser Gly Trp Leu Gly Pro Gln Gln Tyr Leu Ser Tyr Asn Ser Leu
    50                  55              60
Arg Gly Glu Ala Glu Pro Cys Gly Ala Trp Val Trp Glu Asn Gln Val
65                  70              75                  80
Ser Trp Tyr Trp Glu Lys Glu Thr Thr Asp Leu Arg Ile Lys Glu Lys
                85                  90                  95
Leu Phe Leu Glu Ala Phe Lys Ala Leu Gly Gly Lys Gly Pro Tyr Thr
            100                 105             110
Leu Gln Gly Leu Leu Gly Cys Glu Leu Gly Pro Asp Asn Thr Ser Val
        115                 120             125
Pro Thr Ala Lys Phe Ala Leu Asn Gly Glu Glu Phe Met Asn Phe Asp
    130                 135             140
Leu Lys Gln Gly Thr Trp Gly Gly Asp Trp Pro Glu Ala Leu Ala Ile
145             150              155                 160
Ser Gln Arg Trp Gln Gln Asp Lys Ala Ala Asn Lys Glu Leu Thr
                165                 170             175
Phe Leu Leu Phe Ser Cys Pro His Arg Leu Arg Glu His Leu Glu Arg
        180                 185             190
Gly Arg Gly Asn Leu Glu Trp Lys Glu Pro Pro Ser Met Atg Leu Lys
        195                 200             205
Ala Arg Pro Ser Ser Pro Gly Phe Ser Val Leu Thr Cys Ser Ala Phe
    210                 215             220
Ser Phe Tyr Pro Pro Glu Leu Gln Leu Arg Phe Leu Arg Asn Gly Leu
225                 230                 235             240
Ala Ala Gly Thr Gly Gln Gly Asp Phe Gly Pro Asn Ser Asp Gly Ser
            245                 250             255
Phe His Ala Ser Ser Ser Leu Thr Val Lys Ser Gly Asp Glu His His
            260                 265             270
Tyr Cys Cys Ile Val Gln His Ala Gly Leu Ala Gln Pro Leu Arg Val
        275                 280             285
Glu Leu Glu Ser Pro Ala Lys Ser Ser Val Leu Val Val Gly Ile Val
        290                 295             300
Ile Gly Val Leu Leu Leu Thr Ala Ala Val Gly Gly Ala Leu Leu
305                 310                 315             320
Trp Arg Arg Met Arg Ser Gly Leu Pro Ala Pro Trp Ile Ser Leu Arg
            325             330                 335
Gly Asp Asp Thr Gly Val Leu Leu Pro Thr Pro Gly Glu Ala Gln Asp
            340                 345             350
Ala Asp Leu Lys Asp Val Asn Val Ile Pro Ala Thr Ala
        355                 360             365
```

FIG.3A

```
Met Gly Met Pro Leu Pro Trp Ala Leu Ser Leu Leu Leu Val Leu Leu
1            5                   10                  15
Pro Gln Thr Trp Gly Ser Glu Thr Arg Pro Pro Leu Met Tyr His Leu
            20                  25              30
Thr Ala Val Ser Asn Pro Ser Thr Gly Leu Pro Ser Phe Trp Ala Thr
            35              40              45
Gly Trp Leu Gly Pro Gln Gln Tyr Leu Thr Tyr Asn Ser Leu Arg Gln
    50                  55              60
Glu Ala Asp Pro Cys Gly Ala Trp Val Trp Glu Asn Gln Val Ser Trp
65              70              75                      80
Tyr Trp Glu Lys Glu Thr Thr Asp Leu Lys Ser Lys Glu Gln Leu Phe
            85                  90              95
Leu Glu Ala Leu Lys Thr Leu Glu Lys Ile Leu Asn Gly Thr Tyr Thr
            100             105             110
Leu Gln Gly Leu Leu Gly Cys Glu Leu Ala Ser Asp Asn Ser Ser Val
        115             120             125
Pro Thr Ala Val Phe Ala Leu Asn Gly Glu Glu Phe Met Lys Phe Asn
    130             135             140
Pro Arg Ile Gly Asn Trp Thr Gly Glu Trp Pro Glu Thr Glu Ile Val
145             150             155                     160
Ala Asn Leu Trp Met Lys Gln Pro Asp Ala Ala Arg Lys Glu Ser Glu
            165             170             175
Phe Leu Leu Asn Ser Cys Pro Glu Arg Leu Leu Gly His Leu Glu Arg
        180             185             190
Gly Arg Arg Asn Leu Glu Trp Lys Glu Pro Pro Ser Met Arg Leu Lys
    195             200             205
Ala Arg Pro Gly Asn Ser Gly Ser Ser Val Leu Thr Cys Ala Ala Phe
    210             215             220
Ser Phe Tyr Pro Pro Glu Leu Lys Phe Arg Phe Leu Arg Asn Gly Leu
225             230             235                     240
Ala Ser Gly Ser Gly Asn Cys Ser Thr Gly Pro Asn Gly Asp Gly Ser
            245             250             255
Phe His Ala Trp Ser Leu Leu Glu Val Lys Arg Gly Asp Glu His His
            260             265             270
Tyr Gln Cys Gln Val Glu His Glu Gly Leu Ala Gln Pro Leu Thr Val
        275             280             285
Asp Leu Asp Ser Ser Ala Arg Ser Ser Val Pro Val Val Gly Ile Val
    290             295             300
Leu Gly Leu Leu Leu Val Val Val Ala Ile Ala Gly Gly Val Leu Leu
305             310             315                     320
Trp Gly Arg Met Arg Ser Gly Leu Pro Ala Pro Trp Leu Ser Leu Ser
            325             330             335
Gly Asp Asp Ser Gly Asp Leu Leu Pro Gly Gly Asn Leu Pro Pro Glu
            340             345             350
Ala Glu Pro Gln Gly Ala Asn Ala Phe Pro Ala Thr Ser
    355             360             365
```

FIG.3B

```
Glu Pro Lys Ser Cys Asp Lys Thr His Thr Cys Pro Pro Cys Pro Ala
1             5                 10                15
············Hinge······································|····
Pro Glu Leu Leu Gly Gly Pro Ser Val Phe Leu Phe Pro Pro Lys Pro
            20              25              30
··················································
Lys Asp Thr Leu Met Ile Ser Arg Thr Pro Glu Val Thr Cys Val Val
        40              45              50
··················································
Val Asp Val Ser His Glu Asp Pro Glu Val Lys Phe Asn Trp Tyr Val
    50              55              60
·············································CH2······
Asp Gly Val Glu Val His Asn Ala Lys Thr Lys Pro Arg Glu Glu Gln
65              70              75              80
··················································
Tyr Asn Ser Thr Tyr Arg Val Val Ser Val Leu Thr Val Leu His Gln
                85              90              95
··················································
Asp Trp Leu Asn Gly Lys Glu Tyr Lys Cys Lys Val Ser Asn Lys Ala
            100             105             110
··················································
Leu Pro Ala Pro Ile Glu Lys Thr Ile Ser Lys Ala Lys Gly Gln Pro
        115             120             125
·······································|··············
Arg Glu Pro Gln Val Tyr Thr Leu Pro Pro Ser Arg Glu Glu Met Thr
    130             135             140
··················································
Lys Asn Gln Val Ser Leu Thr Cys Leu Val Lys Gly Phe Tyr Pro Ser
145             150             155             160
··········································CH3·
Asp Ile Ala Val Glu Trp Glu Ser Asn Gly Gln Pro Glu Asn Asn Tyr
            165             170             175
··  ··············································
Lys Thr Thr Pro Pro Val Leu Asp Ser Asp Gly Ser Phe Phe Leu Tyr
        180             185             190
··················································
Ser Lys Leu Thr Val Asp Lys Ser Arg Trp Gln Gln Gly Asn Val Phe
    195             200             205
··················································
Ser Cys Ser Val Met His Glu Ala Leu His Asn His Tyr Thr Gln Lys
        210             215             220
··················································
Ser Leu Ser Leu Ser Pro Gly Lys
225             230
······························|
```

FIG.4

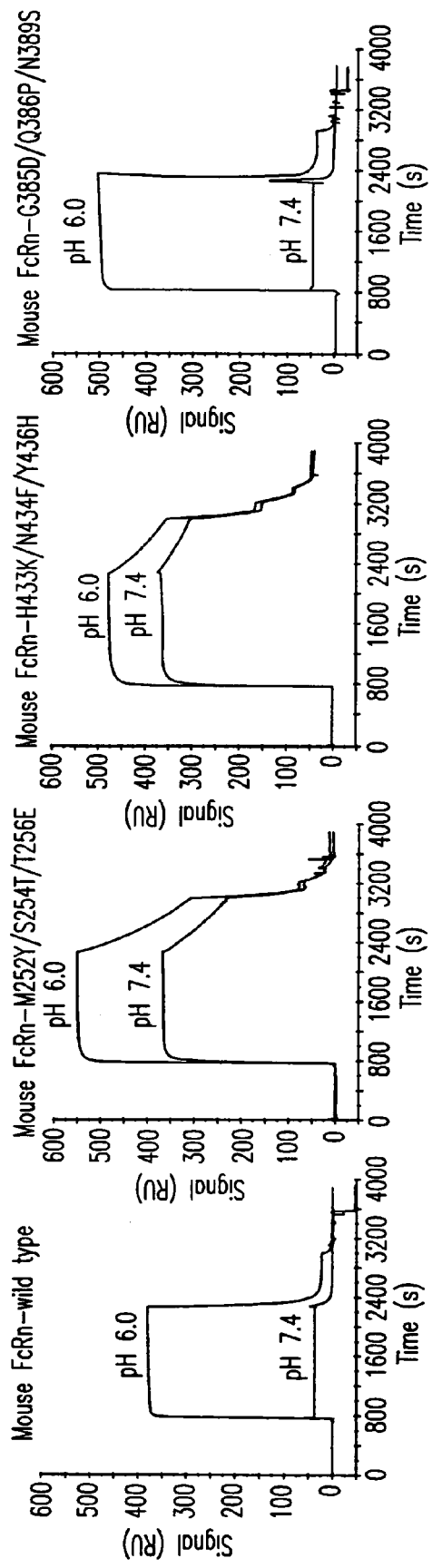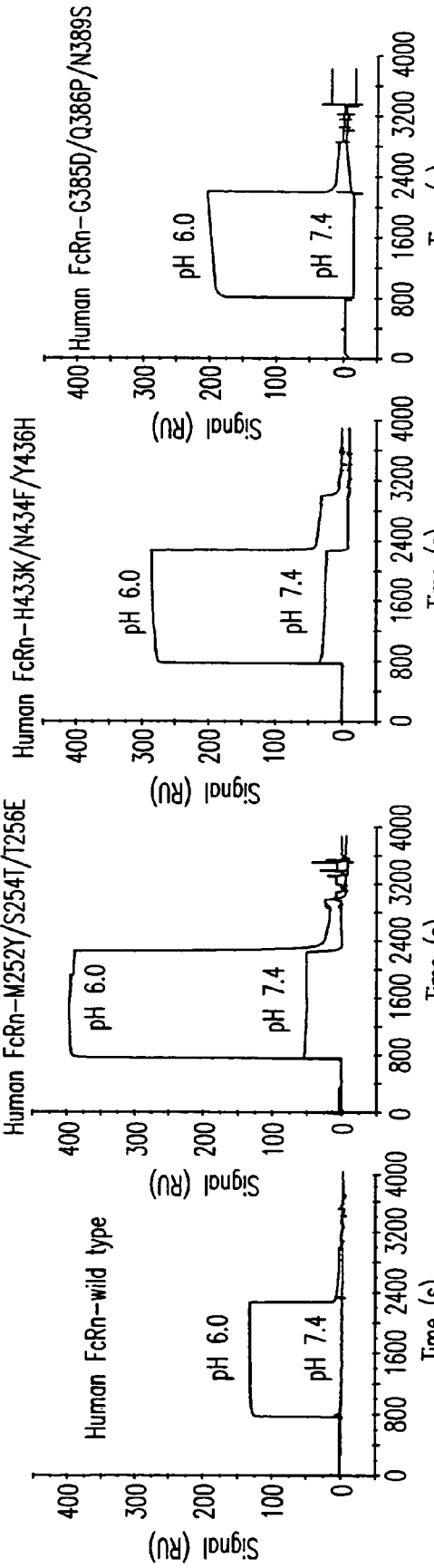

SEQUENCE LISTING

<160> NUMBER OF SEQ ID NOS: 118

<210> SEQ ID NO 1
<211> LENGTH: 7
<212> TYPE: PRT
<213> ORGANISM: Homo sapiens

<400> SEQUENCE: 1

Thr Ser Gly Met Ser Val Gly
1               5

<210> SEQ ID NO 2
<211> LENGTH: 16
<212> TYPE: PRT
<213> ORGANISM: Homo sapiens

<400> SEQUENCE: 2

Asp Ile Trp Trp Asp Asp Lys Lys Asp Tyr Asn Pro Ser Leu Lys Ser
1               5                   10                  15

<210> SEQ ID NO 3
<211> LENGTH: 10
<212> TYPE: PRT
<213> ORGANISM: Homo sapiens

<400> SEQUENCE: 3

Ser Met Ile Thr Asn Trp Tyr Phe Asp Val
1               5                   10

<210> SEQ ID NO 4
<211> LENGTH: 10
<212> TYPE: PRT
<213> ORGANISM: Homo sapiens

<400> SEQUENCE: 4

Lys Cys Gln Leu Ser Val Gly Tyr Met His
1               5                   10

<210> SEQ ID NO 5
<211> LENGTH: 7
<212> TYPE: PRT
<213> ORGANISM: Homo sapiens

<400> SEQUENCE: 5

Asp Thr Ser Lys Leu Ala Ser
1               5

<210> SEQ ID NO 6
<211> LENGTH: 9
<212> TYPE: PRT
<213> ORGANISM: Homo sapiens

<400> SEQUENCE: 6

Phe Gln Gly Ser Gly Tyr Pro Phe Thr
1               5

<210> SEQ ID NO 7
<211> LENGTH: 120
<212> TYPE: PRT
<213> ORGANISM: Homo sapiens

<400> SEQUENCE: 7

Gln Val Thr Leu Arg Glu Ser Gly Pro Ala Leu Val Lys Pro Thr Gln

```
                1               5                   10                  15
Thr Leu Thr Leu Thr Cys Thr Phe Ser Gly Phe Ser Leu Ser Thr Ser
                    20                  25                  30

Gly Met Ser Val Gly Trp Ile Arg Gln Pro Pro Gly Lys Ala Leu Glu
            35                  40                  45

Trp Leu Ala Asp Ile Trp Trp Asp Asp Lys Lys Asp Tyr Asn Pro Ser
        50                  55                  60

Leu Lys Ser Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
                85                  90                  95

Cys Ala Arg Ser Met Ile Thr Asn Trp Tyr Phe Asp Val Trp Gly Ala
                    100                 105                 110

Gly Thr Thr Val Thr Val Ser Ser
                115                 120
```

<210> SEQ ID NO 8
<211> LENGTH: 106
<212> TYPE: PRT
<213> ORGANISM: Homo sapiens
<220> FEATURE:
<221> NAME/KEY: misc_feature
<223> OTHER INFORMATION: VL Domain

<400> SEQUENCE: 8

```
Asp Ile Gln Met Thr Gln Ser Pro Ser Thr Leu Ser Ala Ser Val Gly
1               5                   10                  15

Asp Arg Val Thr Ile Thr Cys Lys Cys Gln Leu Ser Val Gly Tyr Met
                20                  25                  30

His Trp Tyr Gln Gln Lys Pro Gly Lys Ala Pro Lys Leu Leu Ile Tyr
            35                  40                  45

Asp Thr Ser Lys Leu Ala Ser Gly Val Pro Ser Arg Phe Ser Gly Ser
        50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Leu Glu Ile Lys
                100                 105
```

<210> SEQ ID NO 9
<211> LENGTH: 120
<212> TYPE: PRT
<213> ORGANISM: Homo sapiens
<220> FEATURE:
<221> NAME/KEY: misc_feature
<223> OTHER INFORMATION: VH Domain

<400> SEQUENCE: 9

```
Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ala
                20                  25                  30

Gly Met Ser Val Gly Trp Ile Arg Gln Pro Pro Gly Lys Ala Leu Glu
            35                  40                  45

Trp Leu Ala Asp Ile Trp Trp Asp Asp Lys Lys Asp Tyr Asn Pro Ser
        50                  55                  60

Leu Lys Ser Arg Leu Thr Ile Ser Lys Asp Thr Ser Lys Asn Gln Val
```

```
                65                  70                  75                  80
Val Leu Lys Val Thr Asn Met Asp Pro Ala Asp Thr Ala Thr Tyr Tyr
                        85                  90                  95

Cys Ala Arg Ser Met Ile Thr Asn Phe Tyr Phe Asp Val Trp Gly Ala
                100                 105                 110

Gly Thr Thr Val Thr Val Ser Ser
            115                 120

<210> SEQ ID NO 10
<211> LENGTH: 7
<212> TYPE: PRT
<213> ORGANISM: Homo sapiens

<400> SEQUENCE: 10

Thr Ala Gly Met Ser Val Gly
1               5

<210> SEQ ID NO 11
<211> LENGTH: 106
<212> TYPE: PRT
<213> ORGANISM: Homo sapiens

<400> SEQUENCE: 11

Asp Ile Gln Met Thr Gln Ser Pro Ser Thr Leu Ser Ala Ser Val Gly
1               5                   10                  15

Asp Arg Val Thr Ile Thr Cys Ser Ala Ser Ser Arg Val Gly Tyr Met
            20                  25                  30

His Trp Tyr Gln Gln Lys Pro Gly Lys Ala Pro Lys Leu Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Leu Glu Ile Lys
            100                 105

<210> SEQ ID NO 12
<211> LENGTH: 10
<212> TYPE: PRT
<213> ORGANISM: Homo sapiens

<400> SEQUENCE: 12

Ser Met Ile Thr Asn Phe Tyr Phe Asp Val
1               5                   10

<210> SEQ ID NO 13
<211> LENGTH: 106
<212> TYPE: PRT
<213> ORGANISM: Homo sapiens

<400> SEQUENCE: 13

Asp Ile Gln Met Thr Gln Ser Pro Ser Thr Leu Ser Ala Ser Val Gly
1               5                   10                  15

Asp Arg Val Thr Ile Thr Cys Ser Ala Ser Ser Val Gly Tyr Met
            20                  25                  30

His Trp Tyr Gln Gln Lys Pro Gly Lys Ala Pro Lys Leu Leu Ile Tyr
        35                  40                  45
```

-continued

Asp Thr Phe Lys Leu Ala Ser Gly Val Pro Ser Arg Phe Ser Gly Ser
          50                  55                  60

Gly Ser Gly Thr Glu Phe Thr Leu Thr Ile Ser Ser Leu Gln Pro Asp
 65                  70                  75                  80

Asp Phe Ala Thr Tyr Tyr Cys Phe Gln Phe Ser Gly Tyr Pro Phe Thr
                 85                  90                  95

Phe Gly Gly Gly Thr Lys Leu Glu Ile Lys
            100                 105

<210> SEQ ID NO 14
<211> LENGTH: 10
<212> TYPE: PRT
<213> ORGANISM: Homo sapiens

<400> SEQUENCE: 14

Ser Ala Ser Ser Ser Val Gly Tyr Met His
1               5                   10

<210> SEQ ID NO 15
<211> LENGTH: 7
<212> TYPE: PRT
<213> ORGANISM: Homo sapiens

<400> SEQUENCE: 15

Asp Thr Phe Lys Leu Ala Ser
1               5

<210> SEQ ID NO 16
<211> LENGTH: 9
<212> TYPE: PRT
<213> ORGANISM: Homo sapiens

<400> SEQUENCE: 16

Phe Gln Phe Ser Gly Tyr Pro Phe Thr
1               5

<210> SEQ ID NO 17
<211> LENGTH: 120
<212> TYPE: PRT
<213> ORGANISM: Homo sapiens

<400> SEQUENCE: 17

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Pro
             20                  25                  30

Gly Met Ser Val Gly Trp Ile Arg Gln Pro Pro Gly Lys Ala Leu Glu
         35                  40                  45

Trp Leu Ala Asp Ile Trp Trp Asp Asp Lys Lys His Tyr Asn Pro Ser
 50                  55                  60

Leu Lys Asp Arg Leu Thr Ile Ser Lys Asp Thr Ser Lys Asn Gln Val
 65                  70                  75                  80

Val Leu Lys Val Thr Asn Met Asp Pro Ala Asp Thr Ala Thr Tyr Tyr
                 85                  90                  95

Cys Ala Arg Asp Met Ile Phe Asn Phe Tyr Phe Asp Val Trp Gly Ala
            100                 105                 110

Gly Thr Thr Val Thr Val Ser Ser
         115                 120

<210> SEQ ID NO 18

```
<211> LENGTH: 7
<212> TYPE: PRT
<213> ORGANISM: Homo sapiens

<400> SEQUENCE: 18

Thr Pro Gly Met Ser Val Gly
1               5

<210> SEQ ID NO 19
<211> LENGTH: 16
<212> TYPE: PRT
<213> ORGANISM: Homo sapiens

<400> SEQUENCE: 19

Asp Ile Trp Trp Asp Asp Lys Lys His Tyr Asn Pro Ser Leu Lys Asp
1               5                   10                  15

<210> SEQ ID NO 20
<211> LENGTH: 10
<212> TYPE: PRT
<213> ORGANISM: Homo sapiens

<400> SEQUENCE: 20

Asp Met Ile Phe Asn Phe Tyr Phe Asp Val
1               5                   10

<210> SEQ ID NO 21
<211> LENGTH: 106
<212> TYPE: PRT
<213> ORGANISM: Homo sapiens
<220> FEATURE:
<221> NAME/KEY: misc_feature
<223> OTHER INFORMATION: VL Domain

<400> SEQUENCE: 21

Asp Ile Gln Met Thr Gln Ser Pro Ser Thr Leu Ser Ala Ser Val Gly
1               5                   10                  15

Asp Arg Val Thr Ile Thr Cys Ser Leu Ser Ser Arg Val Gly Tyr Met
            20                  25                  30

His Trp Tyr Gln Gln Lys Pro Gly Lys Ala Pro Lys Leu Leu Ile Tyr
        35                  40                  45

Asp Thr Phe Tyr Leu Ser Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Val Glu Ile Lys
            100                 105

<210> SEQ ID NO 22
<211> LENGTH: 10
<212> TYPE: PRT
<213> ORGANISM: Homo sapiens

<400> SEQUENCE: 22

Ser Leu Ser Ser Arg Val Gly Tyr Met His
1               5                   10

<210> SEQ ID NO 23
<211> LENGTH: 7
<212> TYPE: PRT
<213> ORGANISM: Homo sapiens
```

```
<400> SEQUENCE: 23

Asp Thr Phe Tyr Leu Ser Ser
1               5

<210> SEQ ID NO 24
<211> LENGTH: 120
<212> TYPE: PRT
<213> ORGANISM: Homo sapiens
<220> FEATURE:
<221> NAME/KEY: misc_feature
<223> OTHER INFORMATION: VH Domain

<400> SEQUENCE: 24

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Pro
            20                  25                  30

Gly Met Ser Val Gly Trp Ile Arg Gln Pro Pro Gly Lys Ala Leu Glu
        35                  40                  45

Trp Leu Ala Asp Ile Trp Trp Asp Gly Lys Lys His Tyr Asn Pro Ser
    50                  55                  60

Leu Lys Asp Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
                85                  90                  95

Cys Ala Arg Asp Met Ile Phe Asn Phe Tyr Phe Asp Val Trp Gly Gln
            100                 105                 110

Gly Thr Thr Val Thr Val Ser Ser
        115                 120

<210> SEQ ID NO 25
<211> LENGTH: 16
<212> TYPE: PRT
<213> ORGANISM: Homo sapiens

<400> SEQUENCE: 25

Asp Ile Trp Trp Asp Gly Lys Lys His Tyr Asn Pro Ser Leu Lys Asp
1               5                   10                  15

<210> SEQ ID NO 26
<211> LENGTH: 106
<212> TYPE: PRT
<213> ORGANISM: Homo sapiens

<400> SEQUENCE: 26

Asp Ile Gln Met Thr Gln Ser Pro Ser Thr Leu Ser Ala Ser Val Gly
1               5                   10                  15

Asp Arg Val Thr Ile Thr Cys Ser Leu Ser Ser Arg Val Gly Tyr Met
            20                  25                  30

His Trp Tyr Gln Gln Lys Pro Gly Lys Ala Pro Lys Leu Leu Ile Tyr
        35                  40                  45

Asp Thr Arg Gly Leu Pro Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Val Glu Ile Lys
```

-continued

```
                100                 105

<210> SEQ ID NO 27
<211> LENGTH: 7
<212> TYPE: PRT
<213> ORGANISM: Homo sapiens

<400> SEQUENCE: 27

Asp Thr Arg Gly Leu Pro Ser
1               5

<210> SEQ ID NO 28
<211> LENGTH: 120
<212> TYPE: PRT
<213> ORGANISM: Homo sapiens

<400> SEQUENCE: 28

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Pro
            20                  25                  30

Gly Met Ser Val Gly Trp Ile Arg Gln Pro Pro Gly Lys Ala Leu Glu
        35                  40                  45

Trp Leu Ala Asp Ile Trp Trp Asp Gly Lys Lys His Tyr Asn Pro Ser
    50                  55                  60

Leu Lys Asp Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
                85                  90                  95

Cys Ala Arg Asp Met Ile Phe Asn Trp Tyr Phe Asp Val Trp Gly Gln
            100                 105                 110

Gly Thr Thr Val Thr Val Ser Ser
        115                 120

<210> SEQ ID NO 29
<211> LENGTH: 10
<212> TYPE: PRT
<213> ORGANISM: Homo sapiens

<400> SEQUENCE: 29

Asp Met Ile Phe Asn Trp Tyr Phe Asp Val
1               5                   10

<210> SEQ ID NO 30
<211> LENGTH: 106
<212> TYPE: PRT
<213> ORGANISM: Homo sapiens

<400> SEQUENCE: 30

Asp Ile Gln Met Thr Gln Ser Pro Ser Thr Leu Ser Ala Ser Val Gly
1               5                   10                  15

Asp Arg Val Thr Ile Thr Cys Ser Pro Ser Ser Arg Val Gly Tyr Met
            20                  25                  30

His Trp Tyr Gln Gln Lys Pro Gly Lys Ala Pro Lys Leu Leu Ile Tyr
        35                  40                  45

Asp Thr Met Arg Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80
```

```
Asp Phe Ala Thr Tyr Tyr Cys Phe Gln Gly Ser Gly Tyr Pro Phe Thr
                85                  90                  95

Phe Gly Gly Gly Thr Lys Val Glu Ile Lys
            100                 105

<210> SEQ ID NO 31
<211> LENGTH: 10
<212> TYPE: PRT
<213> ORGANISM: Homo sapiens

<400> SEQUENCE: 31

Ser Pro Ser Ser Arg Val Gly Tyr Met His
1               5                   10

<210> SEQ ID NO 32
<211> LENGTH: 7
<212> TYPE: PRT
<213> ORGANISM: Homo sapiens

<400> SEQUENCE: 32

Asp Thr Met Arg Leu Ala Ser
1               5

<210> SEQ ID NO 33
<211> LENGTH: 120
<212> TYPE: PRT
<213> ORGANISM: Homo sapiens

<400> SEQUENCE: 33

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Pro
            20                  25                  30

Gly Met Ser Val Gly Trp Ile Arg Gln Pro Pro Gly Lys Ala Leu Glu
        35                  40                  45

Trp Leu Ala Asp Ile Trp Trp Asp Gly Lys Lys His Tyr Asn Pro Ser
    50                  55                  60

Leu Lys Asp Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
                85                  90                  95

Cys Ala Arg Asp Met Ile Phe Asn Trp Tyr Phe Asp Val Trp Gly Gln
            100                 105                 110

Gly Thr Thr Val Thr Val Ser Ser
        115                 120

<210> SEQ ID NO 34
<211> LENGTH: 106
<212> TYPE: PRT
<213> ORGANISM: Homo sapiens

<400> SEQUENCE: 34

Asp Ile Gln Met Thr Gln Ser Pro Ser Thr Leu Ser Ala Ser Val Gly
1               5                   10                  15

Asp Arg Val Thr Ile Thr Cys Ser Leu Ser Ser Arg Val Gly Tyr Met
            20                  25                  30

His Trp Tyr Gln Gln Lys Pro Gly Lys Ala Pro Lys Leu Leu Ile Tyr
        35                  40                  45

Asp Thr Phe Lys Leu Ser Ser Gly Val Pro Ser Arg Phe Ser Gly Ser
    50                  55                  60
```

```
Gly Ser Gly Thr Glu Phe Thr Leu Thr Ile Ser Ser Leu Gln Pro Asp
 65                  70                  75                  80

Asp Phe Ala Thr Tyr Tyr Cys Phe Gln Gly Ser Gly Tyr Pro Phe Thr
                 85                  90                  95

Phe Gly Gly Gly Thr Lys Val Glu Ile Lys
            100                 105

<210> SEQ ID NO 35
<211> LENGTH: 7
<212> TYPE: PRT
<213> ORGANISM: Homo sapiens

<400> SEQUENCE: 35

Asp Thr Phe Lys Leu Ser Ser
 1               5

<210> SEQ ID NO 36
<211> LENGTH: 120
<212> TYPE: PRT
<213> ORGANISM: Homo sapiens

<400> SEQUENCE: 36

Gln Val Thr Leu Arg Glu Ser Gly Pro Ala Leu Val Lys Pro Thr Gln
 1               5                  10                  15

Thr Leu Thr Leu Thr Cys Thr Phe Ser Gly Phe Ser Leu Ser Thr Ala
                 20                  25                  30

Gly Met Ser Val Gly Trp Ile Arg Gln Pro Pro Gly Lys Ala Leu Glu
             35                  40                  45

Trp Leu Ala Asp Ile Trp Trp Asp Gly Lys Lys Asp Tyr Asn Pro Ser
 50                  55                  60

Leu Lys Asp Arg Leu Thr Ile Ser Lys Asp Thr Ser Lys Asn Gln Val
 65                  70                  75                  80

Val Leu Lys Val Thr Asn Met Asp Pro Ala Asp Thr Ala Thr Tyr Tyr
                 85                  90                  95

Cys Ala Arg Asp Met Ile Phe Asn Phe Tyr Phe Asp Val Trp Gly Gln
            100                 105                 110

Gly Thr Thr Val Thr Val Ser Ser
            115                 120

<210> SEQ ID NO 37
<211> LENGTH: 16
<212> TYPE: PRT
<213> ORGANISM: Homo sapiens

<400> SEQUENCE: 37

Asp Ile Trp Trp Asp Gly Lys Lys Asp Tyr Asn Pro Ser Leu Lys Asp
 1               5                  10                  15

<210> SEQ ID NO 38
<211> LENGTH: 106
<212> TYPE: PRT
<213> ORGANISM: Homo sapiens

<400> SEQUENCE: 38

Asp Ile Gln Met Thr Gln Ser Pro Ser Thr Leu Ser Ala Ser Val Gly
 1               5                  10                  15

Asp Arg Val Thr Ile Thr Cys Ser Ala Ser Ser Arg Val Gly Tyr Met
                 20                  25                  30

His Trp Tyr Gln Gln Lys Pro Gly Lys Ala Pro Lys Leu Leu Ile Tyr
```

-continued

```
                35                  40                  45
Asp Thr Phe Lys Leu Ser Ser Gly Val Pro Ser Arg Phe Ser Gly Ser
                50                  55                  60
Gly Ser Gly Thr Glu Phe Thr Leu Thr Ile Ser Ser Leu Gln Pro Asp
 65                  70                  75                  80
Asp Phe Ala Thr Tyr Tyr Cys Phe Gln Gly Ser Gly Tyr Pro Phe Thr
                 85                  90                  95
Phe Gly Gly Gly Thr Lys Val Glu Ile Lys
            100                 105
```

<210> SEQ ID NO 39
<211> LENGTH: 10
<212> TYPE: PRT
<213> ORGANISM: Homo sapiens

<400> SEQUENCE: 39

```
Ser Ala Ser Ser Arg Val Gly Tyr Met His
 1               5                  10
```

<210> SEQ ID NO 40
<211> LENGTH: 120
<212> TYPE: PRT
<213> ORGANISM: Homo sapiens

<400> SEQUENCE: 40

```
Gln Val Thr Leu Arg Glu Ser Gly Pro Ala Leu Val Lys Pro Thr Gln
 1               5                  10                  15
Thr Leu Thr Leu Thr Cys Thr Phe Ser Gly Phe Ser Leu Ser Thr Ala
                20                  25                  30
Gly Met Ser Val Gly Trp Ile Arg Gln Pro Pro Gly Lys Ala Leu Glu
            35                  40                  45
Trp Leu Ala Asp Ile Trp Trp Asp Gly Lys Lys Ser Tyr Asn Pro Ser
        50                  55                  60
Leu Lys Asp Arg Leu Thr Ile Ser Lys Asp Thr Ser Lys Asn Gln Val
 65                  70                  75                  80
Val Leu Lys Val Thr Asn Met Asp Pro Ala Asp Thr Ala Thr Tyr Tyr
                 85                  90                  95
Cys Ala Arg Asp Met Ile Phe Asn Phe Tyr Phe Asp Val Trp Gly Gln
            100                 105                 110
Gly Thr Thr Val Thr Val Ser Ser
            115                 120
```

<210> SEQ ID NO 41
<211> LENGTH: 16
<212> TYPE: PRT
<213> ORGANISM: Homo sapiens

<400> SEQUENCE: 41

```
Asp Ile Trp Trp Asp Gly Lys Lys Ser Tyr Asn Pro Ser Leu Lys Asp
 1               5                  10                  15
```

<210> SEQ ID NO 42
<211> LENGTH: 106
<212> TYPE: PRT
<213> ORGANISM: Homo sapiens

<400> SEQUENCE: 42

```
Asp Ile Gln Met Thr Gln Ser Pro Ser Thr Leu Ser Ala Ser Val Gly
 1               5                  10                  15
```

```
Asp Arg Val Thr Ile Thr Cys Ser Leu Ser Ser Arg Val Gly Tyr Met
            20                  25                  30

His Trp Tyr Gln Gln Lys Pro Gly Lys Ala Pro Lys Leu Leu Ile Tyr
        35                  40                  45

Asp Thr Met Tyr Gln Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Val Glu Ile Lys
            100                 105
```

<210> SEQ ID NO 43
<211> LENGTH: 7
<212> TYPE: PRT
<213> ORGANISM: Homo sapiens

<400> SEQUENCE: 43

```
Asp Thr Met Tyr Gln Ser Ser
1               5
```

<210> SEQ ID NO 44
<211> LENGTH: 120
<212> TYPE: PRT
<213> ORGANISM: Homo sapiens

<400> SEQUENCE: 44

```
Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ala
            20                  25                  30

Gly Met Ser Val Gly Trp Ile Arg Gln Pro Pro Gly Lys Ala Leu Glu
        35                  40                  45

Trp Leu Ala Asp Ile Trp Trp Asp Gly Lys Lys Ser Tyr Asn Pro Ser
    50                  55                  60

Leu Lys Asp Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
                85                  90                  95

Cys Ala Arg Asp Met Ile Phe Asn Phe Tyr Phe Asp Val Trp Gly Gln
            100                 105                 110

Gly Thr Thr Val Thr Val Ser Ser
        115                 120
```

<210> SEQ ID NO 45
<211> LENGTH: 16
<212> TYPE: PRT
<213> ORGANISM: Homo sapiens

<400> SEQUENCE: 45

```
Asp Ile Trp Trp Asp Asp Lys Lys Ser Tyr Asn Pro Ser Leu Lys Asp
1               5                   10                  15
```

<210> SEQ ID NO 46
<211> LENGTH: 106
<212> TYPE: PRT
<213> ORGANISM: Homo sapiens

<400> SEQUENCE: 46

-continued

```
Asp Ile Gln Met Thr Gln Ser Pro Ser Thr Leu Ser Ala Ser Val Gly
1               5                   10                  15

Asp Arg Val Thr Ile Thr Cys Leu Pro Ser Ser Arg Val Gly Tyr Met
            20                  25                  30

His Trp Tyr Gln Gln Lys Pro Gly Lys Ala Pro Lys Leu Leu Ile Tyr
        35                  40                  45

Asp Thr Met Tyr Gln Ala Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Phe Ser Gly Tyr Pro Phe Thr
                85                  90                  95

Phe Gly Gly Gly Thr Lys Leu Glu Ile Lys
            100                 105

<210> SEQ ID NO 47
<211> LENGTH: 10
<212> TYPE: PRT
<213> ORGANISM: Homo sapiens

<400> SEQUENCE: 47

Leu Pro Ser Ser Arg Val Gly Tyr Met His
1               5                   10

<210> SEQ ID NO 48
<211> LENGTH: 120
<212> TYPE: PRT
<213> ORGANISM: Homo sapiens

<400> SEQUENCE: 48

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ala
            20                  25                  30

Gly Met Ser Val Gly Trp Ile Arg Gln Pro Pro Gly Lys Ala Leu Glu
        35                  40                  45

Trp Leu Ala Asp Ile Trp Trp Asp Asp Lys Lys His Tyr Asn Pro Ser
    50                  55                  60

Leu Lys Asp Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
                85                  90                  95

Cys Ala Arg Asp Met Ile Phe Asn Phe Tyr Phe Asp Val Trp Gly Gln
            100                 105                 110

Gly Thr Thr Val Thr Val Ser Ser
        115                 120

<210> SEQ ID NO 49
<211> LENGTH: 106
<212> TYPE: PRT
<213> ORGANISM: Homo sapiens

<400> SEQUENCE: 49

Asp Ile Gln Met Thr Gln Ser Pro Ser Thr Leu Ser Ala Ser Val Gly
1               5                   10                  15

Asp Arg Val Thr Ile Thr Cys Ser Ala Ser Ser Arg Val Gly Tyr Met
            20                  25                  30
```

His Trp Tyr Gln Gln Lys Pro Gly Lys Ala Pro Lys Leu Leu Ile Tyr
         35                  40                  45

Asp Thr Phe Phe Leu Asp Ser Gly Val Pro Ser Arg Phe Ser Gly Ser
         50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                 85                  90                  95

Phe Gly Gly Gly Thr Lys Leu Glu Ile Lys
             100                 105

<210> SEQ ID NO 50
<211> LENGTH: 7
<212> TYPE: PRT
<213> ORGANISM: Homo sapiens

<400> SEQUENCE: 50

Asp Thr Phe Phe Leu Asp Ser
1               5

<210> SEQ ID NO 51
<211> LENGTH: 120
<212> TYPE: PRT
<213> ORGANISM: Homo sapiens

<400> SEQUENCE: 51

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ala
             20                  25                  30

Gly Met Ser Val Gly Trp Ile Arg Gln Pro Pro Gly Lys Ala Leu Glu
         35                  40                  45

Trp Leu Ala Asp Ile Trp Trp Asp Asp Lys Ser Tyr Asn Pro Ser
     50                  55                  60

Leu Lys Asp Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
                 85                  90                  95

Cys Ala Arg Asp Met Ile Phe Asn Trp Tyr Phe Asp Val Trp Gly Gln
             100                 105                 110

Gly Thr Thr Val Thr Val Ser Ser
         115                 120

<210> SEQ ID NO 52
<211> LENGTH: 106
<212> TYPE: PRT
<213> ORGANISM: Homo sapiens

<400> SEQUENCE: 52

Asp Ile Gln Met Thr Gln Ser Pro Ser Thr Leu Ser Ala Ser Val Gly
1               5                   10                  15

Asp Arg Val Thr Ile Thr Cys Ser Ala Ser Ser Arg Val Gly Tyr Met
             20                  25                  30

His Trp Tyr Gln Gln Lys Pro Gly Lys Ala Pro Lys Leu Leu Ile Tyr
         35                  40                  45

Asp Thr Arg Tyr Gln Ser Ser Gly Val Pro Ser Arg Phe Ser Gly Ser
     50                  55                  60

Gly Ser Gly Thr Glu Phe Thr Leu Thr Ile Ser Ser Leu Gln Pro Asp

```
                   65                  70                  75                  80
Asp Phe Ala Thr Tyr Tyr Cys Phe Gln Gly Ser Gly Tyr Pro Phe Thr
                    85                  90                  95

Phe Gly Gly Gly Thr Lys Leu Glu Ile Lys
                100                 105

<210> SEQ ID NO 53
<211> LENGTH: 7
<212> TYPE: PRT
<213> ORGANISM: Homo sapiens

<400> SEQUENCE: 53

Asp Thr Arg Tyr Gln Ser Ser
1               5

<210> SEQ ID NO 54
<211> LENGTH: 106
<212> TYPE: PRT
<213> ORGANISM: Homo sapiens
<220> FEATURE:
<221> NAME/KEY: misc_feature
<223> OTHER INFORMATION: VL Domain

<400> SEQUENCE: 54

Asp Ile Gln Met Thr Gln Ser Pro Ser Thr Leu Ser Ala Ser Val Gly
1               5                  10                  15

Asp Arg Val Thr Ile Thr Cys Ser Ala Ser Ser Ser Val Gly Tyr Met
                20                  25                  30

His Trp Tyr Gln Gln Lys Pro Gly Lys Ala Pro Lys Leu Leu Ile Tyr
            35                  40                  45

Asp Thr Ser Lys Leu Ala Ser Gly Val Pro Ser Arg Phe Ser Gly Ser
        50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                    85                  90                  95

Phe Gly Gly Gly Thr Lys Leu Glu Ile Lys
                100                 105

<210> SEQ ID NO 55
<211> LENGTH: 120
<212> TYPE: PRT
<213> ORGANISM: Homo sapiens

<400> SEQUENCE: 55

Gln Val Thr Leu Arg Glu Ser Gly Pro Ala Leu Val Lys Pro Thr Gln
1               5                  10                  15

Thr Leu Thr Leu Thr Cys Thr Phe Ser Gly Phe Ser Leu Ser Thr Ala
                20                  25                  30

Gly Met Ser Val Gly Trp Ile Arg Gln Pro Pro Gly Lys Ala Leu Glu
            35                  40                  45

Trp Leu Ala Asp Ile Trp Trp Asp Asp Lys Lys Asp Tyr Asn Pro Ser
        50                  55                  60

Leu Lys Ser Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
                    85                  90                  95

Cys Ala Arg Asp Met Ile Phe Asn Trp Tyr Phe Asp Val Trp Gly Ala
                100                 105                 110
```

Gly Thr Thr Val Thr Val Ser Ser
        115                 120

<210> SEQ ID NO 56
<211> LENGTH: 106
<212> TYPE: PRT
<213> ORGANISM: Homo sapiens
<220> FEATURE:
<221> NAME/KEY: misc_feature
<223> OTHER INFORMATION: VL Domain

<400> SEQUENCE: 56

Asp Ile Gln Met Thr Gln Ser Pro Ser Thr Leu Ser Ala Ser Val Gly
1               5                   10                  15

Asp Arg Val Thr Ile Thr Cys Ser Ala Ser Ser Val Gly Tyr Met
            20                  25                  30

His Trp Tyr Gln Gln Lys Pro Gly Lys Ala Pro Lys Leu Leu Ile Tyr
        35                  40                  45

Asp Thr Phe Lys Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Leu Glu Ile Lys
            100                 105

<210> SEQ ID NO 57
<211> LENGTH: 106
<212> TYPE: PRT
<213> ORGANISM: Homo sapiens
<220> FEATURE:
<221> NAME/KEY: misc_feature
<223> OTHER INFORMATION: VL Domain

<400> SEQUENCE: 57

Asp Ile Gln Met Thr Gln Ser Pro Ser Thr Leu Ser Ala Ser Val Gly
1               5                   10                  15

Asp Arg Val Thr Ile Thr Cys Ser Ala Ser Ser Val Gly Tyr Met
            20                  25                  30

His Trp Tyr Gln Gln Lys Pro Gly Lys Ala Pro Lys Leu Leu Ile Tyr
        35                  40                  45

Asp Thr Tyr Lys Gln Thr Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Leu Glu Ile Lys
            100                 105

<210> SEQ ID NO 58
<211> LENGTH: 7
<212> TYPE: PRT
<213> ORGANISM: Homo sapiens

<400> SEQUENCE: 58

Asp Thr Tyr Lys Gln Thr Ser
1               5

```
<210> SEQ ID NO 59
<211> LENGTH: 106
<212> TYPE: PRT
<213> ORGANISM: Homo sapiens
<220> FEATURE:
<221> NAME/KEY: misc_feature
<223> OTHER INFORMATION: VL Domain

<400> SEQUENCE: 59

Asp Ile Gln Met Thr Gln Ser Pro Ser Thr Leu Ser Ala Ser Val Gly
 1               5                  10                  15

Asp Arg Val Thr Ile Thr Cys Ser Ala Ser Ser Val Gly Tyr Met
             20                  25                  30

His Trp Tyr Gln Gln Lys Pro Gly Lys Ala Pro Lys Leu Leu Ile Tyr
             35                  40                  45

Asp Thr Arg Tyr Leu Ser Ser Gly Val Pro Ser Arg Phe Ser Gly Ser
         50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                 85                  90                  95

Phe Gly Gly Gly Thr Lys Leu Glu Ile Lys
                100                 105

<210> SEQ ID NO 60
<211> LENGTH: 106
<212> TYPE: PRT
<213> ORGANISM: Homo sapiens

<400> SEQUENCE: 60

Asp Ile Gln Met Thr Gln Ser Pro Ser Thr Leu Ser Ala Ser Val Gly
 1               5                  10                  15

Asp Arg Val Thr Ile Thr Cys Ser Ala Ser Ser Val Gly Tyr Met
             20                  25                  30

His Trp Tyr Gln Gln Lys Pro Gly Lys Ala Pro Lys Leu Leu Ile Tyr
             35                  40                  45

Asp Thr Phe Lys Leu Ala Ser Gly Val Pro Ser Arg Phe Ser Gly Ser
         50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Phe Tyr Pro Phe Thr
                 85                  90                  95

Phe Gly Gly Gly Thr Lys Leu Glu Ile Lys
                100                 105

<210> SEQ ID NO 61
<211> LENGTH: 9
<212> TYPE: PRT
<213> ORGANISM: Homo sapiens

<400> SEQUENCE: 61

Phe Gln Gly Ser Phe Tyr Pro Phe Thr
 1               5

<210> SEQ ID NO 62
<211> LENGTH: 106
<212> TYPE: PRT
<213> ORGANISM: Homo sapiens
<220> FEATURE:
<221> NAME/KEY: misc_feature
```

<223> OTHER INFORMATION: VL Domain

<400> SEQUENCE: 62

Asp Ile Gln Met Thr Gln Ser Pro Ser Thr Leu Ser Ala Ser Val Gly
1               5                   10                  15

Asp Arg Val Thr Ile Thr Cys Ser Ala Ser Ser Val Gly Tyr Met
            20                  25                  30

His Trp Tyr Gln Gln Lys Pro Gly Lys Ala Pro Lys Leu Leu Ile Tyr
            35                  40                  45

Asp Thr Phe Lys Leu Thr Ser Gly Val Pro Ser Arg Phe Ser Gly Ser
        50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Leu Glu Ile Lys
                100                 105

<210> SEQ ID NO 63
<211> LENGTH: 7
<212> TYPE: PRT
<213> ORGANISM: Homo sapiens

<400> SEQUENCE: 63

Asp Thr Phe Lys Leu Thr Ser
1               5

<210> SEQ ID NO 64
<211> LENGTH: 106
<212> TYPE: PRT
<213> ORGANISM: Homo sapiens
<220> FEATURE:
<221> NAME/KEY: misc_feature
<223> OTHER INFORMATION: VL Domain

<400> SEQUENCE: 64

Asp Ile Gln Met Thr Gln Ser Pro Ser Thr Leu Ser Ala Ser Val Gly
1               5                   10                  15

Asp Arg Val Thr Ile Thr Cys Ser Ala Ser Ser Val Gly Tyr Met
            20                  25                  30

His Trp Tyr Gln Gln Lys Pro Gly Lys Ala Pro Lys Leu Leu Ile Tyr
            35                  40                  45

Asp Thr Phe Arg Leu Ala Ser Gly Val Pro Ser Arg Phe Ser Gly Ser
        50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Leu Glu Ile Lys
                100                 105

<210> SEQ ID NO 65
<211> LENGTH: 106
<212> TYPE: PRT
<213> ORGANISM: Homo sapiens

<400> SEQUENCE: 65

Asp Ile Gln Met Thr Gln Ser Pro Ser Thr Leu Ser Ala Ser Val Gly
1               5                   10                  15

```
Asp Arg Val Thr Ile Thr Cys Ser Ala Ser Ser Val Gly Tyr Met
            20                  25                  30

His Trp Tyr Gln Gln Lys Pro Gly Lys Ala Pro Lys Leu Leu Ile Tyr
            35                  40                  45

Asp Thr Phe Arg Leu Ala Ser Gly Val Pro Ser Arg Phe Ser Gly Ser
        50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Leu Glu Ile Lys
            100                 105

<210> SEQ ID NO 66
<211> LENGTH: 7
<212> TYPE: PRT
<213> ORGANISM: Homo sapiens

<400> SEQUENCE: 66

Asp Thr Phe Arg Leu Ala Ser
1               5

<210> SEQ ID NO 67
<211> LENGTH: 120
<212> TYPE: PRT
<213> ORGANISM: Homo sapiens

<400> SEQUENCE: 67

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ala
            20                  25                  30

Gly Met Ser Val Gly Trp Ile Arg Gln Pro Pro Gly Lys Ala Leu Glu
        35                  40                  45

Trp Leu Ala Asp Ile Trp Trp Asp Asp Lys Lys His Tyr Asn Pro Ser
50                  55                  60

Leu Lys Asp Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
                85                  90                  95

Cys Ala Arg Asp Met Ile Phe Asn Trp Tyr Phe Asp Val Trp Gly Ala
            100                 105                 110

Gly Thr Thr Val Thr Val Ser Ser
        115                 120

<210> SEQ ID NO 68
<211> LENGTH: 106
<212> TYPE: PRT
<213> ORGANISM: Homo sapiens

<400> SEQUENCE: 68

Asp Ile Gln Met Thr Gln Ser Pro Ser Thr Leu Ser Ala Ser Val Gly
1               5                   10                  15

Asp Arg Val Thr Ile Thr Cys Ser Ala Ser Ser Val Gly Tyr Met
            20                  25                  30

His Trp Tyr Gln Gln Lys Pro Gly Lys Ala Pro Lys Leu Leu Ile Tyr
            35                  40                  45

Asp Thr Tyr Arg His Ala Ser Gly Val Pro Ser Arg Phe Ser Gly Ser
```

```
                50                  55                  60
Gly Ser Gly Thr Glu Phe Thr Leu Thr Ile Ser Ser Leu Gln Pro Asp
 65                  70                  75                  80

Asp Phe Ala Thr Tyr Tyr Cys Phe Gln Gly Ser Gly Tyr Pro Phe Thr
                 85                  90                  95

Phe Gly Gly Gly Thr Lys Leu Glu Ile Lys
                100                 105

<210> SEQ ID NO 69
<211> LENGTH: 7
<212> TYPE: PRT
<213> ORGANISM: Homo sapiens

<400> SEQUENCE: 69

Asp Thr Tyr Arg His Ser Ser
 1               5

<210> SEQ ID NO 70
<211> LENGTH: 106
<212> TYPE: PRT
<213> ORGANISM: Homo sapiens

<400> SEQUENCE: 70

Asp Ile Gln Met Thr Gln Ser Pro Ser Thr Leu Ser Ala Ser Val Gly
 1               5                  10                  15

Asp Arg Val Thr Ile Thr Cys Ser Ala Ser Ser Ser Val Gly Tyr Met
                 20                  25                  30

His Trp Tyr Gln Gln Lys Pro Gly Lys Ala Pro Lys Leu Leu Ile Tyr
                 35                  40                  45

Asp Thr Tyr Lys Gln Thr Ser Gly Val Pro Ser Arg Phe Ser Gly Ser
 50                  55                  60

Gly Ser Gly Thr Glu Phe Thr Leu Thr Ile Ser Ser Leu Gln Pro Asp
 65                  70                  75                  80

Asp Phe Ala Thr Tyr Tyr Cys Phe Gln Gly Ser Gly Tyr Pro Phe Thr
                 85                  90                  95

Phe Gly Gly Gly Thr Lys Leu Glu Ile Lys
                100                 105

<210> SEQ ID NO 71
<211> LENGTH: 106
<212> TYPE: PRT
<213> ORGANISM: Homo sapiens

<400> SEQUENCE: 71

Asp Ile Gln Met Thr Gln Ser Pro Ser Thr Leu Ser Ala Ser Val Gly
 1               5                  10                  15

Asp Arg Val Thr Ile Thr Cys Ser Leu Ser Ser Ser Val Gly Tyr Met
                 20                  25                  30

His Trp Tyr Gln Gln Lys Pro Gly Lys Ala Pro Lys Leu Leu Ile Tyr
                 35                  40                  45

Asp Thr Phe Phe His Arg Ser Gly Val Pro Ser Arg Phe Ser Gly Ser
 50                  55                  60

Gly Ser Gly Thr Glu Phe Thr Leu Thr Ile Ser Ser Leu Gln Pro Asp
 65                  70                  75                  80

Asp Phe Ala Thr Tyr Tyr Cys Phe Gln Gly Ser Gly Tyr Pro Phe Thr
                 85                  90                  95

Phe Gly Gly Gly Thr Lys Leu Glu Ile Lys
                100                 105
```

```
<210> SEQ ID NO 72
<211> LENGTH: 10
<212> TYPE: PRT
<213> ORGANISM: Homo sapiens

<400> SEQUENCE: 72

Ser Leu Ser Ser Ser Val Gly Tyr Met His
1               5                   10

<210> SEQ ID NO 73
<211> LENGTH: 7
<212> TYPE: PRT
<213> ORGANISM: Homo sapiens

<400> SEQUENCE: 73

Asp Thr Phe Phe His Arg Ser
1               5

<210> SEQ ID NO 74
<211> LENGTH: 106
<212> TYPE: PRT
<213> ORGANISM: Homo sapiens

<400> SEQUENCE: 74

Asp Ile Gln Met Thr Gln Ser Pro Ser Thr Leu Ser Ala Ser Val Gly
1               5                   10                  15

Asp Arg Val Thr Ile Thr Cys Ser Ala Ser Ser Arg Val Gly Tyr Met
                20                  25                  30

His Trp Tyr Gln Gln Lys Pro Gly Lys Ala Pro Lys Leu Leu Ile Tyr
            35                  40                  45

Asp Thr Leu Leu Leu Asp Ser Gly Val Pro Ser Arg Phe Ser Gly Ser
        50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Leu Glu Ile Lys
            100                 105

<210> SEQ ID NO 75
<211> LENGTH: 7
<212> TYPE: PRT
<213> ORGANISM: Homo sapiens

<400> SEQUENCE: 75

Asp Thr Leu Leu Leu Asp Ser
1               5

<210> SEQ ID NO 76
<211> LENGTH: 106
<212> TYPE: PRT
<213> ORGANISM: Homo sapiens

<400> SEQUENCE: 76

Asp Ile Gln Met Thr Gln Ser Pro Ser Thr Leu Ser Ala Ser Val Gly
1               5                   10                  15

Asp Arg Val Thr Ile Thr Cys Ser Ala Ser Ser Arg Val Gly Tyr Met
                20                  25                  30

His Trp Tyr Gln Gln Lys Pro Gly Lys Ala Pro Lys Leu Leu Ile Tyr
            35                  40                  45
```

```
Asp Thr Ser Phe Leu Asp Ser Gly Val Pro Ser Arg Phe Ser Gly Ser
        50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Leu Glu Ile Lys
            100                 105

<210> SEQ ID NO 77
<211> LENGTH: 7
<212> TYPE: PRT
<213> ORGANISM: Homo sapiens

<400> SEQUENCE: 77

Asp Thr Ser Phe Leu Asp Ser
1               5

<210> SEQ ID NO 78
<211> LENGTH: 120
<212> TYPE: PRT
<213> ORGANISM: Homo sapiens

<400> SEQUENCE: 78

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ala
                20                  25                  30

Gly Met Ser Val Gly Trp Ile Arg Gln Pro Pro Gly Lys Ala Leu Glu
            35                  40                  45

Trp Leu Ala Asp Ile Trp Trp Asp Asp Lys Lys Asp Tyr Asn Pro Ser
    50                  55                  60

Leu Lys Ser Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
                85                  90                  95

Cys Ala Arg Asp Met Ile Thr Asn Phe Tyr Phe Asp Val Trp Gly Ala
            100                 105                 110

Gly Thr Thr Val Thr Val Ser Ser
        115                 120

<210> SEQ ID NO 79
<211> LENGTH: 10
<212> TYPE: PRT
<213> ORGANISM: Homo sapiens

<400> SEQUENCE: 79

Asp Met Ile Thr Asn Phe Tyr Phe Asp Val
1               5                   10

<210> SEQ ID NO 80
<211> LENGTH: 109
<212> TYPE: PRT
<213> ORGANISM: Homo sapiens

<400> SEQUENCE: 80

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
```

```
                20                  25                  30
Val Val Asp Val Ser His Glu Asp Pro Glu Val Lys Phe Asn Trp Tyr
            35                  40                  45

Val Asp Gly Val Glu Val His Asn Ala Lys Thr Lys Pro Arg Glu Glu
        50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala
            100                 105

<210> SEQ ID NO 81
<211> LENGTH: 108
<212> TYPE: PRT
<213> ORGANISM: Homo sapiens

<400> SEQUENCE: 81

Lys Gly Gln Pro Arg Glu Pro Gln Val Tyr Thr Leu Pro Pro Ser Arg
1               5                   10                  15

Glu Glu Met Thr Lys Asn Gln Val Ser Leu Thr Cys Leu Val Lys Gly
            20                  25                  30

Phe Tyr Pro Ser Asp Ile Ala Val Glu Trp Glu Ser Asn Gly Gln Pro
        35                  40                  45

Glu Asn Asn Tyr Lys Thr Thr Pro Pro Val Leu Asp Ser Asp Gly Ser
    50                  55                  60

Phe Phe Leu Tyr Ser Lys Leu Thr Val Asp Lys Ser Arg Trp Gln Gln
65                  70                  75                  80

Gly Asn Val Phe Ser Cys Ser Val Met His Glu Ala Leu His Asn His
                85                  90                  95

Tyr Thr Gln Lys Ser Leu Ser Leu Ser Pro Gly Lys
            100                 105

<210> SEQ ID NO 82
<211> LENGTH: 15
<212> TYPE: PRT
<213> ORGANISM: Homo sapiens

<400> SEQUENCE: 82

Glu Pro Lys Ser Cys Asp Lys Thr His Thr Cys Pro Pro Cys Pro
1               5                   10                  15

<210> SEQ ID NO 83
<211> LENGTH: 232
<212> TYPE: PRT
<213> ORGANISM: Homo sapiens

<400> SEQUENCE: 83

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80
```

-continued

```
Tyr Asn Ser Thr Tyr Arg Val Val Ser Val Leu Thr Val Leu His Gln
                 85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 84
<211> LENGTH: 365
<212> TYPE: PRT
<213> ORGANISM: Homo sapiens

<400> SEQUENCE: 84

Met Gly Val Pro Arg Pro Gln Pro Trp Ala Leu Gly Leu Leu Leu Phe
1               5                   10                  15

Leu Leu Pro Gly Ser Leu Gly Ala Glu Ser His Leu Ser Leu Leu Tyr
            20                  25                  30

His Leu Thr Ala Val Ser Ser Pro Ala Pro Gly Thr Pro Ala Phe Trp
        35                  40                  45

Val Ser Gly Trp Leu Gly Pro Gln Gln Tyr Leu Ser Tyr Asn Ser Leu
    50                  55                  60

Arg Gly Glu Ala Glu Pro Cys Gly Ala Trp Val Trp Glu Asn Gln Val
65                  70                  75                  80

Ser Trp Tyr Trp Glu Lys Glu Thr Thr Asp Leu Arg Ile Lys Glu Lys
                85                  90                  95

Leu Phe Leu Glu Ala Phe Lys Ala Leu Gly Gly Lys Gly Pro Tyr Thr
            100                 105                 110

Leu Gln Gly Leu Leu Gly Cys Glu Leu Gly Pro Asp Asn Thr Ser Val
        115                 120                 125

Pro Thr Ala Lys Phe Ala Leu Asn Gly Glu Glu Phe Met Asn Phe Asp
    130                 135                 140

Leu Lys Gln Gly Thr Trp Gly Gly Asp Trp Pro Glu Ala Leu Ala Ile
145                 150                 155                 160

Ser Gln Arg Trp Gln Gln Gln Asp Lys Ala Ala Asn Lys Glu Leu Thr
                165                 170                 175

Phe Leu Leu Phe Ser Cys Pro His Arg Leu Arg Glu His Leu Glu Arg
            180                 185                 190

Gly Arg Gly Asn Leu Glu Trp Lys Glu Pro Pro Ser Met Arg Leu Lys
        195                 200                 205

Ala Arg Pro Ser Ser Pro Gly Phe Ser Val Leu Thr Cys Ser Ala Phe
```

-continued

```
                210                 215                 220
Ser Phe Tyr Pro Pro Glu Leu Gln Leu Arg Phe Leu Arg Asn Gly Leu
225                 230                 235                 240

Ala Ala Gly Thr Gly Gln Gly Asp Phe Gly Pro Asn Ser Asp Gly Ser
                245                 250                 255

Phe His Ala Ser Ser Ser Leu Thr Val Lys Ser Gly Asp Glu His His
                260                 265                 270

Tyr Cys Cys Ile Val Gln His Ala Gly Leu Ala Gln Pro Leu Arg Val
                275                 280                 285

Glu Leu Glu Ser Pro Ala Lys Ser Ser Val Leu Val Gly Ile Val
        290                 295                 300

Ile Gly Val Leu Leu Thr Ala Ala Val Gly Gly Ala Leu Leu
305                 310                 315                 320

Trp Arg Arg Met Arg Ser Gly Leu Pro Ala Pro Trp Ile Ser Leu Arg
                325                 330                 335

Gly Asp Asp Thr Gly Val Leu Leu Pro Thr Pro Gly Glu Ala Gln Asp
                340                 345                 350

Ala Asp Leu Lys Asp Val Asn Val Ile Pro Ala Thr Ala
        355                 360                 365

<210> SEQ ID NO 85
<211> LENGTH: 365
<212> TYPE: PRT
<213> ORGANISM: Mus sp.

<400> SEQUENCE: 85

Met Gly Met Pro Leu Pro Trp Ala Leu Ser Leu Leu Val Leu Leu
1               5                   10                  15

Pro Gln Thr Trp Gly Ser Glu Thr Arg Pro Pro Leu Met Tyr His Leu
                20                  25                  30

Thr Ala Val Ser Asn Pro Ser Thr Gly Leu Pro Ser Phe Trp Ala Thr
                35                  40                  45

Gly Trp Leu Gly Pro Gln Gln Tyr Leu Thr Tyr Asn Ser Leu Arg Gln
        50                  55                  60

Glu Ala Asp Pro Cys Gly Ala Trp Val Trp Glu Asn Gln Val Ser Trp
65                  70                  75                  80

Tyr Trp Glu Lys Glu Thr Thr Asp Leu Lys Ser Lys Glu Gln Leu Phe
                85                  90                  95

Leu Glu Ala Leu Lys Thr Leu Glu Lys Ile Leu Asn Gly Thr Tyr Thr
                100                 105                 110

Leu Gln Gly Leu Leu Gly Cys Glu Leu Ala Ser Asp Asn Ser Ser Val
        115                 120                 125

Pro Thr Ala Val Phe Ala Leu Asn Gly Glu Glu Phe Met Lys Phe Asn
130                 135                 140

Pro Arg Ile Gly Asn Trp Thr Gly Glu Trp Pro Glu Thr Glu Ile Val
                145                 150                 155                 160

Ala Asn Leu Trp Met Lys Gln Pro Asp Ala Ala Arg Lys Glu Ser Glu
                165                 170                 175

Phe Leu Leu Asn Ser Cys Pro Glu Arg Leu Leu Gly His Leu Glu Arg
                180                 185                 190

Gly Arg Arg Asn Leu Glu Trp Lys Glu Pro Pro Ser Met Arg Leu Lys
        195                 200                 205

Ala Arg Pro Gly Asn Ser Gly Ser Ser Val Leu Thr Cys Ala Ala Phe
210                 215                 220
```

```
Ser Phe Tyr Pro Pro Glu Leu Lys Phe Arg Phe Leu Arg Asn Gly Leu
225                 230                 235                 240

Ala Ser Gly Ser Gly Asn Cys Ser Thr Gly Pro Asn Gly Asp Gly Ser
            245                 250                 255

Phe His Ala Trp Ser Leu Leu Glu Val Lys Arg Gly Asp Glu His His
        260                 265                 270

Tyr Gln Cys Gln Val Glu His Glu Gly Leu Ala Gln Pro Leu Thr Val
    275                 280                 285

Asp Leu Asp Ser Ser Ala Arg Ser Ser Val Pro Val Val Gly Ile Val
290                 295                 300

Leu Gly Leu Leu Leu Val Val Ala Ile Ala Gly Val Leu Leu
305                 310                 315                 320

Trp Gly Arg Met Arg Ser Gly Leu Pro Ala Pro Trp Leu Ser Leu Ser
                325                 330                 335

Gly Asp Asp Ser Gly Asp Leu Leu Pro Gly Gly Asn Leu Pro Pro Glu
                340                 345                 350

Ala Glu Pro Gln Gly Ala Asn Ala Phe Pro Ala Thr Ser
                355                 360                 365

<210> SEQ ID NO 86
<211> LENGTH: 7
<212> TYPE: PRT
<213> ORGANISM: Homo sapiens

<400> SEQUENCE: 86

Val Leu His Gln Asp Trp Leu
1               5

<210> SEQ ID NO 87
<211> LENGTH: 6
<212> TYPE: PRT
<213> ORGANISM: Homo sapiens

<400> SEQUENCE: 87

Leu Met Ile Ser Arg Thr
1               5

<210> SEQ ID NO 88
<211> LENGTH: 9
<212> TYPE: PRT
<213> ORGANISM: Homo sapiens

<400> SEQUENCE: 88

Met His Glu Ala Leu His Asn His Tyr
1               5

<210> SEQ ID NO 89
<211> LENGTH: 5
<212> TYPE: PRT
<213> ORGANISM: Homo sapiens

<400> SEQUENCE: 89

Gly Gln Pro Glu Asn
1               5

<210> SEQ ID NO 90
<211> LENGTH: 6
<212> TYPE: PRT
<213> ORGANISM: Homo sapiens

<400> SEQUENCE: 90
```

```
Leu Tyr Ile Thr Arg Glu
1               5

<210> SEQ ID NO 91
<211> LENGTH: 6
<212> TYPE: PRT
<213> ORGANISM: Homo sapiens

<400> SEQUENCE: 91

Leu Tyr Ile Ser Arg Thr
1               5

<210> SEQ ID NO 92
<211> LENGTH: 6
<212> TYPE: PRT
<213> ORGANISM: Homo sapiens

<400> SEQUENCE: 92

Leu Tyr Ile Ser Arg Ser
1               5

<210> SEQ ID NO 93
<211> LENGTH: 6
<212> TYPE: PRT
<213> ORGANISM: Homo sapiens

<400> SEQUENCE: 93

Leu Tyr Ile Ser Arg Arg
1               5

<210> SEQ ID NO 94
<211> LENGTH: 6
<212> TYPE: PRT
<213> ORGANISM: Homo sapiens

<400> SEQUENCE: 94

Leu Tyr Ile Ser Arg Gln
1               5

<210> SEQ ID NO 95
<211> LENGTH: 6
<212> TYPE: PRT
<213> ORGANISM: Homo sapiens

<400> SEQUENCE: 95

Leu Trp Ile Ser Arg Thr
1               5

<210> SEQ ID NO 96
<211> LENGTH: 6
<212> TYPE: PRT
<213> ORGANISM: Homo sapiens

<400> SEQUENCE: 96

Leu Tyr Ile Ser Leu Gln
1               5

<210> SEQ ID NO 97
<211> LENGTH: 6
<212> TYPE: PRT
<213> ORGANISM: Homo sapiens

<400> SEQUENCE: 97

Leu Phe Ile Ser Arg Asp
1               5
```

<210> SEQ ID NO 98
<211> LENGTH: 6
<212> TYPE: PRT
<213> ORGANISM: Homo sapiens

<400> SEQUENCE: 98

Leu Phe Ile Ser Arg Thr
1               5

<210> SEQ ID NO 99
<211> LENGTH: 6
<212> TYPE: PRT
<213> ORGANISM: Homo sapiens

<400> SEQUENCE: 99

Leu Phe Ile Ser Arg Arg
1               5

<210> SEQ ID NO 100
<211> LENGTH: 6
<212> TYPE: PRT
<213> ORGANISM: Homo sapiens

<400> SEQUENCE: 100

Leu Phe Ile Thr Gly Ala
1               5

<210> SEQ ID NO 101
<211> LENGTH: 6
<212> TYPE: PRT
<213> ORGANISM: Homo sapiens

<400> SEQUENCE: 101

Leu Ser Ile Ser Arg Glu
1               5

<210> SEQ ID NO 102
<211> LENGTH: 6
<212> TYPE: PRT
<213> ORGANISM: Homo sapiens

<400> SEQUENCE: 102

Arg Thr Ile Ser Ile Ser
1               5

<210> SEQ ID NO 103
<211> LENGTH: 7
<212> TYPE: PRT
<213> ORGANISM: Homo sapiens

<400> SEQUENCE: 103

Thr Pro His Ser Asp Trp Leu
1               5

<210> SEQ ID NO 104
<211> LENGTH: 7
<212> TYPE: PRT
<213> ORGANISM: Homo sapiens

<400> SEQUENCE: 104

Ile Pro His Glu Asp Trp Leu
1               5

```
<210> SEQ ID NO 105
<211> LENGTH: 5
<212> TYPE: PRT
<213> ORGANISM: Homo sapiens

<400> SEQUENCE: 105

Arg Thr Arg Glu Pro
1               5

<210> SEQ ID NO 106
<211> LENGTH: 5
<212> TYPE: PRT
<213> ORGANISM: Homo sapiens

<400> SEQUENCE: 106

Asp Pro Pro Glu Ser
1               5

<210> SEQ ID NO 107
<211> LENGTH: 5
<212> TYPE: PRT
<213> ORGANISM: Homo sapiens

<400> SEQUENCE: 107

Ser Asp Pro Glu Pro
1               5

<210> SEQ ID NO 108
<211> LENGTH: 5
<212> TYPE: PRT
<213> ORGANISM: Homo sapiens

<400> SEQUENCE: 108

Thr Ser His Glu Asn
1               5

<210> SEQ ID NO 109
<211> LENGTH: 5
<212> TYPE: PRT
<213> ORGANISM: Homo sapiens

<400> SEQUENCE: 109

Ser Lys Ser Glu Asn
1               5

<210> SEQ ID NO 110
<211> LENGTH: 5
<212> TYPE: PRT
<213> ORGANISM: Homo sapiens

<400> SEQUENCE: 110

His Arg Ser Glu Asn
1               5

<210> SEQ ID NO 111
<211> LENGTH: 5
<212> TYPE: PRT
<213> ORGANISM: Homo sapiens

<400> SEQUENCE: 111

Lys Ile Arg Glu Asn
1               5

<210> SEQ ID NO 112
<211> LENGTH: 5
```

```
<212> TYPE: PRT
<213> ORGANISM: Homo sapiens

<400> SEQUENCE: 112

Gly Ile Thr Glu Ser
1               5

<210> SEQ ID NO 113
<211> LENGTH: 5
<212> TYPE: PRT
<213> ORGANISM: Homo sapiens

<400> SEQUENCE: 113

Ser Met Ala Glu Pro
1               5

<210> SEQ ID NO 114
<211> LENGTH: 9
<212> TYPE: PRT
<213> ORGANISM: Homo sapiens

<400> SEQUENCE: 114

Met His Glu Ala Leu Arg Tyr His His
1               5

<210> SEQ ID NO 115
<211> LENGTH: 9
<212> TYPE: PRT
<213> ORGANISM: Homo sapiens

<400> SEQUENCE: 115

Met His Glu Ala Leu His Phe His His
1               5

<210> SEQ ID NO 116
<211> LENGTH: 9
<212> TYPE: PRT
<213> ORGANISM: Homo sapiens

<400> SEQUENCE: 116

Met His Glu Ala Leu Lys Phe His His
1               5

<210> SEQ ID NO 117
<211> LENGTH: 9
<212> TYPE: PRT
<213> ORGANISM: Homo sapiens

<400> SEQUENCE: 117

Met His Glu Ala Leu Ser Tyr His Arg
1               5

<210> SEQ ID NO 118
<211> LENGTH: 9
<212> TYPE: PRT
<213> ORGANISM: Homo sapiens

<400> SEQUENCE: 118

Thr His Glu Ala Leu His Tyr His Thr
1               5
```

MOLECULES WITH EXTENDED HALF-LIVES, COMPOSITIONS AND USES THEREOF

This application claims the benefit of U.S. provisional application Ser. Nos. 60/254,884, filed Dec. 12, 2000, and 60/289,760, filed May 9, 2001, both of which are incorporated by reference herein in their entireties.

This invention was made, in part, with United States Government support under award number A139167 from the National Institute of Health. The United States Government may have certain rights in the invention.

1. INTRODUCTION

The present invention relates to molecules whose in vivo half-lives are increased by modification of an IgG constant domain, or FcRn (Fc Receptor-neonate) binding domain thereof. Specifically, these molecules have amino acid modifications that increase the affinity of the constant domain or fragment thereof for the FcRn. Increasing the half-life of therapeutic and diagnostic IgGs and other bioactive molecules using methods of the invention has many benefits including reducing the amount and/or frequency of dosing of these molecules, for example, in vaccines, passive immunotherapy and other therapeutic and prophylactic methods. The invention further relates to fusion proteins containing all or a portion (a FcRn binding portion) of an IgG constant domain having one or more of these amino acid modifications and a non-IgG protein or non-protein molecule conjugated to such a modified IgG constant domain, where the presence of the modified IgG constant domain increases the in vivo half-life of the non-IgG protein or molecule.

2. BACKGROUND OF THE INVENTION

The use of immunoglobulins as therapeutic agents has increased dramatically in recent years and have expanded to different areas of medical treatments. Such uses include treatment of agammaglobulinemia and hypogammaglobulinemia, as immunosuppressive agents for treating autoimmune diseases and graft-vs.-host (GVH) diseases, the treatment of lymphoid malignancies, and passive immunotherapies for the treatment of various systemic and infectious diseases. Also, immunoglobulins are useful as in vivo diagnostic tools, for example, in diagnostic imaging procedures.

One critical issue in these therapies is the persistence of immunoglobulins in the circulation. The rate of immunoglobulin clearance directly affects the amount and frequency of dosage of the immunoglobulin. Increased dosage and frequency of dosage may cause adverse effects in the patient and also increase medical costs.

IgG is the most prevalent immunoglobulin class in humans and other mammals and is utilized in various types of immunotherapies and diagnostic procedures. The mechanism of IgG catabolism in the circulation has been elucidated through studies related to the transfer of passive immunity from mother to fetus/neonate through the placenta or yolk sac or through colostrum (maternofetal transfer of IgG via transcytosis) in rodents (Brambell, *Lancet*, ii:1087–1093, 1966; Rodewald, *J. Cell Biol.*, 71:666–670, 1976; Morris et al., In: *Antigen Absorption by the Gut*, pp. 3–22, 1978, University Park Press, Baltimore; Jones et al., *J. Clin. Invest.*, 51:2916–2927, 1972).

The involvement of certain receptors in the maternofetal transmission of maternal IgGs was first suggested by Brambell's group in their study on the intestinal absorption of maternal antibodies from ingested milk in newborn rats (Halliday, *Proc. R. Soc. B.*, 143:408–413, 1955; Halliday, *Proc. R. Soc. B.*, 144:427–430, 1955; Halliday, *Proc. R. Soc. B.*, 148:92–103, 1957; Morris, *Proc. R. Soc. B.*, 148:84–91, 1957; Brambell et al., *Proc. R. Soc. B.*, 149:1–11, 1958; Morris, *Proc. R. Soc. B.*, 160:276–292, 1964). Brambell et al. suggested, based on the observation that heterologous IgGs interfered with the transmission of a specific antibody, that IgG molecules from various species might have sufficiently similar structures or sequences that bind to common receptors (Brambell et al., *Proc. R. Soc. B.*, 149:1–11, 1958).

A high-affinity Fc receptor, FcRn, has been implicated in this transfer mechanism. The FcRn receptor has been isolated from duodenal epithelial brush borders of suckling rats (Rodewald et al., *J. Cell Biol.*, 99:154s–164s, 1984; Simister et al., *Eur. J. Immunol.*, 15:733–738, 1985) and the corresponding gene has been cloned (Simister et al., *Nature*, 337:184, 1989 and *Cold Spring Harbor Symp. Quant. Biol.*, LIV, 571–580, 1989). The later clonings of FcRn-encoding genes from mice (Ahouse et al., *J. Immunol.*, 151:6076–6088, 1993) and humans (Story et al., *J. Exp. Med.*, 180:2377–2381, 1994) demonstrate high homology of these sequences to the rat FcRn, suggesting a similar mechanism of maternofetal transmission of IgGs involving FcRn in these species.

Meanwhile, a mechanism for IgG catabolism was also proposed by Brambell's group (Brambell et al., *Nature*, 203:1352–1355, 1964; Brambell, *Lancet*, ii: 1087–1093, 1966). They proposed that a proportion of IgG molecules in the circulation are bound by certain cellular receptors (i. e., FcRn), which are saturable, whereby the IgGs are protected from degradation and eventually recycled into the circulation; on the other hand, IgGs which are not bound by the receptors are degraded. The proposed mechanism was consistent with the IgG catabolism observed in hypergammaglobulinemic or hypogammaglobulinemic patients. Furthermore, based on his studies as well as others (see, e.g., Spiegelberg et al., *J. Exp. Med.*, 121:323–338, 1965; Edelman et al., *Proc. Natl. Acad. Sci. USA*, 63:78–85, 1969), Brambell also suggested that the mechanisms involved in maternofetal transfer of IgG and catabolism of IgG may be either the same or, at least, very closely related (Brambell, *Lancet*, ii:1087–1093, 1966). Indeed, it was later reported that a mutation in the Fc-hinge fragment caused concomitant changes in catabolism, maternofetal transfer, neonatal transcytosis, and, particularly, binding to FcRn (Ghetie et al., *Immunology Today*, 18(12):592–598, 1997).

These observations suggested that portions of the IgG constant domain control IgG metabolism, including the rate of IgG degradation in the serum through interactions with FcRn. Indeed, increased binding affinity for FcRn increased the serum half-life of the molecule (Kim et al., *Eur. J. Immunol.*, 24:2429–2434, 1994; Popov et al., *Mol. Immunol.*, 33:493–502, 1996; Ghetie et al., *Eur. J. Immunol.*, 26:690–696, 1996; Junghans et al., *Proc. Natl. Acad. Sci. USA*, 93:5512–5516, 1996; Israel et al., *Immunol.*, 89:573–578, 1996).

Various site-specific mutagenesis experiments in the Fc region of mouse IgGs have led to identification of certain critical amino acid residues involved in the interaction between IgG and FcRn (Kim et al., *Eur. J. Immunol.*, 24:2429–2434, 1994; Medesan et al., *Eur. J. Immunol.*, 26:2533, 1996; Medesan et al., *J. Immunol.*, 158:2211–2217, 1997). These studies and sequence comparison studies found that isoleucine at position 253, histidine at position 310, and histidine at position 435 (according to Kabat numbering, Kabat et al., In: *Sequences of Proteins of Immunological Interest*, U.S. Department of Health and Human Services, 1991, which is hereby incorporated by reference in its entirety), are highly conserved in human and rodent IgGs, suggesting their importance in IgG-FcRn binding.

Additionally, various publications describe methods for obtaining physiologically active molecules whose half-lives are modified either by introducing an FcRn-binding polypeptide into the molecules (WO 97/43316; U.S. Pat. No. 5,869,046; U.S. Pat. No. 5,747,035; WO 96/32478; WO 91/14438) or by fusing the molecules with antibodies whose FcRn-binding affinities are preserved but affinities for other Fc receptors have been greatly reduced (WO 99/43713) or fusing with FcRn binding domains of antibodies (WO 00/09560; U.S. Pat. No. 4,703,039). However, none of these publications disclose specific mutants in the IgG constant domain that affect half-life.

Prior studies have demonstrated that certain constant domain mutations actually reduce binding to FcRn and, thereby, reduce the IgG in vivo half-life. PCT publication WO 93/22332 (by Ward et al.) discloses various recombinant mouse IgGs whose in vivo half-lives are reduced by mutations between about residue 253 and about residue 434. Particularly, substitutions of isoleucine at position 253; histidine at position 310; glutamine at position 311; His at position 433; and asparagine at position 434 were found to reduce IgG half-life.

Modulation of IgG molecules by amino acid substitution, addition, or deletion to increase or reduce affinity for FcR-n is also disclosed in WO 98/23289; however, the publication does not list any specific mutants that exhibit either longer or shorter in vivo half-lives.

In fact, only one mutant of mouse IgGI that actually exhibited increased half-life, the triple mutation Thr252 to Ala, Thr254 to Ser, and Thr256 to Phe, has been identified (WO 97/34631).

In view of the pharmaceutical importance of increasing the in vivo half-lives of immunoglobulins and other bioactive molecules, there is a need to develop modified IgGs and FcRn-binding fragments thereof, (particularly modified human IgGs) that confer increased in vivo half-life on immunoglobulins and other bioactive molecules.

3. SUMMARY OF THE INVENTION

The present invention is based upon the inventors' identification of several mutations in the constant domain of a human IgG molecule that increase the affinity of the IgG molecule for the FcRn. In particular, the present inventors have screened libraries of human IgG1 constant domains with random amino acid mutations introduced into particular regions of the constant domain for increased affinity for FcRn. Such random mutations were made in the regions of residues 251–256, 285–290, and 308–314, all of which are in CH2 domain, and 385–389 and 428–436, which are in CH3 domain, of human IgG1 hinge-Fc regions (residues as depicted in FIG. 2 (SEQ ID NO:83 or analogous residues in hinge-Fc regions of other IgG molecules as determined by sequence alignment). As used herein, all residues of the IgG constant domain are numbered according to Kabat et al. (Sequences of Proteins of Immunological Interest, U.S. Department of Health and Human Services, 1991, which is incorporated by reference herein in its entirety) and as presented in FIG. 2 (SEQ ID NO:83), and include corresponding residues in other IgG constant domains as determined by sequence alignment. The in vivo half-life, or persistence in serum or other tissues of a subject, of antibodies, and other therapeutic agents and other bioactive molecules is an important clinical parameter which determines the amount and frequency of antibody (or any other pharmaceutical molecule) administration. Accordingly, such molecules, including antibodies, with increased half-life are of significant pharmaceutical importance.

Thus, the present invention relates to a modified molecule (preferably a protein, but may be a non-protein agent) that has an increased in vivo half-life by virtue of the presence of a modified IgG constant domain, or FcRn-binding portion thereof (preferably the Fc or hinge-Fc domain) (preferably from a human IgG) wherein the IgG constant domain, or fragment thereof, is modified (e.g., by amino acid substitution, deletion or insertion) to increase the affinity for the FcRn. In a particular embodiment, the present invention relates to modified IgGs, whose in vivo half-lives are extended by the modification of amino acid residues identified to be involved in the interaction of the hinge-Fc domain with the FcRn receptor. Preferably, the constant domain or fragment thereof has higher affinity for FcRn at pH 6.0 than at pH 7.4. Such modifications may also alter (i.e., increase or decrease) the bioavailability (e.g., transport to mucosal surfaces, or other target tissues) of the molecules. The invention also relates to other types of immunoglobulins or fragments thereof (i.e., non-IgG immunoglobulins), non-immunoglobulin proteins and non-protein agents that are fused or conjugated to, or engineered to contain, an IgG constant domain, or FcRn-binding fragment thereof, having one or more such amino acid modifications.

In preferred embodiments, the present invention provides molecules, particularly, immunoglobulins whose in vivo half-lives are extended by the presence of an IgG constant domain, or FcRn binding fragment thereof (preferably, Fc or hinge-Fc domain), that has modifications of one or more of amino acid residues 251–256, 285–290, 308–314, 385–389, and 428–436 that increase the affinity of the constant domains or fragments thereof for FcRn. In certain embodiments, these modifications preferably exclude residues 252, 254, and 256, in particular when the IgG constant domain or fragment thereof, is murine. In particular embodiments, the modification is at one or more surface-exposed residues, and the modification is a substitution with a residue of similar charge, polarity or hydrophobicity to the residue being substituted. In preferred embodiments, the modified IgG constant domain, or fragment thereof, binds with higher affinity to FcRn at pH 6.0 than at pH 7.4. In a preferred embodiment, the constant domain, or fragment hereof, is modified by substitution of one or more of amino acid residues 251–256, 285–290, 308–314, 385–389, and 428–436 that increase the affinity of the constant domain or FcRn-binding fragments thereof for FcRn. In certain embodiments, substitutions of residue 252 with leucine, residue 254 with serine, and/or residue 256 with phenylalanine are excluded, particularly when the constant domain or fragment thereof is derived from a mouse IgG.

In specific embodiments, the invention provides immunoglobulins or other bioactive molecules that contain an IgG1 constant domain, or FcRn-binding fragment thereof (preferably Fc or hinge-Fc domain) (preferably human), having amino acid modifications at one or more of position 308, 309, 311, 312, and 314, more specifically, having substitutions at one or more of positions 308, 309, 311, 312 and 314 with threonine, proline, serine, aspartic acid and leucine respectively. In another embodiment, residues at one or more of positions 308, 309, and 311 are substituted with isoleucine, proline, and glutamic acid, respectively. In yet another embodiment, residues at one or more of positions 308, 309, 311, 312, and 314, are substituted with threonine, proline, serine, aspartic acid, and leucine, respectively. The invention further relates to combinations of these amino acid substitutions.

Furthermore, the invention provides immunoglobulins or other bioactive molecules that contain an IgG1 constant domain, or FcRn-binding fragment thereof (preferably, Fc or hinge-Fc domain) (preferably human), having amino acid modifications at one or more of positions 251, 252, 254, 255, and 256, more specifically, having substitutions at one or more of these positions. In specific embodiments, residue 251 is substituted with leucine or arginine, residue 252 is substituted with tyrosine, phenylalanine, serine, tryptophan or threonine, residue 254 is substituted with threonine or serine, residue 255 is substituted with leucine, glycine, isoleucine or arginine, and/or residue 256 is substituted with serine, arginine, glutamine, glutamic acid, aspartic acid, alanine, asparagine or threonine. In a more specific embodiment, residue 251 is substituted with leucine, residue 252 is substituted with tyrosine, residue 254 is substituted with threonine or serine, and/or residue 255 is substituted with arginine. In yet another specific embodiment, residue 252 is substituted with phenylalanine and/or residue 256 is substituted with aspartic acid. In a preferred embodiment, residue 251 is substituted with leucine, residue 252 is substituted with tyrosine, residue 254 is substituted with threonine or serine, and/or residue 255 is substituted with arginine. The invention further relates to any combination of these substitutions.

Furthermore, the invention provides immunoglobulins or other bioactive molecules that contain an IgG1 constant domain, or FcRn-binding fragment thereof (preferably, Fc or hinge-Fc domain) (preferably human), having amino acid modifications at one or more of positions 428, 433, 434, and 436, more specifically, having substitutions at one or more of these positions. In specific embodiments, residue 428 is substituted with methionine, threonine, leucine, phenylalanine, or serine, residue 433 is substituted with lysine, arginine, serine, isoleucine, proline, glutamine, or histidine, residue 434 is substituted with phenylalanine, tyrosine, or histidine, and/or residue 436 is substituted with histidine, asparagine, arginine, threonine, lysine, methionine, or threonine. In a more specific embodiment, residues at one or more positions 433, 434, and 436 are substituted with lysine, phenylalanine, and histidine, respectively. In a preferred embodiment, residue 428 is substituted with methionine and/or residue 434 is substituted with tyrosine.

Furthermore, the invention provides immunoglobulins or other bioactive molecules that contain an IgG1 constant domain, or FcRn-binding fragment thereof (preferably, Fc or hinge-Fc domain) (preferably human), having amino acid modifications at one or more positions 385, 386, 387, and 389, more specifically, having substitutions at one or more of these positions. In specific embodiments, residue 385 is substituted with arginine, aspartic acid, serine, threonine, histidine, lysine, or alanine, residue 386 is substituted with threonine, proline, aspartic acid, serine, lysine, arginine, isoleucine, or methionine, residue 387 is substituted with arginine, histidine, serine, threonine, alanine, or proline and/or residue 389 is substituted with proline or serine. In more specific embodiments, residues at one or more positions 385, 386, 387, and 389 are substituted with arginine, threonine, arginine, and proline, respectively. In yet another specific embodiment, residues at one or more positions 385, 386, and 389 are substituted with aspartic acid, proline, and serine, respectively.

Molecules of the invention include any combination of the above-described substitutions at one or more of residues 251, 252, 254, 255, 256, 308, 309, 311, 312, 385, 386, 387, 389, 428, 433, 434, and/or 436. In a preferred embodiment, the molecule of the invention contains a Fc region, or FcRn-binding domain thereof, having one or more of the following substitutions: leucine at residue 251, tyrosine at residue 252, threonine or serine at residue 254, arginine at residue 255, threonine at residue 308, proline at residue 309, serine at residue 311, aspartic acid at residue 312, leucine at residue 314, arginine at residue 385, threonine at residue 386, arginine at residue 387, proline at residue 389, methionine at residue 428, and/or tyrosine at residue 434.

Included within the invention are pharmaceutical compositions and methods of prophylaxis and therapy using modified immunoglobulins, proteins and other bioactive molecules of the invention having extended half-lives. Also included are methods of diagnosis using modified immunoglobulins, proteins and other bioactive molecules of the invention having extended half-lives. In a specific embodiment, the invention provides an anti-respiratory syncytial virus (RSV) antibody useful to treat or prevent RSV infection, such as SYNAGIS® (see U.S. Pat. No. 5,824,307 and Johnson et al., *J. Infectious Disease* 176:1215–1224, 1997, both of which are incorporated by reference in their entireties), and other anti-RSV antibodies, including variants of SYNAGIS® (see U.S. patent application Ser. No., 09/724,396, filed Nov. 28, 2000, U.S. patent application Ser. No. 09/724,531, filed Nov. 28, 2000, U.S. patent application Ser. No. 09/996,288, filed Nov. 28, 2001, and U.S. patent application Ser. No. 09/996,265, filed Nov. 28, 2001, all entitled "Methods of Administering/Dosing Anti-RSV Antibodies for Prophylaxis and Treatment," all by Young et al., all of which are incorporated by reference herein in their entireties, particularly the sequences of heavy and light chain variable domains and CDRs of anti-RSV antibodies disclosed therein), which has one or more amino acid modifications in the constant domain that increase the affinity of the antibody for FcRn and that has an increased in vivo half-life (see also, Section 5.1 infra).

3.1 Definitions

The term "IgG Fc region" as used herein refers the portion of an IgG molecule that correlates to a crystallizable fragment obtained by papain digestion of an IgG molecule. The Fc region consists of the C-terminal half of the two heavy chains of an IgG molecule that are linked by disulfide bonds. It has no antigen binding activity but contains the carbohydrate moiety and the binding sites for complement and Fc receptors, including the FcRn receptor (see below). The Fc fragment contains the entire second constant domain CH2 (residues 231–340 of human IgG1, according to the Kabat numbering system) (e.g., SEQ ID NO:80) and the third constant domain CH3 (residues 341–447) (e.g, SEQ ID NO:81).

The term "IgG hinge-Fc region" or "hinge-Fc fragment" as used herein refers to a region of an IgG molecule consisting of the Fc region (residues 231–447) and a hinge region (residues 216–230; e.g., SEQ ID NO:82) extending from the N-terminus of the Fc region. An example of the amino acid sequence of the human IgG1 hinge-Fc region is SEQ ID NO:83.

The term "constant domain" refers to the portion of an immunoglobulin molecule having a more conserved amino acid sequence relative to the other portion of the immunoglobulin, the variable domain, which contains the antigen binding site. The constant domain contains the CH1, CH2 and CH3 domains of the heavy chain and the CHL domain of the light chain.

The term "FcRn receptor" or "FcRn" as used herein refers to an Fc receptor ("n" indicates neonatal) which is known to be involved in transfer of maternal IgGs to a fetus through the human or primate placenta, or yolk sac (rabbits) and to a neonate from the colostrum through the small intestine. It is also known that FcRn is involved in the maintenance of constant serum IgG levels by binding the IgG molecules and recycling them into the serum. The binding of FcRn to IgG molecules is strictly pH-dependent with optimum binding at pH 6.0. FcRn comprises a heterodimer of two polypeptides, whose molecular weights are approximately 50 kD and 15 kD, respectively. The extracellular domains of the 50 kD polypeptide are related to major histocompatibility complex (MHC) class I α-chains and the 15 kD polypeptide was shown to be the non-polymorphic $β_2$-microglobulin ($β_2$-m). In addition to placenta and neonatal intestine, FcRn is also expressed in various tissues across species as well as various types of endothelial cell lines. It is also expressed in human adult vascular endothelium, muscle vasculature and hepatic sinusoids and it is suggested that the endothelial cells may be most responsible for the maintenance of serum IgG levels in humans and mice. The amino acid sequences of human FcRn and murine FcRn are indicated by SEQ ID NO:84 and SEQ ID NO:85, respectively. Homologs of these sequences having FcRn activity are also included.

The term "in vivo half-life" as used herein refers to a biological half-life of a particular type of IgG molecule or its fragments containing FcRn-binding sites in the circulation of a given animal and is represented by a time required for half the quantity administered in the animal to be cleared from the circulation and/or other tissues in the animal. When a clearance curve of a given IgG is constructed as a function of time, the curve is usually biphasic with a rapid α-phase which represents an equilibration of the injected IgG molecules between the intra- and extra-vascular space and which is, in part, determined by the size of molecules, and a longer β-phase which represents the catabolism of the IgG molecules in the intravascular space. The term "in vivo half-life" practically corresponds to the half life of the IgG molecules in the β-phase.

An "isolated" or "purified" antibody or fusion protein is substantially free of cellular material or other contaminating proteins from the cell or tissue source from which the protein is derived, or substantially free of chemical precursors or other chemicals when chemically synthesized. The language "substantially free of cellular material" includes preparations of an antibody or a fusion protein in which the antibody or the fusion protein is separated from cellular components of the cells from which it is isolated or recombinantly produced. Thus, an antibody or a fusion protein that is substantially free of cellular material includes preparations of antibody or fusion protein having less than about 30%, 20%, 10%, or 5% (by dry weight) of contaminating protein. When the antibody or the fusion protein is recombinantly produced, it is also preferably substantially free of culture medium, i.e., culture medium represents less than about 20%, 10%, or 5% of the volume of the protein preparation. When the antibody or the fusion protein is produced by chemical synthesis, it is preferably substantially free of chemical precursors or other chemicals, i.e., it is separated from chemical precursors or other chemicals which are involved in the synthesis of the protein. Accordingly such preparations of the antibody or the fusion protein have less than about 30%, 20%, 10%, 5% (by dry weight) of chemical precursors or compounds other than the antibody or antibody fragment of interest. In a preferred embodiment of the present invention, antibodies are isolated or purified. In another preferred embodiment of the invention, fusion proteins are isolated or purified.

An "isolated" nucleic acid molecule is one which is separated from other nucleic acid molecules which are present in the natural source of the nucleic acid molecule. Moreover, an "isolated" nucleic acid molecule, such as a cDNA molecule, can be substantially free of other cellular material, or culture medium when produced by recombinant techniques, or substantially free of chemical precursors or other chemicals when chemically synthesized. An "isolated" nucleic acid molecule does not include cDNA molecules within a cDNA library. In a preferred embodiment of the invention, nucleic acid molecules encoding antibodies are isolated or purified. In another preferred embodiment of the invention, nucleic acid molecules encoding fusion proteins are isolated or purified.

The term "host cell" as used herein refers to the particular subject cell transfected with a nucleic acid molecule or infected with phagemid or bacteriophage and the progeny or potential progeny of such a cell. Progeny of such a cell may not be identical to the parent cell transfected with the nucleic acid molecule due to mutations or environmental influences that may occur in succeeding generations or integration of the nucleic acid molecule into the host cell genome.

The names of amino acids referred to herein are abbreviated either with three-letter or one-letter symbols.

To determine the percent identity of two amino acid sequences or of two nucleic acid sequences, the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical overlapping positions/total number of positions×100%). In one embodiment, the two sequences are the same length.

The determination of percent identity between two sequences can also be accomplished using a mathematical algorithm. A preferred, non-limiting example of a mathematical algorithm utilized for the comparison of two sequences is the algorithm of Karlin and Altschul, 1990, *Proc. Natl. Acad. Sci. U.S.A.* 87:2264–2268, modified as in Karlin and Altschul, 1993, *Proc. Natl. Acad. Sci. U.S.A.* 90:5873–5877. Such an algorithm is incorporated into the NBLAST and XBLAST programs of Altschul et al., 1990, J. Mol. Biol. 215:403. BLAST nucleotide searches can be performed with the NBLAST nucleotide program parameters set, e.g., for score=100, wordlength=12 to obtain nucleotide sequences homologous to a nucleic acid molecules of the present invention. BLAST protein searches can be performed with the XBLAST program parameters set, e.g., to score-50, wordlength=3 to obtain amino acid sequences homologous to a protein molecule of the present invention. To obtain gapped alignments for comparison purposes, Gapped BLAST can be utilized as described in Altschul et al., 1997, *Nucleic Acids Res.* 25:3389–3402. Alternatively, PSI-BLAST can be used to perform an iterated search which detects distant relationships between molecules (Id.). When utilizing BLAST, Gapped BLAST, and PSI-Blast programs, the default parameters of the respective programs (e.g., of XBLAST and NBLAST) can be used (see, e.g., http://www.ncbi.nlm.nih.gov). Another preferred, non-limiting example of a mathematical algorithm utilized for the comparison of sequences is the algorithm of Myers and Miller, 1988, CABIOS 4:11–17. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

The percent identity between two sequences can be determined using techniques similar to those described above, with or without allowing gaps. In calculating percent identity, typically only exact matches are counted.

4. DESCRIPTION OF THE FIGURES

FIG. 2 shows the amino acid sequence of the human IgG1 hinge-Fc region (SEQ ID NO:83) containing a hinge region (SEQ ID NO:82), CH2 domain (SEQ ID NO:80), and CH3 domain (SEQ ID NO:81).

FIGS. 3(A and B) show the amino acid sequences of (A) human FcRn (SEQ ID NO:84) and (B) mouse FcRn (SEQ ID NO:85), respectively.

FIG. 4 shows the amino acid sequence of the human IgG1 hinge-Fc region (SEQ ID NO:83), in which wild-type residues which are mutated by amino acid substitutions are indicated in underlined bold-face.

FIGS. 7(A–D). (A) shows the binding of murine FcRn to immobilized IgG1 having M252Y/S254T/T256E substitutions. Murine FcRn was injected at 10 different concentrations ranging from 1 nM to 556 nM over a surface on which 4000 resonance units (RU) of IgG1 had been coupled. After equilibrium was reached, residual bound protein was eluted with a pulse of PBS, pH 7.4. (B) shows the binding of human FcRn to immobilized IgG1/M252Y/S254T/T256E. Murine FcRn was injected at 8 different concentrations ranging from 71 nM to 2.86 μM over a surface on which 1000 RU of IgG1 had been coupled. After equilibrium was reached, residual bound protein was eluted with a pulse of PBS, pH 7.4. (C) and (D) show scatchard analyses of the data in (A) and (B), respectively, after correction for nonspecific binding. $R_{eq}$ is the corrected equilibrium response at a given concentration C. The plots are linear with correlation coefficients of 0.97 and 0.998, respectively. The apparent $K_d$ are 24 nM and 225 nM, respectively.

FIGS. 8(A–H). (A)–(D) show the results from BIAcore analysis of the binding of murine FcRn at pH 6.0 and pH 7.4 to (A) wild type human IgG1, (B) M252Y/S254T/T256E, (C) H433K/N434F/Y436H, and (D) G385D/G386P/N389S, respectively, after correction for nonspecific binding. Murine FcRn was injected at a concentration of 1.1 μm over a surface on which 1000 RU of wild type IgG1, 1000 RU of M252Y/S254T/T256E, 955 RU of H433K/N434F/Y436H, and 939 RU of G385D/Q386P/N389S had been coupled. (E)–(H) show the results from BIAcore analysis of the binding of human FcRn at pH 6.0 and pH 7.4 to (E) wild type human IgG1, (F) M252Y/S254T/T256E, (G) H433K/N434F/Y436H, and (H) G385D/Q386P/N389S, respectively, after correction for nonspecific binding. Human FcRn was injected at a concentration of 1.4 μm over a surface on which 1000 RU of wild type IgG1, 1000 RU of M252Y/S254T/T256E, 955 RU of H433K/N434F/Y436H, and 939 RU of G385D/Q386P/N389S had been coupled.

Figure 9:
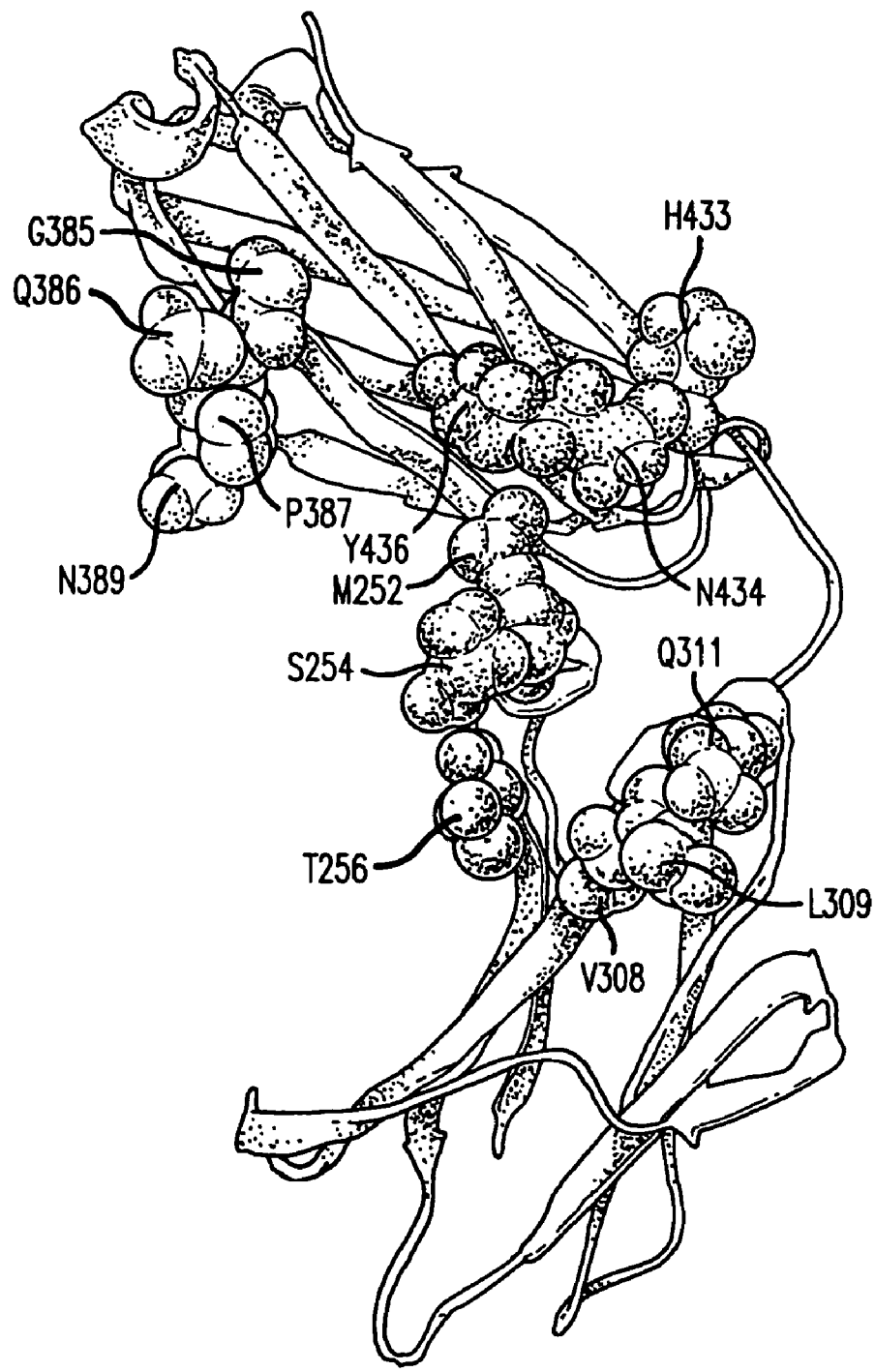

FIG. 9 shows the space-filling model of the surface of the Fc fragment of a human IgG1 based upon the human IgG1 structure of Deisenhofer, 1981, Biochemistry 20:2361–2370. Residues are color-coded according to the gain of free energy of stabilization of the Fc-FcRn complex: red, substitutions at these positions were found to increase affinity b a factor of at least 2.5 times in the Fc/human FcRn interaction and of at least 5 time in the Fc/mouse FcRn interaction; blue, substitutions at those positions were found to increase affinity by a factor of less than 2 times in both the Fc-human FcRn and Fc-mouse FcRn interaction. The figure was drawn using Swiss pdb viewer (Guex and Peitsch, 1997, Electrophoresis 18:2714–2723).

Figure 10:
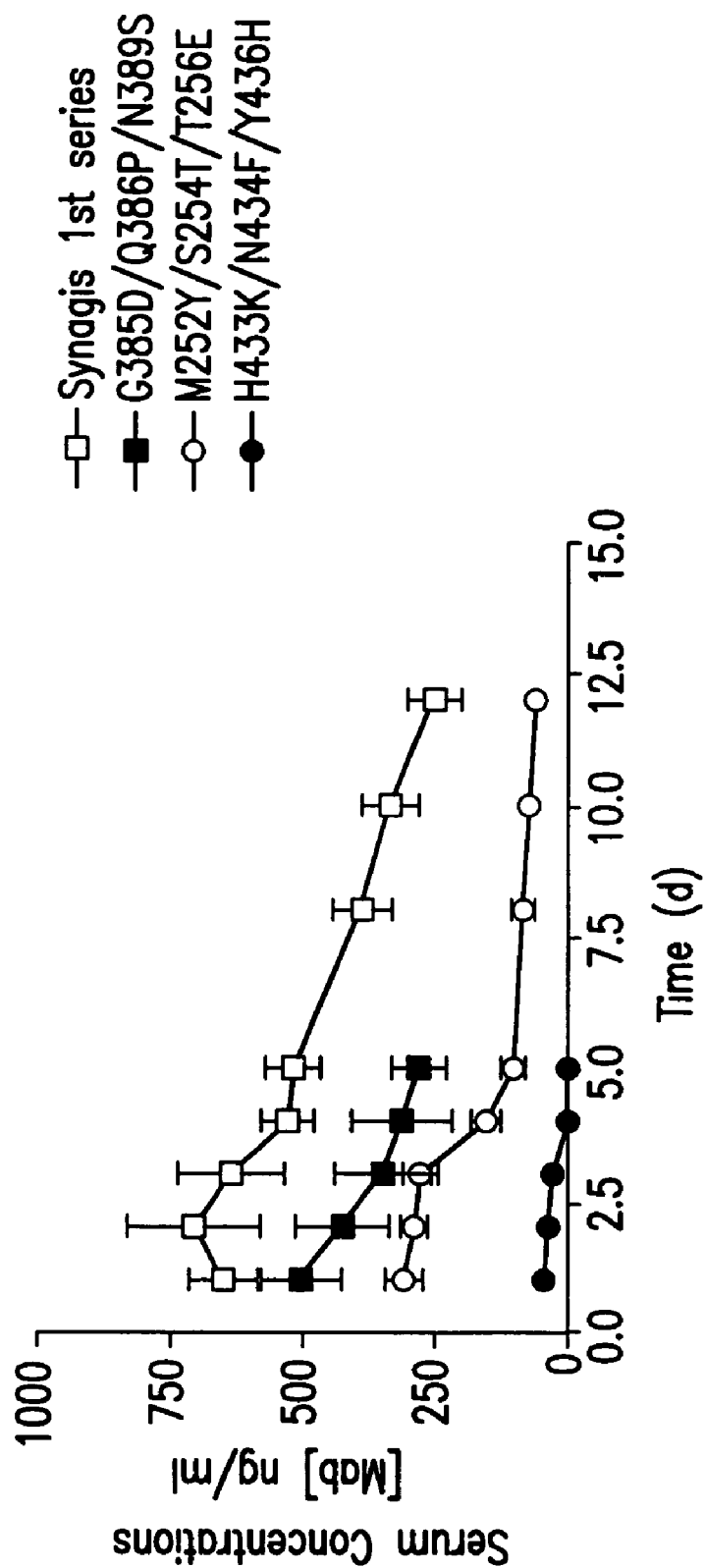

FIG. 10 shows the changes in serum concentration ([Mab] ng/ml) over time (in days) of antibody having a wild type constant domain (SYNAGIS®) (open squares), or constant domains with the following mutations: M252Y/S254T/T256E (open circles), G385D/Q386P/N389S (solid squares), and H433K/N434F/Y436H (solid circles). Antibody concentration was determined using anti-human IgG ELISA.

5. DETAILED DESCRIPTION OF THE INVENTION

The present invention relates to molecules, particularly proteins, more particularly immunoglobulins, that have an increased in vivo half-life and comprise an IgG constant domain, or fragment thereof that binds to an FcRn (preferably a Fc or hinge-Fc domain), that contains one or more amino acid modifications relative to a wild type IgG constant domain which modifications increase the affinity of the IgG constant domain, or fragment thereof, for the FcRn. In a preferred embodiment, the invention particularly relates to the modification of human or humanized IgGs and other bioactive molecules containing FcRn-binding portions of human IgGs, which have particular use in human therapy, prophylaxis and diagnosis.

5.1 Molecules with Increased In Vivo Half-Lives

The present invention is based upon identification of amino acid modifications in particular portions of the IgG constant domain that interact with the FcRn, which modifications increase the affinity of the IgG, or fragment thereof, for the FcRn. Accordingly, the invention relates to molecules, preferably proteins, more preferably immunoglobulins, that comprise an IgG constant domain, or FcRn binding fragment thereof (preferably a Fc or hinge-Fc domain fragment), having one or more amino acid modifications (i.e., substitutions, insertions or deletions) in one or more regions that interact with the FcRn, which modifications increase the affinity of the IgG or fragment thereof, for the FcRn, and also increase the in vivo half-life of the molecule. In preferred embodiments, the one or more amino acid modifications are made in one or more of residues 251–256, 285–290, 308–314, 385–389, and 428–436 of the IgG hinge-Fc region (for example, as in the human IgG1 hinge-Fc region depicted in FIG. 4, SEQ ID NO:83), or analogous residues thereof, as determined by amino acid sequence alignment, in other IgG hinge-Fc regions. In a preferred embodiment, the amino acid modifications are made in a human IgG constant domain, or FcRn-binding domain thereof. In a certain embodiment, the modifications are not made at residues 252, 254, or 256 (i.e., all are made at one or more of residues 251, 253, 255, 285–290, 308–314, 385–389, or 428–436) of the IgG constant domain. In a more preferred embodiment, the amino acid modifications are not the substitution with leucine at residue 252, with serine at 254, and/or with phenylalanine at position 256. In particular, in preferred embodiments, such modifications are not made when the IgG constant domain, hinge-Fc domain, hinge-Fc domain or other FcRn-binding fragment thereof is derived from a mouse.

The amino acid modifications may be any modification, preferably at one or more of residues 251–256, 285–290, 308–314, 385–389, and 428–436, that increases the in vivo half-life of the IgG constant domain, or FcRn-binding fragment thereof (e.g., Fc or hinge-Fc domain), and any molecule attached thereto, and increases the affinity of the IgG, or fragment thereof, for FcRn. Preferably, the one or more modifications also result in a higher binding affinity of the constant domain, or FcRn-binding fragment thereof, for FcRn at pH 6.0 than at pH 7.4. In other embodiments, the modifications alter (i.e., increase or decrease) bioavailability of the molecule, in particular, alters (i.e., increases or decreases) transport (or concentration or half-life) of the molecule to mucosal surfaces (e.g., of the lungs) or other portions of a target tissue. In a preferred embodiment, the amino acid modifications alter (preferably, increase) transport or concentration or half-life of the molecule to the lungs. In other embodiments, the amino acid modifications alter (preferably, increase) transport (or concentration or half-life) of the molecule to the heart, pancreas, liver, kidney, bladder, stomach, large or small intestine, respiratory tract, lymph nodes, nervous tissue (central and/or peripheral nervous tissue), muscle, epidermis, bone, cartilage, joints, blood vessels, bone marrow, prostate, ovary, uterine, tumor or cancer tissue, etc. In a preferred embodiment, the amino acid modifications do not abolish, or, more preferably, do not alter, other immune effector or receptor binding functions of the constant domain, for example, but not limited to complement fixation, ADCC and binding to FcγRI, FcγRII, and FcγRIII, as can be determined by methods well-known and routine in the art. In another preferred embodiment, the modified FcRn binding fragment of the constant domain does not contain sequences that mediate immune effector functions or other receptor binding. Such fragments may be particularly useful for conjugation to a non-IgG or non-immunoglobulin molecule to increase the in vivo half-life thereof. In yet another embodiment, the effector functions are selectively altered (e.g., to reduce or increase effector functions).

In preferred embodiments, the amino acid modifications are substitutions at one or more of residues 308, 309, 311, 312 and 314, particularly a substitution with threonine at position 308, proline at position 309, serine at position 311, aspartic acid at position 312, and/or leucine at position 314. Alternatively, the modification is the substitution with an isoleucine at position 308, proline at position 309, and/or a glutamic acid at position 311. In yet another embodiment, residues at one or more of positions 308, 309, 311, 312, and 314, are substituted with threonine, proline, leucine, alanine, and alanine, respectively. Accordingly, in certain embodiments the residue at position 308 is substituted with threonine or isoleucine, the residue at position 309 is substituted with proline, the residue at position 311 is substituted with serine, glutamic acid or leucine, the residue at position 312 is substituted with alanine, and/or the residue at position 314 is substituted with leucine or alanine. In a preferred embodiment, the substitution is a threonine at position 308, a proline at position 309, a serine at position 311, an aspartic acid at position 312, and/or a leucine at position 314.

In preferred embodiments, the amino acid modifications are substitutions at one or more of residues 251, 252, 254, 255, and 256. In specific embodiments, residue 251 is substituted with leucine or arginine, residue 252 is substituted with tyrosine, phenylalanine, serine, tryptophan or threonine, residue 254 is substituted with threonine or serine, residue 255 is substituted with arginine, leucine, glycine, or isoleucine, and/or residue 256 is substituted with serine, arginine, glutamine, glutamic acid, aspartic acid, alanine, asparagine or threonine. In a more specific embodiment, residue 251 is substituted with leucine, residue 252 is substituted with tyrosine, residue 254 is substituted with threonine or serine, residue 255 is substituted with arginine, and/or residue 256 is substituted with glutamic acid.

In preferred embodiments, the amino acid modifications are substitutions at one or more of residues 428, 433, 434, and 436. In specific embodiments, residue 428 is substituted with threonine, methionine, leucine, phenylalanine, or serine, residue 433 is substituted with lysine, arginine, serine, isoleucine, proline, glutamine or histidine, residue 434 is substituted with phenylalanine, tyrosine, or histidine, and/or residue 436 is substituted with histidine, asparagine, arginine, threonine, lysine, or methionine. In a more specific embodiment, residues at position 428 and/or 434 are substituted with methionine, and/or histidine respectively.

In preferred embodiments, the amino acid modifications are substitutions at one or more of residues 385, 386, 387, and 389, more specifically, having substitutions at one or more of these positions. In specific embodiments, residue 385 is substituted with arginine, aspartic acid, serine, threonine, histidine, lysine, alanine or glycine, residue 386 is substituted with threonine, proline, aspartic acid, serine, lysine, arginine, isoleucine, or methionine, residue 387 is substituted with arginine, proline, histidine, serine, threonine, or alanine, and/or residue 389 is substituted with proline, serine or asparagine. In more specific embodiments, residues at one or more positions 385, 386, 387, and 389 are substituted with arginine, threonine, arginine, and proline, respectively. In yet another specific embodiment, residues at one or more positions 385, 386, and 389 are substituted with aspartic acid, proline, and serine, respectively.

In particular embodiments, amino acid modifications are made at one or a combination of residues 251, 252, 254, 255, 256, 308, 309, 311, 312, 314, 385, 386, 387, 389, 428, 433, 434, and/or 436, particularly where the modifications are one or more of the amino acid substitutions described immediately above for these residues.

In a preferred embodiment, the molecule of the invention contains a Fc region, or FcRn-binding domain thereof, having one or more of the following substitutions: leucine at residue 251, tyrosine at residue 252, threonine or serine at residue 254, arginine at residue 255, threonine at residue 308, proline at residue 309, serine at residue 311, aspartic acid at residue 312, leucine at residue 314, arginine at residue 385, threonine at residue 386, arginine at residue 387, proline at residue 389, methionine at residue 428, and/or tyrosine at residue 434.

In a preferred embodiment, the FcRn binding domain has a substitution at 1, 2, 3, 4, 5, 6, 7, 8, 9, 10, 12, 14, 16 or all 18 of residues 251, 252, 254, 255, 256, 308, 309, 311, 312, 314, 385, 386, 387, 389, 428, 433, 434, and/or 436.

Amino acid modifications can be made by any method known in the art and many such methods are well known and routine for the skilled artisan. For example, but not by way of limitation, amino acid substitutions, deletions and insertions may be accomplished using any well-known PCR-based technique. Amino acid substitutions may be made by site-directed mutagenesis (see, for example, Zoller and Smith, *Nucl. Acids Res.* 10:6487–6500, 1982; Kunkel, *Proc. Natl. Acad. Sci USA* 82:488, 1985, which are hereby incorporated by reference in their entireties). Mutants that result in increased affinity for FcRn and increased in vivo half-life may readily be screened using well-known and routine assays, such as those described in Section 5.11, infra. In a preferred method, amino acid substitutions are introduced at one or more residues in the IgG constant domain or FcRn-binding fragment thereof and the mutated constant domains or fragments are expressed on the surface of bacteriophage which are then screened for increased FcRn binding affinity (see, in particular, Section 5.2 and 5.11, infra).

Preferably, the amino acid residues to be modified are surface exposed residues. Additionally, in making amino acid substitutions, preferably the amino acid residue to be substituted is a conservative amino acid substitution, for example, a polar residue is substituted with a polar residue, a hydrophilic residue with a hydrophilic residue, hydrophobic residue with a hydrophobic residue, a positively charged residue with a positively charged residue, or a negatively charged residue with a negatively charged residue. Moreover, preferably, the amino acid residue to be modified is not highly or completely conserved across species and/or is critical to maintain the constant domain tertiary structure or to FcRn binding. For example, but not by way of limitation, modification of the histidine at residue 310 is not preferred.

Specific mutants of the Fc domain that have increased affinity for FcRn were isolated after the third-round panning (as described in Section 6) from a library of mutant human IgG1 molecules having mutations at residues 308–314 (histidine at position 310 and tryptophan at position 313 are fixed), those isolated after the fifth-round panning of the library for residues 251–256 (isoleucine at position 253 is fixed), those isolated after fourth-round panning of the library for residues 428–436 (histidine at position 429, glutamic acid at position 430, alanine at position 431, leucine at position 432, and histidine at position 435 are fixed), and those isolated after sixth-round panning of the library for residues 385–389 (glutamic acid at position 388 is fixed) are listed in Table I. The wild type human IgG1 has a sequence Val-Leu-His-Gln-Asp-Trp-Leu (SEQ ID NO:86) at positions 308–314, Leu-Met-Ile-Ser-Arg-Thr (SEQ ID NO:87) at positions 251–256, Met-His-Glu-Ala-Leu-His-Asn-His-Tyr (SEQ ID NO:88) at positions 428–436, and Gly-Gln-Pro-Glu-Asn (SEQ ID NO:89) at positions 385–389.

TABLE I

MUTANTS ISOLATED BY PANNING

| LIBRARY | MUTANTS* | |
|---|---|---|
| 251–256 | Leu Tyr Ile Thr Arg Glu | (SEQ ID NO:90) |
| | Leu *Tyr* Ile Ser Arg Thr | (SEQ ID NO:91) |
| | Leu *Tyr* Ile Ser Arg *Ser* | (SEQ ID NO:92) |
| | Leu *Tyr* Ile Ser Arg *Arg* | (SEQ ID NO:93) |
| | Leu *Tyr* Ile Ser Arg *Gln* | (SEQ ID NO:94) |
| | Leu *Trp* Ile Ser Arg Thr | (SEQ ID NO:95) |
| | Leu Tyr Ile Ser Leu Gln | (SEQ ID NO:96) |
| | Leu Phe Ile Ser Arg Asp | (SEQ ID NO:97) |
| | Leu Phe Ile Ser Arg Thr | (SEQ ID NO:98) |
| | Leu Phe Ile Ser Arg Arg | (SEQ ID NO:99) |
| | Leu Phe Ile Thr Gly Ala | (SEQ ID NO:100) |
| | Leu Ser Ile Ser Arg Glu | (SEQ ID NO:101) |
| | Arg Thr Ile Ser Ile Ser | (SEQ ID NO:102) |
| 308–314 | Thr Pro His Ser Asp Trp Leu | (SEQ ID NO:103) |
| | Ile Pro His Glu Asp Trp Leu | (SEQ ID NO:104) |
| 385–389 | Arg Thr Arg Glu Pro | (SEQ ID NO:105) |
| | *Asp Pro* Pro Glu *Ser* | (SEQ ID NO:106) |
| | Ser Asp Pro Glu Pro | (SEQ ID NO:107) |
| | Thr Ser His Glu Asn | (SEQ ID NO:108) |
| | Ser Lys Ser Glu Asn | (SEQ ID NO:109) |

TABLE I-continued

MUTANTS ISOLATED BY PANNING

| LIBRARY | MUTANTS* | |
|---|---|---|
| | His Arg Ser Glu Asn | (SEQ ID NO:110) |
| | Lys Ile Arg Glu Asn | (SEQ ID NO:111) |
| | Gly Ile Thr Glu Ser | (SEQ ID NO:112) |
| | Ser Met Ala Glu Pro | (SEQ ID NO:113) |
| 428–436 | Met His Glu Ala Leu *Arg* *Tyr* *His* *His* | (SEQ ID NO:114) |
| | Met His Glu Ala Leu His Phe His His | (SEQ ID NO:115) |
| | Met His Glu Ala Leu Lys Phe His His | (SEQ ID NO:116) |
| | Met His Glu Ala Leu Ser Tyr His Arg | (SEQ ID NO:117) |
| | Thr His Glu Ala Leu His Tyr His Thr | (SEQ ID NO:118) |
| | Met His Glu Ala Leu His Tyr His Tyr | (SEQ ID NO:119) |

*Substituting residues are indicated in bold face

The underlined sequences in Table I correspond to sequences that occurred 10 to 20 times in the final round of panning and the sequences in italics correspond to sequences that occurred 2 to 5 times in the final round of panning. Those sequences that are neither underlined nor italicized occurred once in the final round of panning.

In one preferred embodiment, the invention provides modified immunoglobulin molecules (e.g., various antibodies) that have increased in vivo half-life and affinity for FcRn relative to unmodified molecules (and, in preferred embodiments, altered bioavailabilty such as increased or decreased transport to mucosal surfaces or other target tissues). Such immunoglobulin molecules include IgG molecules that naturally contain an FcRn binding domain and other non-IgG immunoglobulins (e.g., IgE, IgM, IgD, IgA and IgY) or fragments of immunoglobulins that have been engineered to contain an FcRn-binding fragment (i. e., fusion proteins comprising non-IgG immunoglobulin or a portion thereof and an FcRn binding domain). In both cases the FcRn-binding domain has one or more amino acid modifications that increase the affinity of the constant domain fragment for FcRn.

The modified immunoglobulins include any immunoglobulin molecule that binds (preferably, immunospecifically, i.e., competes off non-specific binding), as determined by immunoassays well known in the art for assaying specific antigen-antibody binding) an antigen and contains an FcRn-binding fragment. Such antibodies include, but are not limited to, polyclonal, monoclonal, bi-specific, multi-specific, human, humanized, chimeric antibodies, single chain antibodies, Fab fragments, F(ab')$_2$ fragments, disulfide-linked Fvs, and fragments containing either a VL or VH domain or even a complementary determining region (CDR) that specifically binds an antigen, in certain cases, engineered to contain or fused to an FcRn binding domain.

The IgG molecules of the invention, and FcRn-binding fragments thereof, are preferably IgG1 subclass of IgGs, but may also be any other IgG subclasses of given animals. For example, in humans, the IgG class includes IgG1, IgG2, IgG3, and IgG4; and mouse IgG includes IgG1, IgG2a, IgG2b, IgG2c and IgG3. It is known that certain IgG subclasses, for example, mouse IgG2b and IgG2c, have higher clearance rates than, for example, IgG1 (Medesan et al., Eur. J. Immunol., 28:2092–2100, 1998). Thus, when using IgG subclasses other than IgG1, it may be advantageous to substitute one or more of the residues, particularly in the CH2 and CH3 domains, that differ from the IgG1 sequence with those of IgG1, thereby increasing the in vivo half-life of the other types of IgG.

The immunoglobulins (and other proteins used herein) may be from any animal origin including birds and mammals. Preferably, the antibodies are human, rodent (e.g., mouse and rat), donkey, sheep, rabbit, goat, guinea pig, camel, horse, or chicken. As used herein, "human" antibodies include antibodies having the amino acid sequence of a human immunoglobulin and include antibodies isolated from human immunoglobulin libraries or from animals transgenic for one or more human immunoglobulin and that do not express endogenous immunoglobulins, as described infra and, for example, in U.S. Pat. No. 5,939,598 by Kucherlapati et al.

The antibodies of the present invention may be mono-specific, bispecific, trispecific or of greater multispecificity. Multispecific antibodies may be specific for different epitopes of a polypeptide or may be specific for heterologous epitopes, such as a heterologous polypeptide or solid support material. See, e.g., PCT publications WO 93/17715, WO 92/08802; WO 91/00360; WO 92/05793; Tutt, et al., J. Immunol., 147:60–69, 1991; U.S. Pat. Nos. 4,474,893; 4,714,681; 4,925,648; 5,573,920; 5,601,819; Kostelny et al., J. Immunol., 148:1547–1553, 1992.

The antibodies of the invention include derivatives that are otherwise modified, i.e., by the covalent attachment of any type of molecule to the antibody such that covalent attachment does not prevent the antibody from binding antigen and/or generating an anti-idiotypic response. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to, specific chemical cleavage, acetylation, formylation, metabolic synthesis of tunicamycin, etc. Additionally, the derivative may contain one or more non-classical amino acids.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, (Cold Spring Harbor Laboratory Press, 2nd ed. 1988); Hammerling, et al., in: Monoclonal Antibodies and T-Cell Hybridomas, pp. 563–681 (Elsevier, N.Y., 1981) (both of which are incorporated herein by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well known in the art. In a non-limiting example, mice can be immunized with an antigen of interest or a cell expressing such an antigen. Once an immune response is detected, e.g., antibodies specific for the antigen are detected in the mouse serum, the mouse spleen is harvested and splenocytes isolated. The splenocytes are then fused by well known techniques to any suitable myeloma cells. Hybridomas are selected and cloned by limiting dilution. The hybridoma clones are then assayed by methods known in the art for cells that secrete antibodies capable of binding the antigen. Ascites fluid, which generally contains high levels of antibodies, can be generated by inoculating mice intraperitoneally with positive hybridoma clones.

Antibody fragments which recognize specific epitopes may be generated by known techniques. For example, Fab and F(ab')$_2$ fragments may be produced by proteolytic cleavage of immunoglobulin molecules, using enzymes such as papain (to produce Fab fragments) or pepsin (to produce F(ab')$_2$ fragments). F(ab')$_2$ fragments contain the complete light chain, and the variable region, the CH1 region and the hinge region of the heavy chain.

For example, antibodies can also be generated using various phage display methods known in the art. In phage display methods, functional antibody domains are displayed on the surface of phage particles which carry the polynucleotide sequences encoding them. In a particular embodiment, such phage can be utilized to display antigen binding domains, such as Fab and Fv or disulfide-bond stabilized Fv, expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage, including fd and M13. The antigen binding domains are expressed as a recombinantly fused protein to either the phage gene III or gene VIII protein. Alternatively, the modified FcRn binding portion of immunoglobulins of the present invention can be also expressed in a phage display system. Examples of phage display methods that can be used to make the immunoglobulins, or fragments thereof, of the present invention include those disclosed in Brinkman et al., *J. Immunol. Methods*, 182:41–50, 1995; Ames et al., *J. Immunol. Methods*, 184:177–186, 1995; Kettleborough et al., *Eur. J. Immunol.*, 24:952–958, 1994; Persic et al., *Gene*, 187:9–18, 1997; Burton et al., *Advances in Immunology*, 57:191–280, 1994; PCT application No. PCT/GB91/01134; PCT publications WO 90/02809; WO 91/10737; WO 92/01047; WO 92/18619; WO 93/1 1236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies, including human antibodies, or any other desired fragments, and expressed in any desired host, including mammalian cells, insect cells, plant cells, yeast, and bacteria, e.g., as described in detail below. For example, techniques to recombinantly produce Fab, Fab' and F(ab')$_2$ fragments can also be employed using methods known in the art such as those disclosed in PCT publication WO 92/22324; Mullinax et al., *BioTechniques*, 12(6):864–869, 1992; and Sawai et al., *AJRI*, 34:26–34, 1995; and Better et al., *Science*, 240: 1041–1043, 1988 (each of which is incorporated by reference in its entirety). Examples of techniques which can be used to produce single-chain Fvs and antibodies include those described in U.S. Pat. Nos. 4,946,778 and 5,258,498; Huston et al., *Methods in Enzymology*, 203:46–88, 1991; Shu et al., *PNAS*, 90:7995–7999, 1993; and Skerra et al., *Science*, 240:1038–1040, 1988.

For some uses, including in vivo use of antibodies in humans and in vitro detection assays, it may be preferable to use chimeric, humanized, or human antibodies. A chimeric antibody is a molecule in which different portions of the antibody are derived from different animal species, such as antibodies having a variable region derived from a murine monoclonal antibody and a constant region derived from a human immunoglobulin. Methods for producing chimeric antibodies are known in the art. See e.g., Morrison, *Science*, 229:1202, 1985; Oi et al., *BioTechniques*, 4:214 1986; Gillies et al., *J. Immunol. Methods*, 125:191–202, 1989; U.S. Pat. Nos. 5,807,715; 4,816,567; and 4,816,397, which are incorporated herein by reference in their entireties. Humanized antibodies are antibody molecules from non-human species that bind the desired antigen having one or more complementarity determining regions (CDRs) from the non-human species and framework regions from a human immunoglobulin molecule. Often, framework residues in the human framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. See, e.g., Queen et al., U.S. Pat. No. 5,585,089; Riechmann et al., *Nature*, 332:323, 1988, which are incorporated herein by reference in their entireties. Antibodies can be humanized using a variety of techniques known in the art including, for example, CDR-grafting (EP 239,400; PCT publication WO 91/09967; U.S. Pat. Nos. 5,225,539; 5,530,101 and 5,585,089), veneering or resurfacing (EP 592,106; EP 519,596; Padlan, *Molecular Immunology*, 28(4/5):489–498, 1991; Studnicka et al., *Protein Engineering*, 7(6):805–814, 1994; Roguska et al., *Proc Natl. Acad. Sci. USA*, 91:969–973, 1994), and chain shuffling (U.S. Pat. No. 5,565,332), all of which are hereby incorporated by reference in their entireties.

Completely human antibodies are particularly desirable for therapeutic treatment of human patients. Human antibodies can be made by a variety of methods known in the art including phage display methods described above using antibody libraries derived from human immunoglobulin sequences. See U.S. Pat. Nos. 4,444,887 and 4,716,111; and PCT publications WO 98/46645; WO 98/50433; WO 98/24893; WO 98/16654; WO 96/34096; WO 96/33735; and WO 91/10741, each of which is incorporated herein by reference in its entirety.

Human antibodies can also be produced using transgenic mice which are incapable of expressing functional endogenous immunoglobulins, but which can express human immunoglobulin genes. For an overview of this technology for producing human antibodies, see Lonberg and Huszar, *Int. Rev. Immunol.*, 13:65–93, 1995. For a detailed discussion of this technology for producing human antibodies and human monoclonal antibodies and protocols for producing such antibodies, see, e.g., PCT publications WO 98/24893; WO 92/01047; WO 96/34096; WO 96/33735; European Patent No.0 598 877; U.S. Pat. Nos. 5,413,923; 5,625,126; 5,633,425; 5,569,825; 5,661,016; 5,545,806; 5,814,318; 5,885,793; 5,916,771; and 5,939,598, which are incorporated by reference herein in their entireties. In addition, companies such as Abgenix, Inc. (Freemont, Calif.), Medarex (NJ) and Genpharm (San Jose, Calif.) can be engaged to provide human antibodies directed against a selected antigen using technology similar to that described above.

Completely human antibodies which recognize a selected epitope can be generated using a technique referred to as "guided selection." In this approach a selected non-human mono clonal antibody, e.g., a mouse antibody, is used to guide the selection of a completely human antibody recognizing the same epitope. (Jespers et al., *Bio/technology*, 12:899–903, 1988).

In particular embodiments, the modified antibodies have in vivo therapeutic and/or prophylactic uses. Examples of therapeutic and prophylactic antibodies which may be so modified include, but are not limited to, SYNAGIS® (MedImmune, MD) which is a humanized anti-respiratory syncytial virus (RSV) monoclonal antibody for the treatment of patients with RSV infection; HERCEPTIN® (Trastuzumab) (Genentech, CA) which is a humanized anti-HER2 monoclonal antibody for the treatment of patients with metastatic breast cancer; REMICADE® (infliximab) (Centocor, PA) which is a chimeric anti-TNFα monoclonal antibody for the treatment of patients with Crone's disease; REOPRO® (abciximab) (Centocor) which is an anti-glycoprotein IIb/IIIa receptor on the platelets for the prevention of clot formation; ZENAPAX® (daclizumab) (Roche Pharmaceuticals, Switzerland) which is an immunosuppressive, humanized anti-CD25 monoclonal antibody for the prevention of acute renal allograft rejection. Other examples are a humanized anti-CD 18 F(ab')$_2$ (Genentech); CDP860 which is a humanized anti-CD18 F(ab')$_2$ (Celltech, UK); PRO542 which is an anti-HIV gp120 antibody fused with CD4 (Progenics/Genzyme Transgenics); Ostavir which is a human anti Hepatitis B virus antibody (Protein Design Lab/Novartis); PROTOVIR™ which is a humanized anti-CMV IgG1 antibody (Protein Design Lab/Novartis); MAK-195 (SEGARD) which is a murine anti-TNF-α F(ab')$_2$ (Knoll Pharma/BASF); IC14 which is an anti-CD14 antibody (ICOS Pharm); a humanized anti-VEGF IgG1 antibody (Genentech); OVAREX™ which is a murine anti-CA 125 antibody (Altarex); PANOREX™ which is a murine anti-17-IA cell surface antigen IgG2a antibody (Glaxo Wellcome/Centocor); BEC2 which is a murine anti-idiotype (GD3 epitope) IgG antibody (ImClone System); IMC-C225 which is a chimeric anti-EGFR IgG antibody (ImClone System); VITAXIN™ which is a humanized anti-αVβ3 integrin antibody (Applied Molecular Evolution/MedImmune); Campath 1H/LDP-03 which is a humanized anti CD52 IgG1 antibody (Leukosite); Smart M195 which is a humanized anti-CD33 IgG antibody (Protein Design Lab/Kanebo); RITUXANT™ which is a chimeric anti-CD20 IgG1 antibody (IDEC Pharm/Genentech, Roche/Zettyaku); LYMPHOCIDE™ which is a humanized anti-CD22 IgG antibody (Immunomedics); Smart ID10 which is a humanized anti-HLA antibody (Protein Design Lab); ONCOLYM™ (Lym-1) is a radiolabelled murine anti-HLA DIAGNOSTIC REAGENT antibody (Techniclone); ABX-IL8 is a human anti-IL8 antibody (Abgenix); anti-CD11a is a humanized IgG1 antibody (Genetech/Xoma); ICM3 is a humanized anti-ICAM3 antibody (ICOS Pharm); IDEC-114 is a primatized anti-CD80 antibody (IDEC Pharm/Mitsubishi); ZEVALIN™ is a radiolabelled murine anti-CD20 antibody (IDEC/Schering AG); IDEC-131 is a humanized anti-CD40L antibody (IDEC/Eisai); IDEC-151 is a primatized anti-CD4 antibody (IDEC); IDEC-152 is a primatized anti-CD23 antibody (IDEC/Seikagaku); SMART anti-CD3 is a humanized anti-CD3 IgG (Protein Design Lab); 5G1.1 is a humanized anti-complement factor 5 (C5) antibody (Alexion Pharm); D2E7 is a humanized anti-TNF-α antibody (CAT/BASF); CDP870 is a humanized anti-TNF-α Fab fragment (Celltech); IDEC-151 is a primatized anti-CD4 IgG1 antibody (IDEC Pharm/SmithKline Beecham); MDX-CD4 is a human anti-CD4 IgG antibody (Medarex/Eisai/Genmab); CDP571 is a humanized anti-TNF-α IgG4 antibody (Celltech); LDP-02 is a humanized anti-α4β7 antibody (LeukoSite/Genentech); OrthoClone OKT4A is a humanized anti-CD4 IgG antibody (Ortho Biotech); ANTOVA™ is a humanized anti-CD40L IgG antibody (Biogen); ANTEGREN™ is a humanized anti-VLA-4 IgG antibody (Elan); MDX-33 is a human anti-CD64 (FcγR) antibody (Medarex/Centeon); SCH55700 is a humanized anti-IL-5 IgG4 antibody (Celltech/Schering); SB-240563 and SB-240683 are humanized anti-IL-5 and IL-4 antibodies, respectively, (SmithKline Beecham); rhuMab-E25 is a humanized anti-IgE IgG1 antibody (Genentech/Norvartis/Tanox Biosystems); IDEC-152 is a primatized anti-CD23 antibody (IDEC Pharm); ABX-CBL is a murine anti CD-147 IgM antibody (Abgenix); BTI-322 is a rat anti-CD2 IgG antibody (Medimmune/Bio Transplant); Orthoclone/OKT3 is a murine anti-CD3 IgG2a antibody (ortho Biotech); SIMULECT™ is a chimeric anti-CD25 IgG1 antibody (Novartis Pharm); LDP-01 is a humanized anti-β$_2$-integrin IgG antibody (LeukoSite); Anti-LFA-1 is a murine anti CD18 F(ab')$_2$ (Pasteur-Merieux/Immunotech); CAT-152 is a human anti-TGF-β$_2$ antibody (Cambridge Ab Tech); and Corsevin M is a chimeric anti-Factor VII antibody (Centocor).

In specific embodiments, the invention provides modified antibodies having one or more of the mutations described herein and that immunospecifically bind RSV, e.g., SYNAGIS®. The present invention also provides modified antibodies having one or more of the mutations described herein and that comprise a variable heavy (VH) and/or variable light (VL) domain having the amino acid sequence of any VH and/or VL domain listed in Table III. The present invention further encompasses anti-RSV antibodies comprising one or more VH complementarity determining regions (CDRs) and/or one or more VL CDRs having the amino acid sequence of one or more VH CDRs and/or VL CDRS listed in Table III or one or more of the CDRs listed in Table II wherein one or more of the bolded and underlined residues has an amino acid substitution, preferably that increases the affinity of the antibody for RSV. In specific embodiments, the antibody to be modified is AFFF, p12f2, p12f4, p11d4, Ale109, A12a6, A13c4, A17d4, A4B4, A8C7, 1X-493L1FR, H3-3F4, M3H9, Y10H6, DG, AFFF(1), 6H8, L1-7E5, L215B10, A13A11, A1H5, A4B4(1), A4B4L1FR-S28R, A4B4-F52S.

TABLE II

CDR Sequences of SYNAGIS ®

| CDR | Sequence | SEQ ID NO: |
|---|---|---|
| VH1 | TSGMSVG | 1 |
| VH2 | DIWWDDDKKDYNPSLKS | 2 |
| VH3 | SMITNWYFDV | 3 |
| VL1 | KCQLSVGYMH | 4 |
| VL2 | DTSKLAS | 5 |
| VL3 | FQGSGYPFT | 6 |

TABLE III

ANTI-RSV ANTIBODIES

| Antibody Name | VH Domain | VH CDR1 | VH CDR2 | VH CDR3 | VL Domain | VL CDR1 | VL CDR2 | VL CDR3 |
|---|---|---|---|---|---|---|---|---|
| SYNAGIS | SEQ ID NO:7 | TSGMSVG (SEQ ID NO:1) | DIWWDDKKDYNPSLKS (SEQ ID NO:2) | SMITNWYFDV (SEQ ID NO:3) | SEQ ID NO:8 | KCQLSVGYMH (SEQ ID NO:4) | DTSKLAS (SEQ ID NO:5) | FQGSGYPFT (SEQ ID NO:6) |
| AFFF | SEQ ID NO:9 | TAGMSVG (SEQ ID NO:10) | DIWWDDKKDYNPSLKS (SEQ ID NO:2) | SMITNFYFDV (SEQ ID NO:12) | SEQ ID NO:13 | SASSSVGYMH (SEQ ID NO:14) | DTFKLAS (SEQ ID NO 15) | FQFSGYPFT (SEQ ID NO:16) |
| p12f2 | SEQ ID NO:17 | TPCMSVG (SEQ ID NO.18) | DIWWDDKKDYNPSLKS (SEQ ID NO:2) | DMIFNFYFDV (SEQ ID NO:20) | SEQ ID NO.21 | SLSSRVGYMH (SEQ ID NO:22) | DTFYLSS (SEQ ID NO:23) | FQGSGYPFT (SEQ ID NO:6) |
| p12f4 | SEQ ID NO.24 | TPGMSVG (SEQ ID NO.18) | DIWWDGKKHYNPSLD (SEQ ID NO:19) | DMIFNFYFDV (SEQ ID NO:20) | SEQ ID NO.26 | SLSSRVGYMH (SEQ ID NO:22) | DTRGLPS (SEQ ID NO:27) | FQGSGYPFT (SEQ ID NO:6) |
| p11d4 | SEQ ID NO:28 | TPGMSVG (SEQ ID NO.18) | DIWWDGKKHYNPSLKD (SEQ ID NO:25) | DMIFNWYFDV (SEQ ID NO:29) | SEQ ID NO:30 | SPSSRVGYMH (SEQ ID NO:31) | DTMRLAS (SEQ ID NO:32) | FQGSGYPFT (SEQ ID NO:6) |
| Ale109 | SEQ ID NO.33 | TAGMSVG (SEQ ID NO:10) | DIWWDGKKHYNPSLKD (SEQ ID NO:25) | DMIFNWYFDV (SEQ ID NO:29) | SEQ ID NO:34 | SLSSRVGYMH (SEQ ID NO:22) | DTFKLSS (SEQ ID NO.35) | FQGSGYPFT (SEQ ID NO:6) |
| A12a6 | SEQ ID NO.36 | TAGMSVG (SEQ ID NO:10) | DIWWDGKKHYNPSLKD (SEQ ID NO:37) | DMIFNFYFDV (SEQ ID NO:20) | SEQ ID NO 38 | SASSRVGYMH (SEQ ID NO:39) | DTFKLSS (SEQ ID NO:35) | FQGSGYPFT (SEQ ID NO:6) |
| A13c4 | SEQ ID NO:40 | TAGMSVG (SEQ ID NO:10) | DIWWDGKKSYNPSLKD (SEQ ID NO:41) | DMIFNFYFDV (SEQ ID NO:20) | SEQ ID NO:42 | SLSSRVGYMH (SEQ ID NO:22) | DTMYQSS (SEQ ID NO:43) | FQGSGYPFT (SEQ ID NO:6) |
| A17d4 | SEQ ID NO:44 | TAGMSVG (SEQ ID NO:10) | DIWWDGKKSYNPSLKD (SEQ ID NO:45) | DMIFNFYFDV (SEQ ID NO:20) | SEQ ID NO:46 | LPSSRVGYMH (SEQ ID NO:47) | DTMYQSS (SEQ ID NO:43) | FQGSGYPFT (SEQ ID NO:6) |
| A4B4 | SEQ ID NO:48 | TAGMSVG (SEQ ID NO:10) | DIWWDDKKHYNPSLKS (SEQ ID NO:19) | DMIFNFYFDV (SEQ ID NO:20) | SEQ ID NO:49 | SASSRVGYMH (SEQ ID NO:39) | DTFFLDS (SEQ ID NO:50) | FQGSGYPFT (SEQ ID NO:6) |
| A8C7 | SEQ ID NO:51 | TAGMSVG (SEQ ID NO:10) | DIWWDGKKHYNPSLKD (SEQ ID NO:45) | DMIFNWYFDV (SEQ ID NO:29) | SEQ ID NO:52 | SPSSRVGYMH (SEQ ID NO:31) | DTRYQSS (SEQ ID NO:53) | FQGSGYPFT (SEQ ID NO:6) |
| 1X-493L1FR | SEQ ID NO:7 | TSGMSVG (SEQ ID NO:1) | DIWWDDKKDYNPSLKS (SEQ ID NO:2) | SMITNWYFDV (SEQ ID NO:3) | SEQ ID NO:54 | SASSSVGYMH (SEQ ID NO:14) | DTSKLAS (SEQ ID NO:5) | FQGSGYPFT (SEQ ID NO:6) |
| H3-3F4 | SEQ ID NO.55 | TAGMSVG (SEQ ID NO:10) | DIWWDDKKDYNPSLKS (SEQ ID NO:2) | DMIFNWYFDV (SEQ ID NO:29) | SEQ ID NO:56 | SASSSVGYMH (SEQ ID NO:14) | DTFKLAS (SEQ ID NO:15) | FQGSGYPFT (SEQ ID NO:6) |
| M3H9 | SEQ ID NO.55 | TAGMSVG (SEQ ID NO:10) | DIWWDDKKDYNPSLKS (SEQ ID NO:2) | DMIFNWYFDV (SEQ ID NO:29) | SEQ ID NO:56 | SASSSVGYMH (SEQ ID NO:14) | DTYKQTS (SEQ ID NO:57) | FQGSGYPFT (SEQ ID NO:6) |
| Y10H6 | SEQ ID NO.55 | TAGMSVG (SEQ ID NO:10) | DIWWDDKKDYNPSLKS (SEQ ID NO 2) | DMIFNWYFDV (SEQ ID NO:29) | SEQ ID NO:58 | SASSSVGYMH (SEQ ID NO:14) | DTRYLSS (SEQ ID NO:59) | FQGSGYPFT (SEQ ID NO:6) |
| DG | SEQ ID NO 78 | TAGMSVG (SEQ ID NO:10) | DIWWDDKKDYNPSLKS (SEQ ID NO:2) | DMITNFYFDV (SEQ ID NO:79) | SEQ ID NO:56 | SASSSVGYMH (SEQ ID NO:14) | DTFKLAS (SEQ ID NO:15) | FQGSGYPFT (SEQ ID NO:6) |

TABLE III-continued

ANTI-RSV ANTIBODIES

| Antibody Name | VH Domain | VH CDR1 | VH CDR2 | VH CDR3 | VL Domain | VL CDR1 | VL CDR2 | VL CDR3 |
|---|---|---|---|---|---|---|---|---|
| AFFF(1) | SEQ ID NO:9 | TAGMSVG (SEQ ID NO:10) | DIWWDDKKDYNPSLKS (SEQ ID NO:2) | SMITNFYPDV (SEQ ID NO:12) | SEQ ID NO:60 | SASSSVGYMH (SEQ ID NO:14) | DTFKLAS (SEQ ID NO:15) | FQGSFYPFT (SEQ ID NO:61) |
| 6H8 | SEQ ID NO:78 | TAGMSVG (SEQ ID NO:10) | DIWWDDKKDYNPSLKS (SEQ ID NO:2) | DMITNFYPDV (SEQ ID NO:79) | SEQ ID NO:62 | SASSSVGYMH (SEQ ID NO:14) | DTFKLTS (SEQ ID NO:63) | FQGSGYPFT (SEQ ID NO:6) |
| L1-7E5 | SEQ ID NO:78 | TAGMSVG (SEQ ID NO:10) | DIWWDDKKDYNPSLKS (SEQ ID NO:2) | DMITNFYPDV (SEQ ID NO:79) | SEQ ID NO:64 | SASSRVGYMH (SEQ ID NO:39) | DTFKLAS (SEQ ID NO:15) | FQGSGYPFT (SEQ ID NO:6) |
| L215B10 | SEQ ID NO:78 | TAGMSVG (SEQ ID NO:10) | DIWWDDKKDYNPSLKS (SEQ ID NO:2) | DMITNFYPDV (SEQ ID NO:79) | SEQ ID NO:65 | SASSSVGYMH (SEQ ID NO:14) | DTFRLAS (SEQ ID NO:66) | FQGSGYPFT (SEQ ID NO:6) |
| A13A11 | SEQ ID NO:67 | TAGMSVG (SEQ ID NO:10) | DIWWDDKKHYNPSLKD (SEQ ID NO:19) | DMIFNWYPDV (SEQ ID NO 29) | SEQ ID NO:68 | SPSSRVGYMH (SEQ ID NO.31) | DTYRHSS (SEQ ID NO:69) | FQGSGYPFT (SEQ ID NO:6) |
| A1H5 | SEQ ID NO:70 | TAGMSVG (SEQ ID NO:10) | DIWWDGKKHYNPSLKD (SEQ ID NO:25) | DMIFNWYPDV (SEQ ID NO:29) | SEQ ID NO:71 | SLSSSVGYMH (SEQ ID NO:72) | DTFFHRS (SEQ ID NO:73) | FQGSGYPFT (SEQ ID NO:6) |
| A4B4(1) | SEQ ID NO 48 | TAGMSVG (SEQ ID NO:10) | DIWWDDKKHYNPSLKD (SEQ ID NO 19) | DMIFNYPDV (SEQ ID NO:20) | SEQ ID NO:74 | SASSRVGYMH (SEQ ID NO.39) | DTLLLDS (SEQ ID NO:75) | FQGSGYPFT (SEQ ID NO:6) |
| A4B4L1FR-S28R | SEQ ID NO 48 | TAGMSVG (SEQ ID NO:10) | DIWWDDKKHYNPSLKD (SEQ ID NO:19) | DMIFNYPDV (SEQ ID NO:20) | SEQ ID NO 11 | SASSRVGYMH (SEQ ID NO.39) | DTSKLAS (SEQ ID NO:5) | FQGSGYPFT (SEQ ID NO:6) |
| A4B4-F52S | SEQ ID NO:48 | TAGMSVG (SEQ ID NO:10) | DIWWDDKKHYNPSLKD (SEQ ID NO:19) | DMIFNYPDV (SEQ ID NO:20) | SEQ ID NO:76 | SASSRVGYMH (SEQ ID NO:39) | DTSFLDS (SEQ ID NO:77) | FQGSGYPFT (SEQ ID NO:6) |

In other embodiments, the antibody is a modified anti-α$_v$β$_3$ antibody, preferably a Vitaxin antibody (see, PCT publications WO 98/33919 and WO 00/78815, both by Huse et al., and both of which are incorporated by reference herein in their entireties). Modified IgGs of the present invention having longer half-lives than wild type may also include IgGs whose bioactive sites, such as antigen-binding sites, Fc-receptor binding sites, or complement-binding sites, are modified by genetic engineering to increase or reduce such activities compared to the wild type.

Modification of these and other therapeutic antibodies to increase the in vivo half-life permits administration of lower effective dosages and/or less frequent dosing of the therapeutic antibody. Such modification to increase in vivo half-life can also be useful to improve diagnostic immunoglobulins as well, for example, permitting administration of lower doses to achieve sufficient diagnostic sensitivity.

The present invention also provides fusion proteins comprising a bioactive molecule and an hinge-Fc region or a fragment thereof (preferably human) having one or more modifications (i.e., substitutions, deletions, or insertions) in amino acid residues identified to be involved in the interaction between the hinge-Fc region and the FcRn receptor. In particular, the present invention provides fusion proteins comprising a bioactive molecule recombinantly fused or chemically conjugated (including both covalent and non-covalent conjugations) to a CH2 domain having one or more modifications in amino acid residues 251–256, 285–290, and/or amino acid residues 308–314, and/or to a CH3 domain having one or more modifications in amino acid residues 385–389 and/or 428–436, in particular, one or more of the amino acid substitutions discussed above. The fusion of a bioactive molecule to a constant domain or a fragment thereof with one or more of such modifications increases the in vivo half-life of the bioactive molecule.

In a preferred embodiment, fusion proteins of the invention comprise a bioactive molecule recombinantly fused or chemically conjugated to a CH2 domain having one or more amino acid residue substitutions in amino acid residues 251–256, 285–290, and/or amino acid residues 308–314, and/or to a CH3 domain having one or more modifications in amino acid residues 385–389 and/or 428–436. In certain embodiments, a fusion protein comprises a CH2 domain of IgG molecule in which amino acid residues 253, 310, and 313 are not modified. In another embodiments, a fusion protein comprises a CH3 domain of IgG molecule in which amino acid residues 388, 429, 430, 431, 432, and 435 are not modified.

A bioactive molecule can be any polypeptide or synthetic drug known to one of skill in the art. Preferably, a bioactive molecule is a polypeptide consisting of at least 5, preferably at least 10, at least 20, at least 30, at least 40, at least 50, at least 60, at least 70, at least 80, at least 90 or at least 100 amino acid residues. Examples of bioactive polypeptides include, but are not limited to, various types of antibodies, cytokines (e.g., IL-2, IL-3, IL-4, IL-5, IL-6, IL-7, IL-10, IL-12, IL-15, IFN-γ, IFN-α, and IFN-β), cell adhesion molecules (e.g., CTLA4, CD2, and CD28), ligands (e.g., TNF-α, TNF-β, and an anti-angiogenic factor such as endostatin), receptors, antibodies and growth factors (e.g., PDGF, EGF, NGF, and KGF).

A bioactive molecule can also be a therapeutic moiety such as a cytotoxin (e.g., a cytostatic or cytocidal agent), a therapeutic agent or a radioactive element (e.g., alpha-emitters, gamma-emitters, etc.). Examples of cytostatic or cytocidal agents include, but are not limited to, paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cisdichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The present invention also provides polynucleotides comprising a nucleotide sequence encoding a modified IgG of the invention and fragments thereof which contain the modified FcRn binding sites with increased affinity and vectors comprising said polynucleotides. Furthermore, the invention includes polynucleotides that hybridize under stringent or lower stringent hybridization conditions to polynucleotides encoding modified IgGs of the present invention.

The nucleotide sequence of modified IgGs and the polynucleotides encoding the same may be obtained by any methods known in the art, including general DNA sequencing method, such as dideoxy chain termination method (Sanger sequencing), and oligonucleotide priming in combination with PCR, respectively.

5.2. Identification of Mutations within the Hinge-Fc Region of Immunoglobulin Molecules One or more modifications in amino acid residues 251–256, 285–290, 308–314, 385–389, and 428–436 of the constant domain may be introduced utilizing any technique known to those of skill in the art. The constant domain or fragment thereof having one or more modifications in amino acid residues 251–256, 285–290, 308–314, 385–389, and 428–436 may be screened by, for example, a binding assay to identify the constant domain or fragment thereof with increased affinity for the FcRn receptor (e.g., as described in section 5.11, infra). Those modifications in the hinge-Fc domain or the fragments thereof which increase the affinity of the constant domain or fragment thereof for the FcRn receptor can be introduced into antibodies to increase the in vivo half-lives of said antibodies. Further, those modifications in the constant domain or the fragment thereof which increase the affinity of the constant domain or fragment thereof for the FcRn can be fused to bioactive molecules to increase the in vivo half-lives of said bioactive molecules (and, preferably alter (increase or decrease) the bioavailability of the molecule, for example, to increase or decrease transport to mucosal surfaces (or other target tissue) (e.g., the lungs).

5.2.1. Mutagenesis

Mutagenesis may be performed in accordance with any of the techniques known in the art including, but not limited to, synthesizing an oligonucleotide having one or more modifications within the sequence of the constant domain of an antibody or a fragment thereof (e.g., the CH2 or CH3 domain) to be modified. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to about 75 nucleotides or more in length is preferred, with about 10 to about 25 or more residues on both sides of the junction of the sequence being altered. A number of such primers introducing a variety of different mutations at one or more positions may be used to generated a library of mutants.

The technique of site-specific mutagenesis is well known in the art, as exemplified by various publications (see, e.g.,. Kunkel et al., *Methods Enzymol.*, 154:367–82, 1987, which is hereby incorporated by reference in its entirety). In general, site-directed mutagenesis is performed by first obtaining a single-stranded vector or melting apart of two strands of a double stranded vector which includes within its sequence a DNA sequence which encodes the desired peptide. An oligonucleotide primer bearing the desired mutated sequence is prepared, generally synthetically. This primer is then annealed with the single-stranded vector, and subjected to DNA polymerizing enzymes such as T7 DNA polymerase, in order to complete the synthesis of the mutation-bearing strand. Thus, a heteroduplex is formed wherein one strand encodes the original non-mutated sequence and the second strand bears the desired mutation. This heteroduplex vector is then used to transform or transfect appropriate cells, such as *E. coli* cells, and clones are selected which include recombinant vectors bearing the mutated sequence arrangement. As will be appreciated, the technique typically employs a phage vector which exists in both a single stranded and double stranded form. Typical vectors useful in site-directed mutagenesis include vectors such as the M13 phage. These phage are readily commercially available and their use is generally well known to those skilled in the art. Double stranded plasmids are also routinely employed in site directed mutagenesis which eliminates the step of transferring the gene of interest from a plasmid to a phage.

Alternatively, the use of PCR™ with commercially available thermostable enzymes such as Taq DNA polymerase may be used to incorporate a mutagenic oligonucleotide primer into an amplified DNA fragment that can then be cloned into an appropriate cloning or expression vector. See, e.g., Tomic et al., *Nucleic Acids Res.*, 18(6):1656, 1987, and Upender et al., *Biotechniques*, 18(1):29–30, 32, 1995, for PCR™-mediated mutagenesis procedures, which are hereby incorporated in their entireties. PCR™ employing a thermostable ligase in addition to a thermostable polymerase may also be used to incorporate a phosphorylated mutagenic oligonucleotide into an amplified DNA fragment that may then be cloned into an appropriate cloning or expression vector (see e.g., Michael, *Biotechniques*, 16(3):410–2, 1994, which is hereby incorporated by reference in its entirety).

Other methods known to those of skill in art of producing sequence variants of the Fc domain of an antibody or a fragment thereof can be used. For example, recombinant vectors encoding the amino acid sequence of the constant domain of an antibody or a fragment thereof may be treated with mutagenic agents, such as hydroxylamine, to obtain sequence variants.

5.2.2. Panning

Vectors, in particular, phage, expressing constant domains or fragments thereof having one or more modifications in amino acid residues 251–256, 285–290, 308–314, 385–389, and/or 428–436 can be screened to identify constant domains or fragments thereof having increased affinity for FcRn to select out the highest affinity binders from a population of phage. Immunoassays which can be used to analyze binding of the constant domain or fragment thereof having one or more modifications in amino acid residues 251–256, 285–290, 308–314, 385–389, and/or 428–436 to the FcRn include, but are not limited to, radioimmunoassays, ELISA (enzyme linked immunosorbent assay), "sandwich" immunoassays, and fluorescent immunoassays. Such assays are routine and well known in the art (see, e.g., Ausubel et al., eds, 1994, *Current Protocols in Molecular Biology*, Vol. 1, John Wiley & Sons, Inc., New York, which is incorporated by reference herein in its entirety). Exemplary immunoassays are described briefly herein below (but are not intended by way of limitation). BIAcore kinetic analysis can also be used to determine the binding on and off rates of a constant domain or a fragment thereof having one or more modifications in amino acid residues 251–256, 285–290, 308–314, 385–389, and/or 428–436 to the FcRn. BIAcore kinetic analysis comprises analyzing the binding and dissociation of a constant domain or a fragment thereof having one or more modifications in amino acid residues 251–256, 285–290, 308–314, 385–389, and/or 428–436 from chips with immobilized FcRn on their surface (see section 5.1 and the Example section infra).

5.2.3. Sequencing

Any of a variety of sequencing reactions known in the art can be used to directly sequence the nucleotide sequence encoding constant domains or fragments thereof having one or more modifications in amino acid residues 251–256, 285–290, 308–314, 385–389, and/or 428–436. Examples of sequencing reactions include those based on techniques developed by Maxim and Gilbert (*Proc. Natl. Acad. Sci. USA*, 74:560, 1977) or Sanger (*Proc. Natl. Acad. Sci. USA*, 74:5463, 1977). It is also contemplated that any of a variety of automated sequencing procedures can be utilized (*Bio/Techniques*, 19:448, 1995), including sequencing by mass spectrometry (see, e.g., PCT Publication No. WO 94/16101, Cohen et al., *Adv. Chromatogr.*, 36:127–162, 1996, and Griffin et al., *Appl. Biochem. Biotechnol.*, 38:147–159, 1993).

5.3. Recombinant Methods of Producing Antibodies

The antibodies of the invention or fragments thereof can be produced by any method known in the art for the synthesis of antibodies, in particular, by chemical synthesis or preferably, by recombinant expression techniques.

The nucleotide sequence encoding an antibody may be obtained from any information available to those of skill in the art (i.e., from Genbank, the literature, or by routine cloning). If a clone containing a nucleic acid encoding a particular antibody or an epitope-binding fragment thereof is not available, but the sequence of the antibody molecule or epitope-binding fragment thereof is known, a nucleic acid encoding the immunoglobulin may be chemically synthesized or obtained from a suitable source (e.g., an antibody cDNA library, or a cDNA library generated from, or nucleic acid, preferably poly $A^+$ RNA, isolated from any tissue or cells expressing the antibody, such as hybridoma cells selected to express an antibody) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Once the nucleotide sequence of the antibody is determined, the nucleotide sequence of the antibody may be manipulated using methods well known in the art for the manipulation of nucleotide sequences, e.g., recombinant DNA techniques, site directed mutagenesis, PCR, etc. (see, for example, the techniques described in Sambrook et al., 1990, *Molecular Cloning, A Laboratory Manual*, 2d Ed., Cold Spring Harbor Laboratory, Cold Spring Harbor, N.Y.; and Ausubel et al., eds., 1998, *Current Protocols in Molecular Biology*, John Wiley & Sons, NY, which are both incorporated by reference herein in their entireties), to generate antibodies having a different amino acid sequence by, for example, introducing amino acid substitutions, deletions, and/or insertions into the epitope-binding domain regions of the antibodies and preferably, into the hinge-Fc regions of the antibodies which are involved in the interaction with the FcRn. In a preferred embodiment, antibodies having one or more modifications in amino acid residues 251–256, 285–290, 308–314, 385–389, and 428–436 are generated.

Recombinant expression of an antibody requires construction of an expression vector containing a nucleotide sequence that encodes the antibody. Once a nucleotide sequence encoding an antibody molecule or a heavy or light chain of an antibody, or portion thereof (preferably, but not necessarily, containing the heavy or light chain variable region) has been obtained, the vector for the production of the antibody molecule may be produced by recombinant DNA technology using techniques well known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding the constant region of the antibody molecule with one or more modifications in the amino acid residues involved in the interaction with the FcRn (see, e.g., PCT Publication WO 86/05887; PCT Publication WO 89/01036; and U.S. Pat. No. 5,122,464). The nucleotide sequence encoding the heavy-chain variable region, light-chain variable region, both the heavy-chain and light-chain variable regions, an epitope-binding fragment of the heavy- and/or light-chain variable region, or one or more complementarity determining regions (CDRs) of an antibody may be cloned into such a vector for expression.

The expression vector is transferred to a host cell by conventional techniques and the transfected cells are then cultured by conventional techniques to produce an antibody having an increased affinity for the FcRn and an increased in vivo half-life. Thus, the invention includes host cells containing a polynucleotide encoding an antibody, a constant domain or a FcRn binding fragment thereof having one or more modifications in amino acid residues 251–256, 285–290, 308–314, 385–389, and/or 428–436, preferably, operably linked to a heterologous promoter.

A variety of host-expression vector systems may be utilized to express the antibody molecules of the invention. Such host-expression systems represent vehicles by which the coding sequences of interest may be produced and subsequently purified, but also represent cells which may, when transformed or transfected with the appropriate nucleotide coding sequences, express an antibody molecule of the invention in situ. These include, but are not limited to, microorganisms such as bacteria (e.g., *E. coli* and *B. subtilis*) transformed with recombinant bacteriophage DNA, plasmid DNA or cosmid DNA expression vectors containing antibody coding sequences; yeast (e.g., *Saccharomyces* and *Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; and tobacco mosaic virus, TMV) or transformed with recombinant plasmid expression vectors (e.g., Ti plasmid) containing antibody coding sequences; and mammalian cell systems (e.g., COS, CHO, BHK, 293, 3T3 and NSO cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as *Escherichia coli*, and more preferably, eukaryotic cells, especially for the expression of whole recombinant antibody molecule, are used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., *Gene*, 45:101, 1986, and Cockett et al., *Bio/Technology*, 8:2, 1990).

In bacterial systems, a number of expression vectors may be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited to, the *E. coli* expression vector pUR278 (Ruther et al., *EMBO*, 12:1791, 1983), in which the antibody coding sequence may be ligated individually into the vector in frame with the lacZ coding region so that a fusion protein is produced; and pIN vectors (Inouye & Inouye, *Nucleic Acids Res.*, 13:3101–3109, 1985 and Van Heeke & Schuster, *J. Biol. Chem.*, 24:5503–5509, 1989).

In an insect system, Autographa californica nuclear polyhedrosis virus (AcNPV) is used as a vector to express foreign genes. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter).

In mammalian host cells, a number of viral-based expression systems may be utilized to express an antibody molecule of the invention. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts (e.g., see Logan & Shenk, *Proc. Natl. Acad. Sci. USA,* 81:355–359, 1984). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see, e.g., Bitter et al., *Methods in Enzymol.,* 153:516–544, 1987).

In addition, a host cell strain may be chosen which modulates the expression of the antibody sequences, or modifies and processes the antibody in the specific fashion desired. Such modifications (e.g., glycosylation) and processing (e.g., cleavage) of protein products may be important for the function of the antibody. Different host cells have characteristic and specific mechanisms for the post-translational processing and modification of proteins and gene products. Appropriate cell lines or host systems can be chosen to ensure the correct modification and processing of the antibody expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, HeLa, COS, MDCK, 293, 3T3, W138, and in particular, myeloma cells such as NS0 cells, and related cell lines, see, for example, Morrison et al., U.S. Pat. No. 5,807,715, which is hereby incorporated by reference in its entirety.

For long-term, high-yield production of recombinant antibodies, stable expression is preferred. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibody molecule. Such engineered cell lines may be particularly useful in screening and evaluation of compositions that interact directly or indirectly with the antibody molecule.

A number of selection systems may be used, including but not limited to, the herpes simplex virus thymidine kinase (Wigler et al., *Cell,* 11:223, 1977), hypoxanthine-guanine phosphoribosyltransferase (Szybalska & Szybalski, *Proc. Natl. Acad. Sci. USA,* 48:202, 1992), and adenine phosphoribosyltransferase (Lowy et al., *Cell,* 22:8–17, 1980) genes can be employed in tk$^-$, hgprt$^-$ or aprt$^-$ cells, respectively. Also, antimetabolite resistance can be used as the basis of selection for the following genes: dhfr, which confers resistance to methotrexate (Wigler et al., *Natl. Acad. Sci. USA,* 77:357, 1980 and O'Hare et al., *Proc. Natl. Acad. Sci. USA,* 78:1527, 1981); gpt, which confers resistance to mycophenolic acid (Mulligan & Berg, *Proc. Natl. Acad. Sci. USA,* 78:2072, 1981); neo, which confers resistance to the aminoglycoside G-418 (Wu and Wu, *Biotherapy,* 3:87–95, 1991; Tolstoshev, *Ann. Rev. Pharmacol. Toxicol.,* 32:573–596, 1993; Mulligan, *Science,* 260:926–932, 1993; and Morgan and Anderson, *Ann. Rev. Biochem.,* 62: 191–217, 1993; and May, *TIB TECH,* 11(5):155–215, 1993); and hygro, which confers resistance to hygromycin (Santerre et al., *Gene,* 30:147, 1984). Methods commonly known in the art of recombinant DNA technology may be routinely applied to select the desired recombinant clone, and such methods are described, for example, in Ausubel et al. (eds.), 1993, *Current Protocols in Molecular Biology,* John Wiley & Sons, NY; Kriegler, 1990, *Gene Transfer and Expression, A Laboratory Manual,* Stockton Press, NY; in Chapters 12 and 13, Dracopoli et al. (eds), 1994, *Current Protocols in Human Genetics,* John Wiley & Sons, NY; and Colberre-Garapin et al., *J. Mol. Biol.,* 150:1, 1981, which are incorporated by reference herein in their entireties.

The expression levels of an antibody molecule can be increased by vector amplification (for a review, see Bebbington and Hentschel, 1987, *The use of vectors based on gene amplification for the expression of cloned genes in mammalian cells in DNA cloning,* Vol.3. Academic Press, New York). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., *Mol., Cell. Biol.,* 3:257, 1983).

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides or different selectable markers to ensure maintenance of both plasmids. Alternatively, a single vector may be used which encodes, and is capable of expressing, both heavy and light chain polypeptides. In such situations, the light chain should be placed before the heavy chain to avoid an excess of toxic free heavy chain (Proudfoot, *Nature,* 322:52, 1986; and Kohler, *Proc. Natl. Acad. Sci. USA,* 77:2 197, 1980). The coding sequences for the heavy and light chains may comprise cDNA or genomic DNA.

Once an antibody molecule of the invention has been produced by recombinant expression, it may be purified by any method known in the art for purification of an immunoglobulin molecule, for example, by chromatography (e.g., ion exchange, affinity, particularly by affinity for the specific antigen after Protein A purification, and sizing column chromatography), centrifugation, differential solubility, or by any other standard techniques for the purification of proteins. Further, the antibodies of the present invention or fragments thereof may be fused to heterologous polypeptide sequences described herein or otherwise known in the art to facilitate purification.

5.3.1. Antibody Conjugates

The present invention encompasses antibodies recombinantly fused or chemically conjugated (including both covalently and non-covalently conjugations) to heterologous polypeptides (i.e., an unrelated polypeptide; or portion thereof, preferably at least 10, at least 20, at least 30, at least 40, at least 50, at least 60, at least 70, at least 80, at least 90 or at least 100 amino acids of the polypeptide) to generate fusion proteins. The fusion does not necessarily need to be direct, but may occur through linker sequences. Antibodies fused or conjugated to heterologous polypeptides may also be used in in vitro immunoassays and purification methods using methods known in the art. See e.g., PCT Publication No. WO 93/21232; EP 439,095; Naramura et al., *Immunol. Lett.*, 39:91–99, 1994; U.S. Pat. No. 5,474,981; Gillies et al., *PNAS,* 89:1428–1432, 1992; and Fell et al., *J. Immunol.*, 146:2446–2452, 1991, which are incorporated herein by reference in their entireties.

Antibodies can be fused to marker sequences, such as a peptide to facilitate purification. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., *Proc. Natl. Acad. Sci. USA,* 86:821–824, 1989, for instance, hexa-histidine provides for convenient purification of the fusion protein. Other peptide tags useful for purification include, but are not limited to, the hemagglutinin "HA" tag, which corresponds to an epitope derived from the influenza hemagglutinin protein (Wilson et al., *Cell,* 37:767 1984) and the "flag" tag (Knappik et al., *Biotechniques,* 17(4):754–761, 1994).

The present invention also encompasses antibodies conjugated to a diagnostic or therapeutic agent or any other molecule for which in vivo half-life is desired to be increased. The antibodies can be used diagnostically to, for example, monitor the development or progression of a disease, disorder or infection as part of a clinical testing procedure to, e.g., determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, radioactive materials, positron emitting metals, and nonradioactive paramagnetic metal ions. The detectable substance may be coupled or conjugated either directly to the antibody or indirectly, through an intermediate (such as, for example, a linker known in the art) using techniques known in the art. See, for example, U.S. Pat. No. 4,741,900 for metal ions which can be conjugated to antibodies for use as diagnostics according to the present invention. Examples of suitable enzymes include horseradish peroxidase, alkaline phosphatase, β-galactosidase, or acetylcholinesterase; examples of suitable prosthetic group complexes include streptavidin/biotin and avidinibiotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}$I, $^{131}$I, $^{111}$In or $^{99m}$Tc.

An antibody may be conjugated to a therapeutic moiety such as a cytotoxin (e.g., a cytostatic or cytocidal agent), a therapeutic agent or a radioactive element (e.g., alpha-emitters, gamma-emitters, etc.). Cytotoxins or cytotoxic agents include any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cisdichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

Further, an antibody may be conjugated to a therapeutic agent or drug moiety that modifies a given biological response. Therapeutic agents or drug moieties are not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, α-interferon (IFN-α), β-interferon (IFN-β), nerve growth factor (NGF), platelet derived growth factor (PDGF), tissue plasminogen activator (TPA), an apoptotic agent (e.g., TNF-α, TNF-β, AIM I as disclosed in PCT Publication No. WO 97/33899), AIM II (see, PCT Publication No. WO 97/34911), Fas Ligand (Takahashi et al., *J. Immunol.,* 6:1567–1574, 1994), and VEGI (PCT Publication No. WO 99/23105), a thrombotic agent or an anti-angiogenic agent (e.g., angiostatin or endostatin); or a biological response modifier such as, for example, a lymphokine (e.g., interleukin-1 ("IL-1"), interleukin-2 ("IL-2"), interleukin-6 ("IL-6"), granulocyte macrophage colony stimulating factor ("GM-CSF"), and granulocyte colony stimulating factor ("G-CSF")), or a growth factor (e.g., growth hormone ("GH")).

Techniques for conjugating such therapeutic moieties to antibodies are well known; see, e.g., Arnon et al., "Monoclonal Antibodies For Immunotargeting Of Drugs In Cancer Therapy", in *Monoclonal Antibodies And Cancer Therapy*, Reisfeld et al. (eds.), 1985, pp. 243–56, Alan R. Liss, Inc.); Hellstrom et al., "Antibodies For Drug Delivery", in *Controlled Drug Delivery* (2nd Ed.), Robinson et al. (eds.), 1987, pp. 623–53, Marcel Dekker, Inc. ); Thorpe, "Antibody Carriers Of Cytotoxic Agents In Cancer Therapy: A Review", in *Monoclonal Antibodies '84:Biological And Clinical Applications*, Pinchera et al. (eds.), 1985, pp. 475–506); "Analysis, Results, And Future Prospective Of The Therapeutic Use Of Radiolabeled Antibody In Cancer Therapy", in *Monoclonal Antibodies For Cancer Detection And Therapy*, Baldwin et al. (eds.),1985, pp. 303–16, Academic Press; and Thorpe et al., *Immunol. Recombinant expression vector.,* 62:119–58, 1982.

An antibody or fragment thereof, with or without a therapeutic moiety conjugated to it, administered alone or in combination with cytotoxic factor(s) and/or cytokine(s) can be used as a therapeutic.

Alternatively, an antibody can be conjugated to a second antibody to form an antibody heteroconjugate as described by Segal in U.S. Pat. No. 4,676,980, which is incorporated herein by reference in its entirety.

Antibodies may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

5.4 Methods of Producing Fusion Proteins

Fusion proteins can be produced by standard recombinant DNA techniques or by protein synthetic techniques, e.g., by use of a peptide synthesizer. For example, a nucleic acid molecule encoding a fusion protein can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, e.g., *Current Protocols in Molecular Biology*, Ausubel et al., eds., John Wiley & Sons, 1992). Moreover, a nucleic acid encoding a bioactive molecule can be cloned into an expression vector containing the Fc domain or a fragment thereof such that the bioactive molecule is linked in-frame to the constant domain or fragment thereof.

Methods for fusing or conjugating polypeptides to the constant regions of antibodies are known in the art. See, e.g., U.S. Pat. Nos. 5,336,603, 5,622,929, 5,359,046, 5,349,053, 5,447,851, 5,723,125, 5,783,181, 5,908,626, 5,844,095, and 5,112,946; EP 307,434; EP 367,166; EP 394,827; PCT publications WO 91/06570, WO 96/04388, WO 96/22024, WO 97/34631, and WO 99/04813; Ashkenazi et al., *Proc. Natl. Acad. Sci. USA*, 88: 10535–10539, 1991; Traunecker et al., *Nature*, 331:84–86, 1988; Zheng et al., *J. Immunol.*, 154:5590–5600, 1995; and Vil et al., *Proc. Natl. Acad. Sci. USA*, 89:11337–11341, 1992, which are incorporated herein by reference in their entireties.

The nucleotide sequence encoding a bioactive molecule may be obtained from any information available to those of skill in the art (e.g., from Genbank, the literature, or by routine cloning), and the nucleotide sequence encoding a constant domain or a fragment thereof with increased affinity for the FcRn may be determined by sequence analysis of mutants produced using techniques described herein, or may be obtained from Genbank or the literature. The nucleotide sequence coding for a fusion protein can be inserted into an appropriate expression vector, i.e., a vector which contains the necessary elements for the transcription and translation of the inserted protein-coding sequence. A variety of host-vector systems may be utilized in the present invention to express the protein-coding sequence. These include but are not limited to mammalian cell systems infected with virus (e.g., vaccinia virus, adenovirus, etc.); insect cell systems infected with virus (e.g., baculovirus); microorganisms such as yeast containing yeast vectors; or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used.

The expression of a fusion protein may be controlled by any promoter or enhancer element known in the art. Promoters which may be used to control the expression of the gene encoding fusion protein include, but are not limited to, the SV40 early promoter region (Bernoist and Chambon, *Nature*, 290:304–310, 1981), the promoter contained in the 3' long terminal repeat of Rous sarcoma virus (Yamamoto, et al., *Cell*, 22:787–797, 1980), the herpes thymidine kinase promoter (Wagner et al., *Proc. Natl. Acad. Sci. U.S.A.*, 78:1441–1445, 1981), the regulatory sequences of the metallothionein gene (Brinster et al., *Nature*, 296:39–42, 1982), the tetracycline (Tet) promoter (Gossen et al., *Proc. Nat. Acad. Sci. USA*, 89:5547–5551, 1995); prokaryotic expression vectors such as the β-lactamase promoter (Villa-Kamaroff, et al., *Proc. Natl. Acad. Sci. U.S.A.*, 75:3727–3731, 1978), or the tac promoter (DeBoer, et al., *Proc. Natl. Acad. Sci. U.S.A.*, 80:21–25, 1983; see also "Useful proteins from recombinant bacteria" in *Scientific American*, 242:74–94, 1980); plant expression vectors comprising the nopaline synthetase promoter region (Herrera-Estrella et al., *Nature*, 303:209–213, 1983) or the cauliflower mosaic virus 35S RNA promoter (Gardner, et al., *Nucl. Acids Res.*, 9:2871, 1981), and the promoter of the photosynthetic enzyme ribulose biphosphate carboxylase (Herrera-Estrella et al., *Nature*, 310:115–120, 1984); promoter elements from yeast or other fungi such as the Gal 4 promoter, the ADC (alcohol dehydrogenase) promoter, PGK (phosphoglycerol kinase) promoter, alkaline phosphatase promoter, and the following animal transcriptional control regions, which exhibit tissue specificity and have been utilized in transgenic animals: elastase I gene control region which is active in pancreatic acinar cells (Swift et al., *Cell* 38:639–646, 1984; Ornitz et al., 50:399–409, *Cold Spring Harbor Symp. Quant. Biol.*, 1986; MacDonald, *Hepatology* 7:425–515, 1987); insulin gene control region which is active in pancreatic beta cells (Hanahan, *Nature* 315:115–122, 1985), immunoglobulin gene control region which is active in lymphoid cells (Grosschedl et al., *Cell*, 38:647–658, 1984; Adames et al., *Nature* 318:533–538, 1985; Alexander et al., *Mol. Cell. Biol.*, 7:1436–1444, 1987), mouse mammary tumor virus control region which is active in testicular, breast, lymphoid and mast cells (Leder et al., *Cell*, 45:485–495, 1986), albumin gene control region which is active in liver (Pinkert et al., *Genes and Devel.*, 1:268–276, 1987), α-fetoprotein gene control region which is active in liver (Krumlauf et al., *Mol. Cell. Biol.*, 5:1639–1648, 1985; Hammer et al., *Science*, 235:53–58, 1987; α 1-antitrypsin gene control region which is active in the liver (Kelsey et al., *Genes and Devel.*, 1:161–171, 1987), beta-globin gene control region which is active in myeloid cells (Mogram et al., *Nature*, 315:338–340, 1985; Kollias et al., *Cell*, 46:89–94, 1986; myelin basic protein gene control region which is active in oligodendrocyte cells in the brain (Readhead et al., *Cell*, 48:703–712, 1987); myosin light chain-2 gene control region which is active in skeletal muscle (Sani, *Nature*, 314:283–286, 1985); neuronal-specific enolase (NSE) which is active in neuronal cells (Morelli et al., *Gen. Virol.*, 80:571–83, 1999); brain-derived neurotrophic factor (BDNF) gene control region which is active in neuronal cells (Tabuchi et al., *Biochem. Biophysic. Res. Comprising.*, 253:818–823, 1998); glial fibrillary acidic protein (GFAP) promoter which is active in astrocytes (Gomes et al., Braz. J. Med. Biol. Res., 32(5):619–631, 1999; Morelli et al., *Gen. Virol.*, 80:571–83, 1999) and gonadotropic releasing hormone gene control region which is active in the hypothalamus (Mason et al., *Science*, 234:1372–1378, 1986).

In a specific embodiment, the expression of a fusion protein is regulated by a constitutive promoter. In another embodiment, the expression of a fusion protein is regulated by an inducible promoter. In accordance with these embodiments, the promoter may be a tissue-specific promoter.

In a specific embodiment, a vector is used that comprises a promoter operably linked to a fusion protein-encoding nucleic acid, one or more origins of replication, and, optionally, one or more selectable markers (e.g., an antibiotic resistance gene).

In mammalian host cells, a number of viral-based expression systems may be utilized. In cases where an adenovirus is used as an expression vector, the fusion protein coding sequence may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts (e.g., see Logan & Shenk, *Proc. Natl. Acad. Sci. USA,* 81:355–359, 1984). Specific initiation signals may also be required for efficient translation of inserted fusion protein coding sequences. These signals include the ATG initiation codon and adjacent sequences. Furthermore, the initiation codon must be in phase with the reading frame of the desired coding sequence to ensure translation of the entire insert. These exogeneous translation control signals and initiation codons can be of a variety of origins, both natural and synthetic. The efficiency of expression may be enhanced by the inclusion of appropriate transcription enhancer elements, transcription terminators, etc. (see Bitter et al., *Methods in Enzymol.,* 153: 516–544, 1987).

Expression vectors containing inserts of a gene encoding a fusion protein can be identified by three general approaches: (a) nucleic acid hybridization, (b) presence or absence of "marker" gene functions, and (c) expression of inserted sequences. In the first approach, the presence of a gene encoding a fusion protein in an expression vector can be detected by nucleic acid hybridization using probes comprising sequences that are homologous to an inserted gene encoding the fusion protein. In the second approach, the recombinant vector/host system can be identified and selected based upon the presence or absence of certain "marker" gene functions (e.g. thymidine kinase activity, resistance to antibiotics, transformation phenotype, occlusion body formation in baculovirus, etc.) caused by the insertion of a nucleotide sequence encoding a fusion protein in the vector. For example, if the nucleotide sequence encoding the fusion protein is inserted within the marker gene sequence of the vector, recombinants containing the gene encoding the fusion protein insert can be identified by the absence of the marker gene function. In the third approach, recombinant expression vectors can be identified by assaying the gene product (i.e., fusion protein) expressed by the recombinant. Such assays can be based, for example, on the physical or functional properties of the fusion protein in in vitro assay systems, e.g., binding with anti-bioactive molecule antibody.

In addition, a host cell strain may be chosen which modulates the expression of the inserted sequences, or modifies and processes the gene product in the specific fashion desired. Expression from certain promoters can be elevated in the presence of certain inducers; thus, expression of the genetically engineered fusion protein may be controlled. Furthermore, different host cells have characteristic and specific mechanisms for the translational and post-translational processing and modification (e.g., glycosylation, phosphorylation of proteins). Appropriate cell lines or host systems can be chosen to ensure the desired modification and processing of the foreign protein expressed. For example, expression in a bacterial system will produce an unglycosylated product and expression in yeast will produce a glycosylated product. Eukaryotic host cells which possess the cellular machinery for proper processing of the primary transcript, glycosylation, and phosphorylation of the gene product may be used. Such mammalian host cells include but are not limited to CHO, VERY, BHK, HeLa, COS, MDCK, 293, 3T3, WI38, and in particular, neuronal cell lines such as, for example, SK-N-AS, SK-N-FJ, SK-N-DZ human neuroblastomas (Sugimoto et al., *J. Natl. Cancer Inst.,* 73: 51–57, 1984), SK-N-SH human neuroblastoma (*Biochim. Biophys. Acta,* 704: 450–460, 1982), Daoy human cerebellar medulloblastoma (He et al., *Cancer Res.,* 52: 1144–1148, 1992) DBTRG-05MG glioblastoma cells (Kruse et al., 1992, *In Vitro Cell. Dev. Biol.,* 28A:609–614, 1992), IMR-32 human neuroblastoma (*Cancer Res.,* 30: 2110–2118, 1970), 1321N1 human astrocytoma (*Proc. Natl Acad. Sci. USA,* 74: 4816, 1997), MOG-G-CCM human astrocytoma (Br. J. Cancer, 49: 269, 1984), U87MG human glioblastoma-astrocytoma (*Acta Pathol. Microbiol. Scand.,* 74: 465–486, 1968), A172 human glioblastoma (Olopade et al., *Cancer Res.,* 52: 2523–2529, 1992), C6 rat glioma cells (Benda et al., Science, 161: 370–371, 1968), Neuro-2a mouse neuroblastoma (*Proc. Natl. Acad. Sci. USA,* 65: 129–136, 1970), NB41A3 mouse neuroblastoma (*Proc. Natl. Acad. Sci. USA,* 48: 1184–1190, 1962), SCP sheep choroid plexus (Bolin et al., *J. Virol. Methods,* 48: 211–221, 1994), G355-5, PG-4 Cat normal astrocyte (Haapala et al., *J. Virol.,* 53: 827–833, 1985), Mpf ferret brain (Trowbridge et al., *In Vitro,* 18: 952–960, 1982), and normal cell lines such as, for example, CTX TNA2 rat normal cortex brain (Radany et al., *Proc. Natl. Acad. Sci. USA,* 89: 6467–6471, 1992) such as, for example, CRL7030 and Hs578Bst. Furthermore, different vector/host expression systems may effect processing reactions to different degrees.

For long-term, high-yield production of recombinant proteins, stable expression is preferred. For example, cell lines which stably express the fusion protein may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1–2 days in an enriched medium, and then are switched to a selective medium. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines that express the differentially expressed or pathway gene protein. Such engineered cell lines may be particularly useful in screening and evaluation of compounds that affect the endogenous activity of the differentially expressed or pathway gene protein.

A number of selection systems may be used, including but not limited to the herpes simplex virus thymidine kinase (Wigler, et al., *Cell,* 11:223, 1997), hypoxanthine-guanine phosphoribosyltransferase (Szybalska & Szybalski, *Proc. Natl. Acad. Sci. USA,* 48:2026, 1962), and adenine phosphoribosyltransferase (Lowy, et al., 1980, *Cell,* 22:817, 1980) genes can be employed in tk-, hgprt- or aprt-cells, respectively. Also, antimetabolite resistance can be used as the basis of selection for dhfr, which confers resistance to methotrexate (Wigler, et al., *Natl. Acad. Sci. USA,* 77:3567, 1980; O'Hare, et al., *Proc. Natl. Acad. Sci. USA,* 78:1527, 1981); gpt, which confers resistance to mycophenolic acid (Mulligan & Berg, *Proc. Natl. Acad. Sci. USA,* 78:2072, 1981); neo, which confers resistance to the aminoglycoside G-418 (Colberre-Garapin, et al., *J. Mol. Biol.,* 150:1, 1981); and hygro, which confers resistance to hygromycin (Santerre, et al., *Gene,* 30:147, 1984) genes.

Once a fusion protein of the invention has been produced by recombinant expression, it may be purified by any method known in the art for purification of a protein, for example, by chromatography (e.g., ion exchange, affinity, particularly by affinity for the specific antigen after Protein A, and sizing column chromatography), centrifugation, differential solubility, or by any other standard technique for the purification of proteins.

5.5. Prophylactic and Therapeutic Uses of Antibodies

The present invention encompasses antibody-based therapies which involve administering antibodies to an animal, preferably a mammal, and most preferably a human, for preventing, treating, or ameliorating symptoms associated with a disease, disorder, or infection. Prophylactic and therapeutic compounds of the invention include, but are not limited to, antibodies and nucleic acids encoding antibodies. Antibodies may be provided in pharmaceutically acceptable compositions as known in the art or as described herein.

Antibodies of the present invention that function as antagonists of a disease, disorder, or infection can be administered to an animal, preferably a mammal and most preferably a human, to treat, prevent or ameliorate one or more symptoms associated with the disease, disorder, or infection. For example, antibodies which disrupt or prevent the interaction between a viral antigen and its host cell receptor may be administered to an animal, preferably a mammal and most preferably a human, to treat, prevent or ameliorate one or more symptoms associated with a viral infection.

In a specific embodiment, an antibody or fragment thereof prevents a viral or bacterial antigen from binding to its host cell receptor by at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to antigen binding to its host cell receptor in the absence of said antibodies. In another embodiment, a combination of antibodies prevent a viral or bacterial antigen from binding to its host cell receptor by at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to antigen binding to its host cell receptor in the absence of said antibodies. In a preferred embodiment, the antibody is used to treat or prevent RSV infection Antibodies which do not prevent a viral or bacterial antigen from binding its host cell receptor but inhibit or downregulate viral or bacterial replication can also be administered to an animal to treat, prevent or ameliorate one or more symptoms associated with a viral or bacterial infection. The ability of an antibody to inhibit or downregulate viral or bacterial replication may be determined by techniques described herein or otherwise known in the art. For example, the inhibition or downregulation of viral replication can be determined by detecting the viral titer in the animal.

In a specific embodiment, an antibody inhibits or downregulates viral or bacterial replication by at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to viral or bacterial replication in absence of said antibody. In another embodiment, a combination of antibodies inhibit or downregulate viral or bacterial replication by at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to viral or bacterial replication in absence of said antibodies.

Antibodies can also be used to prevent, inhibit or reduce the growth or metastasis of cancerous cells. In a specific embodiment, an antibody inhibits or reduces the growth or metastasis of cancerous cells by at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to the growth or metastasis in absence of said antibody. In another embodiment, a combination of antibodies inhibits or reduces the growth or metastasis of cancer by at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to the growth or metastasis in absence of said antibodies. Examples of cancers include, but are not limited to, leukemia (e.g, acute leukemia such as acute lymphocytic leukemia and acute myelocytic leukemia), neoplasms, tumors (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma), heavy chain disease, metastases, or any disease or disorder characterized by uncontrolled cell growth.

Antibodies can also be used to reduce the inflammation experienced by animals, particularly mammals, with inflammatory disorders. In a specific embodiment, an antibody reduces the inflammation in an animal by at least 99%, at least 95%, at least 90%, at least 85%, at least 80%, at least 75%, at least 70%, at least 60%, at least 50%, at least 45% at least 40%, at least 45%, at least 35%, at least 30%, at least 25%, at least 20%, or at least 10% relative to the inflammation in an animal in the not administered said antibody. In another embodiment, a combination of antibodies reduce the inflammation in an animal by at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to the inflammation in an animal in not administered said antibodies. Examples of inflammatory disorders include, but are not limited to, rheumatoid arthritis, spondyloarthropathies, inflammatory bowel disease and asthma.

In certain embodiments, the antibody used for treatment of inflammation (or cancer) is a modified anti-$\alpha_v\beta_3$ antibody, preferably a Vitaxin antibody (see, PCT publications WO 98/33919 and WO 00/78815, both by Huse et al., and both of which are incorporated by reference herein in their entireties).

Antibodies can also be used to prevent the rejection of transplants. Antibodies can also be used to prevent clot formation. Further, antibodies that function as agonists of the immune response can also be administered to an animal, preferably a mammal, and most preferably a human, to treat, prevent or ameliorate one or more symptoms associated with the disease, disorder, or infection.

One or more antibodies that immunospecifically bind to one or more antigens may be used locally or systemically in the body as a therapeutic. The antibodies of this invention may also be advantageously utilized in combination with other monoclonal or chimeric antibodies, or with lymphokines or hematopoietic growth factors (such as, e.g., IL-2, IL-3 and IL-7), which, for example, serve to increase the number or activity of effector cells which interact with the antibodies. The antibodies of this invention may also be advantageously utilized in combination with other monoclonal or chimeric antibodies, or with lymphokines or hematopoietic growth factors (such as, e.g., IL-2, IL-3 and IL-7), which, for example, serve to increase the immune response. The antibodies of this invention may also be advantageously utilized in combination with one or more drugs used to treat a disease, disorder, or infection such as, for example anti-cancer agents, anti-inflammatory agents or anti-viral agents. Examples of anti-cancer agents include, but are not limited to, isplatin, ifosfamide, paclitaxel, taxanes, topoisomerase I inhibitors (e.g. CPT-11, topotecan, 9-AC, and GG-211), gemcitabine, vinorelbine, oxaliplatin, 5-fluorouracil (5-FU), leucovorin, vinorelbine, temodal, and taxol. Examples of anti-viral agents include, but are not limited to, cytokines (e.g., IFN-α, IFN-β, IFN-γ), inhibitors of reverse transcriptase (e.g., AZT, 3TC, D4T, ddC, ddI, d4T, 3TC, adefovir, efavirenz, delavirdine, nevirapine, abacavir, and other dideoxynucleosides or dideoxyfluoronucleosides), inhibitors of viral mRNA capping, such as ribavirin, inhibitors of proteases such HIV protease inhibitors (e.g., amprenavir, indinavir, nelfinavir, ritonavir, and saquinavir,), amphotericin B, castanospermine as an inhibitor of glycoprotein processing, inhibitors of neuraminidase such as influenza virus neuraminidase inhibitors (e.g., zanamivir and oseltamivir), topoisomerase I inhibitors (e.g., camptothecins and analogs thereof), amantadine, and rimantadine. Examples of anti-inflammatory agents include, but are not limited to, nonsteroidal anti-inflammatory drugs such as COX-2 inhibitors (e.g., meloxicam, celecoxib, rofecoxib, flosulide, and SC-58635, and MK-966), ibuprofen and indomethacin, and steroids (e.g., deflazacort, dexamethasone and methylprednisolone).

In a specific embodiment, antibodies administered to an animal are of a species origin or species reactivity that is the same species as that of the animal. Thus, in a preferred embodiment, human or humanized antibodies, or nucleic acids encoding human or human, are administered to a human patient for therapy or prophylaxis.

In preferred embodiments, immunoglobulins having extended in vivo half-lives are used in passive immunotherapy (for either therapy or prophylaxis). Because of the extended half-life, passive immunotherapy or prophylaxis can be accomplished using lower doses and/or less frequent administration of the therapeutic resulting in fewer side effects, better patient compliance, less costly therapy/prophylaxis, etc. In a preferred embodiment, the therapeutic/prophylactic is an antibody that binds RSV, for example, SYNAGIS® or other anti-RSV antibody. Such anti-RSV antibodies, and methods of administration are disclosed in U.S. patent application Ser. Nos. 09/724,396 and 09/724,531, both entitled "Methods of Administering/Dosing Anti-RSV Antibodies For Prophylaxis and Treatment," both by Young et al., both filed Nov. 28, 2000, and continuation-in-part applications of these applications, Ser. Nos. 09/996,265 and 09/996,288, respectively, also entitled "Methods of Administering/Dosing Anti-RSV Antibodies for Prophylaxis and Treatment," by Young et al., all which are incorporated by reference herein in their entireties. Also included are the anti-RSV antibodies described in Section 5.1, supra.

In a specific embodiment, fusion proteins administered to an animal are of a species origin or species reactivity that is the same species as that of the animal. Thus, in a preferred embodiment, human fusion proteins or nucleic acids encoding human fusion proteins, are administered to a human subject for therapy or prophylaxis.

5.6. Prophylactic and Therapeutic Uses of Fusions Proteins and Conjugated Molecules The present invention encompasses fusion protein-based and conjugated molecule-based therapies which involve administering fusion proteins or conjugated molecules to an animal, preferably a mammal and most preferably a human, for preventing, treating, or ameliorating symptoms associated with a disease, disorder, or infection. Prophylactic and therapeutic compounds of the invention include, but are not limited to, fusion proteins and nucleic acids encoding fusion proteins and conjugated molecules. Fusion proteins and conjugated molecules may be provided in pharmaceutically acceptable compositions as known in the art or as described herein.

Fusion proteins and conjugated molecules of the present invention that function as antagonists of a disease, disorder, or infection can be administered to an animal, preferably a mammal, and most preferably a human, to treat, prevent or ameliorate one or more symptoms associated with the disease, disorder, or infection. Further, fusion proteins and conjugated molecules of the present invention that function as agonists of the immune response may be administered to an animal, preferably a mammal, and most preferably a human, to treat, prevent or ameliorate one or more symptoms associated with the disease, disorder, or infection.

One or more fusion proteins and conjugated molecules may be used locally or systemically in the body as a therapeutic. The fusion proteins and conjugated molecules of this invention may also be advantageously utilized in combination with monoclonal or chimeric antibodies, or with lymphokines or hematopoietic growth factors (such as, e.g., IL-2, IL-3 and IL-7), which, for example, serve to increase the number or activity of effector cells which interact with the antibodies. The fusion proteins and conjugated molecules of this invention may also be advantageously utilized in combination with monoclonal or chimeric antibodies, or with lymphokines or hematopoietic growth factors (such as, e.g., IL-2, IL-3 and IL-7), which, for example, serve to increase the immune response. The fusion proteins and conjugated molecules of this invention may also be advantageously utilized in combination with one or more drugs used to treat a disease, disorder, or infection such as, for example anti-cancer agents, anti-inflammatory agents or anti-viral agents. Examples of anti-cancer agents include, but are not limited to, isplatin, ifosfamide, paclitaxel, taxanes, topoisomerase I inhibitors (e.g., CPT-11, topotecan, 9-AC, and GG-211), gemcitabine, vinorelbine, oxaliplatin, 5-fluorouracil (5-FU), leucovorin, vinorelbine, temodal, and taxol. Examples of anti-viral agents include, but are not limited to, cytokines (e.g, IFN-α, IFN-β, IFN-γ), inhibitors of reverse transcriptase (e.g., AZT, 3TC, D4T, ddC, ddI, d4T, 3TC, adefovir, efavirenz, delavirdine, nevirapine, abacavir, and other dideoxynucleosides or dideoxyfluoronucleosides), inhibitors of viral mRNA capping, such as ribavirin, inhibitors of proteases such HIV protease inhibitors (e.g., amprenavir, indinavir, nelfinavir, ritonavir, and saquinavir,), amphotericin B, castanospermine as an inhibitor of glycoprotein processing, inhibitors of neuraminidase such as influenza virus neuraminidase inhibitors (e.g., zanamivir and oseltamivir), topoisomerase I inhibitors (e.g., camptothecins and analogs thereof), amantadine, and rimantadine. Examples of anti-inflammatory agents include, but are not limited to, nonsteroidal anti-inflammatory drugs such as COX-2 inhibitors (e.g., meloxicam, celecoxib, rofecoxib, flosulide, and SC-58635, and MK-966), ibuprofen and indomethacin, and steroids (e.g., deflazacort, dexamethasone and methylprednisolone).

5.7. Administration of Antibodies or Fusion Proteins

The invention provides methods of treatment, prophylaxis, and amelioration of one or more symptoms associated with a disease, disorder or infection by administrating to a subject of an effective amount of an antibody of the invention, or pharmaceutical composition comprising an antibody of the invention. The invention also provides methods of treatment, prophylaxis, and amelioration of one or more symptoms associated with a disease, disorder or infection by administering to a subject an effective amount of a fusion protein or conjugated molecule of the invention, or a pharmaceutical composition comprising a fusion protein or conjugated molecules of the invention. In a preferred aspect, an antibody or fusion protein or conjugated molecule, is substantially purified (i.e., substantially free from substances that limit its effect or produce undesired side-effects). In a specific embodiment, the subject is an animal, preferably a mammal such as non-primate (e.g., cows, pigs, horses, cats, dogs, rats etc.) and a primate (e.g., monkey such as a cynomolgous monkey and a human). In a preferred embodiment, the subject is a human.

Various delivery systems are known and can be used to administer an antibody or fusion protein or conjugated molecule of the invention, e.g., encapsulation in liposomes, microparticles, microcapsules, recombinant cells capable of expressing the antibody or fusion protein, receptor-mediated endocytosis (see, e.g., Wu and Wu, *J. Biol. Chem.*, 262: 4429–4432, 1987), construction of a nucleic acid as part of a retroviral or other vector, etc. Methods of administering an antibody, a fusion protein or conjugated molecule, or pharmaceutical composition include, but are not limited to, parenteral administration (e.g., intradermal, intramuscular, intraperitoneal, intravenous and subcutaneous), epidural, and mucosal (e.g., intranasal and oral routes). In a specific embodiment, antibodies, fusion proteins, conjugated molecules, or pharmaceutical compositions are administered intramuscularly, intravenously, or subcutaneously. The compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, pulmonary administration can also be employed, e.g., by use of an inhaler or nebulizer, and formulation with an aerosolizing agent. See, e.g., U.S. Pat. Nos. 6,019,968; 5,985,320; 5,985,309; 5,934,272; 5,874,064; 5,855,913; 5,290,540; and 4,880,078; and PCT Publication Nos. WO 92/19244; WO 97/32572; WO 97/44013; WO 98/31346; and WO 99/66903, each of which is incorporated herein by reference in its entirety. In a preferred embodiment, an antibody, a fusion protein, conjugated molecules, or a pharmaceutical composition is administered using Alkermes AIR™ pulmonary drug delivery technology (Alkermes, Inc., Cambridge, Mass.).

The invention also provides that an antibody, a fusion protein, or conjugated molecule is packaged in a hermetically sealed container such as an ampoule or sachette indicating the quantity of antibody, fusion protein, or conjugated molecule. In one embodiment, the antibody, fusion protein, or conjugated molecule is supplied as a dry sterilized lyophilized powder or water free concentrate in a hermetically sealed container and can be reconstituted, e.g., with water or saline to the appropriate concentration for administration to a subject. Preferably, the antibody, fusion protein, or conjugated molecule is supplied as a dry sterile lyophilized powder in a hermetically sealed container at a unit dosage of at least 5 mg, more preferably at least 10 mg, at least 15 mg, at least 25 mg, at least 35 mg, at least 45 mg, at least 50 mg, or at least 75 mg. The lyophilized antibody, fusion protein, or conjugated molecule should be stored at between 2 and 8° C. in its original container and the antibody, fusion protein, or conjugated molecules should be administered within 12 hours, preferably within 6 hours, within 5 hours, within 3 hours, or within 1 hour after being reconstituted. In an alternative embodiment, an antibody, fusion protein, or conjugated molecule is supplied in liquid form in a hermetically sealed container indicating the quantity and concentration of the antibody, fusion protein, or conjugated molecule. Preferably, the liquid form of the antibody, fusion protein, or conjugated molecule is supplied in a hermetically sealed container at least 1 mg/ml, more preferably at least 2.5 mg/ml, at least 5 mg/ml, at least 8 mg/ml, at least 10 mg/ml, at least 15 mg/kg, or at least 25 mg/ml.

In a specific embodiment, it may be desirable to administer the pharmaceutical compositions of the invention locally to the area in need of treatment; this may be achieved by, for example, and not by way of limitation, local infusion, by injection, or by means of an implant, said implant being of a porous, non-porous, or gelatinous material, including membranes, such as sialastic membranes, or fibers. Preferably, when administering an antibody or a fusion protein, care must be taken to use materials to which the antibody or the fusion protein does not absorb.

In another embodiment, the composition can be delivered in a vesicle, in particular a liposome (see Langer, *Science*, 249:1527–1533, 1990; Treat et al., in Liposomes in the Therapy of Infectious Disease and Cancer, Lopez-Berestein and Fidler (eds.), Liss, New York, pp. 353–365 (1989); Lopez-Berestein, ibid., pp. 3 17–327; see generally ibid.).

In yet another embodiment, the composition can be delivered in a controlled release or sustained release system. Any technique known to one of skill in the art can be used to produce sustained release formulations comprising one or more antibodies, or one or more fusion proteins. See, e.g. U.S. Pat. No. 4,526,938; PCT publication WO 91/05548; PCT publication WO 96/20698; Ning et al., "Intratumoral Radioimmunotheraphy of a Human Colon Cancer Xenograft Using a Sustained-Release Gel," *Radiotherapy & Oncology*, 39:179–189, 1996; Song et al., "Antibody Mediated Lung Targeting of Long-Circulating Emulsions," *PDA Journal of Pharmaceutical Science & Technology*, 50:372–397, 1995; Cleek et al., "Biodegradable Polymeric Carriers for a bFGF Antibody for Cardiovascular Application," *Pro. Intl. Symp. Control. Rel. Bioact. Mater.*, 24:853–854, 1997; and Lam et al., "Microencapsulation of Recombinant Humanized Monoclonal Antibody for Local Delivery," *Proc. Int'l. Symp. Control Rel. Bioact. Mater.*, 24:759–760, 1997, each of which is incorporated herein by reference in its entirety. In one embodiment, a pump may be used in a controlled release system (see Langer, supra; Sefton, *CRC Crit. Ref. Biomed. Eng.,* 14:20, 1987; Buchwald et al., *Surgery,* 88:507, 1980; and Saudek et al., *N. Engl. J. Med.,* 321:574, 1989). In another embodiment, polymeric materials can be used to achieve controlled release of antibodies or fusion proteins (see e.g., Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, N.Y. (1984); Ranger and Peppas, *J., Macromol. Sci. Rev. Macromol. Chem.,* 23:61, 1983; see also Levy et al., *Science,* 228:190, 1985; During et al., *Ann. Neurol.,* 25:351, 1989; Howard et al., *J. Neurosurg.,* 7 1:105, 1989); U.S. Pat. No. 5,679,377; U.S. Pat. No. 5,916,597; U.S. Pat. No. 5,912,015; U.S. Pat. No. 5,989,463; U.S. Pat. No. 5,128,326; PCT Publication No. WO 99/15154; and PCT Publication No. WO 99/20253). In yet another embodiment, a controlled release system can be placed in proximity of the therapeutic target (e.g., the lungs), thus requiring only a fraction of the systemic dose (see, e.g., Goodson, in Medical Applications of Controlled Release, supra, vol. 2, pp. 115–138 (1984)).

Other controlled release systems are discussed in the review by Langer, *Science,* 249:1527–1533, 1990).

In a specific embodiment where the composition of the invention is a nucleic acid encoding an antibody or fusion protein, the nucleic acid can be administered in vivo to promote expression of its encoded antibody or fusion protein, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see e.g., Joliot et al., *Proc. Natl. Acad. Sci. USA,* 88:1864–1868, 1991), etc. Alternatively, a nucleic acid can be introduced intracellularly and incorporated within host cell DNA for expression by homologous recombination.

The present invention also provides pharmaceutical compositions. Such compositions comprise a prophylactically or therapeutically effective amount of an antibody, fusion protein or conjugated molecule, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant (e.g., Freund's complete and incomplete, mineral gels such as aluminum hydroxide, surface active substances such as lysolecithin, pluronic polyols, polyanions, peptides, oil emulsions, keyhole limpet hemocyanins, dinitrophenol, and potentially useful adjuvants for humans such as BCG (Bacille Calmette-Guerin) and *Corynebacterium parvum*), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a prophylactically or therapeutically effective amount of the antibody or fragment thereof, or fusion protein or conjugated molecule, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection.

Generally, the ingredients of compositions of the invention are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compositions of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The amount of the composition of the invention which will be effective in the treatment, prevention or amelioration of one or more symptoms associated with a disease, disorder, or infection can be determined by standard clinical techniques. The precise dose to be employed in the formulation will depend on the route of administration, the age of the subject, and the seriousness of the disease, disorder, or infection, and should be decided according to the judgment of the practitioner and each patient's circumstances. Effective doses may be extrapolated from dose-response curves derived from in vitro or animal model (e.g., the cotton rat or Cynomolgous monkey) test systems.

For fusion proteins, the therapeutically or prophylactically effective dosage administered to a subject ranges from about 0.001 to 50 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. For antibodies, the therapeutically or prophylactically effective dosage administered to a subject is typically 0.1 mg/kg to 200 mg/kg of the subject's body weight. Preferably, the dosage administered to a subject is between 0.1 mg/kg and 20 mg/kg of the subject's body weight and more preferably the dosage administered to a subject is between 1 mg/kg to 10 mg/kg of the subject's body weight. The dosage will, however, depend upon the extent to which the in vivo half-life of the molecule has been increased Generally, human antibodies and human fusion proteins have longer half-lives within the human body than antibodies of fusion proteins from other species due to the immune response to the foreign polypeptides. Thus, lower dosages of human antibodies or human fusion proteins and less frequent administration is often possible. Further, the dosage and frequency of administration of antibodies, fusion proteins, or conjugated molecules may be reduced also by enhancing uptake and tissue penetration (e.g., into the lung) of the antibodies or fusion proteins by modifications such as, for example, lipidation.

Treatment of a subject with a therapeutically or prophylactically effective amount of an antibody, fusion protein, or conjugated molecule can include a single treatment or, preferably, can include a series of treatments. In a preferred example, a subject is treated with an antibody, fusion protein, or conjugated molecule in the range of between about 0.1 to 30 mg/kg body weight, one time per week for between about 1 to 10 weeks, preferably between 2 to 8 weeks, more preferably between about 3 to 7 weeks, and even more referably for about 4, 5, or 6 weeks. In other embodiments, the pharmaceutical composition of the invention is administered once a day, twice a day, or three times a day. In other embodiments, the pharmaceutical composition is administered once a week, twice a week, once every two weeks, once a month, once every six weeks, once every two months, twice a year or once per year. It will also be appreciated that the effective dosage of the antibody, fusion protein, or conjugated molecule used for treatment may increase or decrease over the course of a particular treatment.

5.7.1. Gene Therapy

In a specific embodiment, nucleic acids comprising sequences encoding antibodies or fusion proteins, are administered to treat, prevent or ameliorate one or more symptoms associated with a disease, disorder, or infection, by way of gene therapy. Gene therapy refers to therapy performed by the administration to a subject of an expressed or expressible nucleic acid. In this embodiment of the invention, the nucleic acids produce their encoded antibody or fusion protein that mediates a therapeutic or prophylactic effect.

Any of the methods for gene therapy available in the art can be used according to the present invention. Exemplary methods are described below.

For general reviews of the methods of gene therapy, see Goldspiel et al., *Clinical Pharmacy*, 12:488–505, 1993; Wu and Wu, *Biotherapy*, 3:87–95, 1991; Tolstoshev, *Ann. Rev. Pharmacol. Toxicol.*, 32:573–596, 1993; Mulligan, *Science*, 260:926–932, 1993; and Morgan and Anderson, *Ann. Rev. biochem.* 62:191–217, 1993; *TIBTECH* 11(5):155–215, 1993. Methods commonly known in the art of recombinant DNA technology which can be used are described in Ausubel et al. (eds.), Current Protocols in Molecular Biology, John Wiley & Sons, NY (1993); and Kriegler, Gene Transfer and Expression, A Laboratory Manual, Stockton Press, NY (1990).

In a preferred aspect, a composition of the invention comprises nucleic acids encoding an antibody, said nucleic acids being part of an expression vector that expresses the antibody in a suitable host. In particular, such nucleic acids have promoters, preferably heterologous promoters, operably linked to the antibody coding region, said promoter being inducible or constitutive, and, optionally, tissue-specific. In another particular embodiment, nucleic acid molecules are used in which the antibody coding sequences and any other desired sequences are flanked by regions that promote homologous recombination at a desired site in the genome, thus providing for intrachromosomal expression of the antibody encoding nucleic acids (Koller and Smithies, Proc. Natl. Acad. Sci. USA, 86:8932–8935, 1989; and Zijlstra et al., *Nature*, 342:435–438, 1989).

In another preferred aspect, a composition of the invention comprises nucleic acids encoding a fusion protein, said nucleic acids being a part of an expression vector that expression the fusion protein in a suitable host. In particular, such nucleic acids have promoters, preferably heterologous promoters, operably linked to the coding region of a fusion protein, said promoter being inducible or constitutive, and optionally, tissue-specific. In another particular embodiment, nucleic acid molecules are used in which the coding sequence of the fusion protein and any other desired sequences are flanked by regions that promote homologous recombination at a desired site in the genome, thus providing for intrachromosomal expression of the fusion protein encoding nucleic acids.

Delivery of the nucleic acids into a subject may be either direct, in which case the subject is directly exposed to the nucleic acid or nucleic acid-carrying vectors, or indirect, in which case, cells are first transformed with the nucleic acids in vitro, then transplanted into the subject. These two approaches are known, respectively, as in vivo or ex vivo gene therapy.

In a specific embodiment, the nucleic acid sequences are directly administered in vivo, where it is expressed to produce the encoded product. This can be accomplished by any of numerous methods known in the art, e.g., by constructing them as part of an appropriate nucleic acid expression vector and administering it so that they become intracellular, e.g., by infection using defective or attenuated retroviral or other viral vectors (see U.S. Pat. No. 4,980, 286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu and Wu, *J. Biol. Chem.*, 262:4429–4432, 1987) (which can be used to target cell types specifically expressing the receptors), etc. In another embodiment, nucleic acid-ligand complexes can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180; WO 92/22635; WO 92/20316; WO 93/14188; WO 93/20221). Alternatively, the nucleic acid can be introduced intracellularly and incorporated within host cell DNA for expression, by homologous recombination (Koller and Smithies, *Proc. Natl. Acad. Sci. USA*, 86:8932–8935, 1989; and Zijlstra et al., *Nature*, 342:435–438, 1989).

In a specific embodiment, viral vectors that contain nucleic acid sequences encoding an antibody or a fusion protein are used. For example, a retroviral vector can be used (see Miller et al., *Meth. Enzymol.*, 217:581–599, 1993). These retroviral vectors contain the components necessary for the correct packaging of the viral genome and integration into the host cell DNA. The nucleic acid sequences encoding the antibody or a fusion protein to be used in gene therapy are cloned into one or more vectors, which facilitates delivery of the nucleotide sequence into a subject. More detail about retroviral vectors can be found in Boesen et al., *Biotherapy*, 6:291–302, 1994, which describes the use of a retroviral vector to deliver the mdr 1 gene to hematopoietic stem cells in order to make the stem cells more resistant to chemotherapy. Other references illustrating the use of retroviral vectors in gene therapy are: Clowes et al., *J. Clin. Invest.*, 93:644–651, 1994; Klein et al., *Blood* 83:1467–1473, 1994; Salmons and Gunzberg, *Human Gene Therapy*, 4:129–141, 1993; and Grossman and Wilson, *Curr. Opin. in Genetics and Devel.*, 3:110–114, 1993.

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, *Current Opinion in Genetics and Development*, 3:499–503, 1993, present a review of adenovirus-based gene therapy. Bout et al., *Human Gene Therapy*, 5:3–10, 1994, demonstrated the use of adenovirus vectors to transfer genes to the respiratory epithelia of rhesus monkeys. Other instances of the use of adenoviruses in gene therapy can be found in Rosenfeld et al., *Science*, 252:431–434, 1991; Rosenfeld et al., *Cell*, 68:143–155, 1992; Mastrangeli et al., *J. Clin. Invest.*, 91:225–234, 1993; PCT Publication WO 94/12649; and Wang et al., *Gene Therapy*, 2:775–783, 1995. In a preferred embodiment, adenovirus vectors are used.

Adeno-associated virus (AAV) has also been proposed for use in gene therapy (see, e.g.,Walsh et al., *Proc. Soc. Exp. Biol. Med.*, 204:289–300, 1993, and U.S. Pat. No. 5,436, 146).

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a subject.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcellmediated gene transfer, spheroplast fusion, etc. Numerous techniques are known in the art for the introduction of foreign genes into cells (see, e.g., Loeffler and Behr, *Meth. Enzymol.*, 217:599–618, 1993; Cohen et al., *Meth. Enzymol.*, 217:618–644, 1993; and *Clin. Pharma. Ther.*, 29:69–92, 1985) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a subject by various methods known in the art. Recombinant blood cells (e.g., hematopoietic stem or progenitor cells) are preferably administered intravenously. The amount of cells envisioned for use depends on the desired effect, patient state, etc., and can be determined by one skilled in the art.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as T lymphocytes, B lymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc.

In a preferred embodiment, the cell used for gene therapy is autologous to the subject.

In an embodiment in which recombinant cells are used in gene therapy, nucleic acid sequences encoding an antibody or a fusion protein are introduced into the cells such that they are expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention (see e.g., PCT Publication WO 94/08598; Stemple and Anderson, *Cell*, 7 1:973–985, 1992; Rheinwald, *Meth. Cell Bio.*, 21A: 229, 1980; and Pittelkow and Scott, *Mayo Clinic Proc.*, 61:771, 1986).

In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription.

5.8. Characterization and Demonstration of Therapeutic or Prophylactic Utility Antibodies, fusion proteins, and conjugated molecules of the present invention may be characterized in a variety of ways. In particular, antibodies of the invention may be assayed for the ability to immunospecifically bind to an antigen. Such an assay may be performed in solution (e.g., Houghten, *Bio/Techniques*, 13:412–421, 1992), on beads (Lam, *Nature*, 354:82–84, 1991, on chips (Fodor, *Nature*, 364:555–556, 1993), on bacteria (U.S. Pat. No. 5,223,409), on spores (U.S. Pat. Nos. 5,571,698; 5,403,484; and 5,223, 409), on plasmids (Cull et al., *Proc. Natl. Acad. Sci. USA*, 89:1865–1869, 1992) or on phage (Scott and Smith, *Science*, 249:386–390, 1990; Devlin, *Science*, 249:404–406, 1990; Cwirla et al., *Proc. Natl. Acad. Sci. USA*, 87:6378–6382, 1990; and Felici, *J. Mol. Biol.*, 222:301–310, 1991) (each of these references is incorporated herein in its entirety by reference). Antibodies that have been identified to immunospecifically bind to an antigen or a fragment thereof can then be assayed for their specificity affinity for the antigen.

The antibodies of the invention or fragments thereof may be assayed for immunospecific binding to an antigen and cross-reactivity with other antigens by any method known in the art. Immunoassays which can be used to analyze immunospecific binding and cross-reactivity include, but are not limited to, competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g, Ausubel et al, eds, 1994, Current Protocols in Molecular Biology, Vol. 1, John Wiley & Sons, Inc., New York, which is incorporated by reference herein in its entirety). Exemplary immunoassays are described briefly below (but are not intended by way of limitation).

Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding the antibody of interest to the cell lysate, incubating for a period of time (e.g., 1 to 4 hours) at 40° C., adding protein A and/or protein G sepharose beads to the cell lysate, incubating for about an hour or more at 40° C., washing the beads in lysis buffer and resuspending the beads in SDS/sample buffer. The ability of the antibody of interest to immunoprecipitate a particular antigen can be assessed by, e.g., western blot analysis. One of skill in the art would be knowledgeable as to the parameters that can be modified to increase the binding of the antibody to an antigen and decrease the background (e.g., pre-clearing the cell lysate with sepharose beads). For further discussion regarding immunoprecipitation protocols see, e.g., Ausubel et al, eds, 1994, Current Protocols in Molecular Biology, Vol. 1, John Wiley & Sons, Inc., New York at 10.16.1.

Western blot analysis generally comprises preparing protein samples, electrophoresis of the protein samples in a polyacrylamide gel (e.g., 8%–20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), blocking the membrane with primary antibody (the antibody of interest) diluted in blocking buffer, washing the membrane in washing buffer, blocking the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., $^{32}P$ or $^{125}I$) diluted in blocking buffer, washing the membrane in wash buffer, and detecting the presence of the antigen. One of skill in the art would be knowledgeable as to the parameters that can be modified to increase the signal detected and to reduce the background noise. For further discussion regarding western blot protocols see, e.g., Ausubel et al, eds, 1994, Current Protocols in Molecular Biology, Vol. 1, John Wiley & Sons, Inc., New York at 10.8.1.

ELISAs comprise preparing antigen, coating the well of a 96 well microtiter plate with the antigen, adding the antibody of interest conjugated to a detectable compound such as an enzymatic substrate (e.g., horseradish peroxidase or alkaline phosphatase) to the well and incubating for a period of time, and detecting the presence of the antigen. In ELISAs the antibody of interest does not have to be conjugated to a detectable compound; instead, a second antibody (which recognizes the antibody of interest) conjugated to a detectable compound may be added to the well. Further, instead of coating the well with the antigen, the antibody may be coated to the well. In this case, a second antibody conjugated to a detectable compound may be added following the addition of the antigen of interest to the coated well. One of skill in the art would be knowledgeable as to the parameters that can be modified to increase the signal detected as well as other variations of ELISAs known in the art. For further discussion regarding ELISAs see, e.g., Ausubel et al, eds, 1994, Current Protocols in Molecular Biology, Vol. 1, John Wiley & Sons, Inc., New York at 11.2.1.

The binding affinity of an antibody to an antigen and the off-rate of an antibody-antigen interaction can be determined by competitive binding assays. One example of a competitive binding assay is a radioimmunoassay comprising the incubation of labeled antigen (e.g., $^3H$ or $^{125}I$) with the antibody of interest in the presence of increasing amounts of unlabeled antigen, and the detection of the antibody bound to the labeled antigen. The affinity of the antibody of the present invention or a fragment thereof for the antigen and the binding off-rates can be determined from the saturation data by scatchard analysis. Competition with a second antibody can also be determined using radioimmunoassays. In this case, the antigen is incubated with an antibody of the present invention or a fragment thereof conjugated to a labeled compound (e.g., $^3H$ or $^{125}I$) in the presence of increasing amounts of an unlabeled second antibody.

In a preferred embodiment, BIAcore kinetic analysis is used to determine the binding on and off rates of antibodies to an antigen. BIAcore kinetic analysis comprises analyzing the binding and dissociation of an antigen from chips with immobilized antibodies on their surface (see the Example section infra).

The antibodies of the invention as well as fusion proteins and conjugated molecules can also be assayed for their ability to inhibit the binding of an antigen to its host cell receptor using techniques known to those of skill in the art. For example, cells expressing the receptor for a viral antigen can be contacted with virus in the presence or absence of an antibody and the ability of the antibody to inhibit viral antigen's binding can measured by, for example, flow cytometry or a scintillation counter. The antigen or the antibody can be labeled with a detectable compound such as a radioactive label (e.g. $^{32}P$, $^{35}S$, and $^{125}I$) or a fluorescent label (e.g., fluorescein isothiocyanate, rhodamine, phycoerythrin, phycocyanin, allophycocyanin, o-phthaldehyde and fluorescamine) to enable detection of an interaction between the antigen and its host cell receptor. Alternatively, the ability of antibodies to inhibit an antigen from binding to its receptor can be determined in cell-free assays. For example, virus or a viral antigen (e.g., RSV F glycoprotein) can be contacted in a cell-free assay with an antibody and the ability of the antibody to inhibit the virus or the viral antigen from binding to its host cell receptor can be determined. Preferably, the antibody is immobilized on a solid support and the antigen is labeled with a detectable compound. Alternatively, the antigen is immobilized on a solid support and the antibody is labeled with a detectable compound. The antigen may be partially or completely purified (e.g., partially or completely free of other polypeptides) or part of a cell lysate. Further, the antigen may be a fusion protein comprising the viral antigen and a domain such as glutathione-S-transferase. Alternatively, an antigen can be biotinylated using techniques well known to those of skill in the art (e.g, biotinylation kit, Pierce Chemicals; Rockford, Ill.).

The antibodies, fusion proteins, and conjugated molecules of the invention can also be assayed for their ability to inhibit or downregulate viral or bacterial replication using techniques known to those of skill in the art. For example, viral replication can be assayed by a plaque assay such as described, e.g., by Johnson et al., *Journal of Infectious Diseases,* 176:1215–1224, 1997. The antibodies, fusion proteins, and conjugated molecules of the invention of the invention can also be assayed for their ability to inhibit or downregulate the expression of viral or bacterial polypeptides. Techniques known to those of skill in the art, including, but not limited to, Western blot analysis, Northern blot analysis, and RT-PCR, can be used to measure the expression of viral or bacterial polypeptides. Further, the antibodies, fusion proteins, and conjugated molecules of the invention of the invention can be assayed for their ability to prevent the formation of syncytia.

The antibodies, fusion proteins, conjugated molecules, and compositions of the invention are preferably tested in vitro, and then in vivo for the desired therapeutic or prophylactic activity, prior to use in humans. For example, in vitro assays which can be used to determine whether administration of a specific antibody, a specific fusion protein, a specific conjugated molecule, or a composition of the present invention is indicated, include in vitro cell culture assays in which a subject tissue sample is grown in culture, and exposed to or otherwise administered an antibody, a fusion protein, conjugated molecule, or composition of the present invention, and the effect of such an antibody, a fusion protein, conjugated molecule, or a composition of the present invention upon the tissue sample is observed. In various specific embodiments, in vitro assays can be carried out with representative cells of cell types involved in a disease or disorder, to determine if an antibody, a fusion protein, conjugated molecule, or composition of the present invention has a desired effect upon such cell types. Preferably, the antibodies, the fusion proteins, the conjugated molecules, or compositions of the invention are also tested in in vitro assays and animal model systems prior to administration to humans.

Antibodies, fusion proteins, conjugated molecules, or compositions of the present invention for use in therapy can be tested for their toxicity in suitable animal model systems, including but not limited to rats, mice, cows, monkeys, and rabbits. For in vivo testing for the toxicity of an antibody, a fusion protein, a conjugated molecule, or a composition, any animal model system known in the art may be used.

Efficacy in treating or preventing viral infection may be demonstrated by detecting the ability of an antibody, a fusion protein, a conjugated molecule, or a composition of the invention to inhibit the replication of the virus, to inhibit transmission or prevent the virus from establishing itself in its host, or to prevent, ameliorate or alleviate one or more symptoms associated with viral infection. The treatment is considered therapeutic if there is, for example, a reduction is viral load, amelioration of one or more symptoms or a decrease in mortality and/or morbidity following administration of an antibody, a fusion protein, a conjugated molecule, or a composition of the invention. Antibodies, fusion proteins, conjugated molecules, or compositions of the invention can also be tested for their ability to inhibit viral replication or reduce viral load in in vitro and in vivo assays.

Efficacy in treating or preventing bacterial infection may be demonstrated by detecting the ability of an antibody, a fusion protein or a composition of the invention to inhibit the bacterial replication, or to prevent, ameliorate or alleviate one or more symptoms associated with bacterial infection. The treatment is considered therapeutic if there is, for example, a reduction is bacterial numbers, amelioration of one or more symptoms or a decrease in mortality and/or morbidity following administration of an antibody, a fusion protein or a composition of the invention.

Efficacy in treating cancer may be demonstrated by detecting the ability of an antibody, a fusion protein, a conjugated molecule, or a composition of the invention to inhibit or reduce the growth or metastasis of cancerous cells or to ameliorate or alleviate one or more symptoms associated with cancer. The treatment is considered therapeutic if there is, for example, a reduction in the growth or metastasis of cancerous cells, amelioration of one or more symptoms associated with cancer, or a decrease in mortality and/or morbidity following administration of an antibody, a fusion protein, a conjugated molecule, or a composition of the invention. Antibodies, fusion proteins or compositions of the invention can be tested for their ability to reduce tumor formation in in vitro, ex vivo, and in vivo assays.

Efficacy in treating inflammatory disorders may be demonstrated by detecting the ability of an antibody, a fusion protein, a conjugated molecule, or a composition of the invention to reduce or inhibit the inflammation in an animal or to ameliorate or alleviate one or more symptoms associated with an inflammatory disorder. The treatment is considered therapeutic if there is, for example, a reduction is in inflammation or amelioration of one or more symptoms following administration of an antibody, a fusion proteins, a conjugated molecule, or a composition of the invention.

Antibodies, fusion proteins, conjugated molecules, or compositions of the invention can be tested in vitro and in vivo for the ability to induce the expression of cytokines (e.g., IFN-α, IFN-β, IFN-γ, IL-2, IL-3, IL-4, IL-5, IL-6, IL10, IL-12, and IL-15) and activation markers (e.g., CD28, ICOS, and SLAM). Techniques known to those of skill in the art can be used to measure the level of expression of cytokines and activation markers. For example, the level of expression of cytokines can be measured by analyzing the level of RNA of cytokines by, for example, RT-PCR and Northern blot analysis, and by analyzing the level of cytokines by, for example, immunoprecipitation followed by Western blot analysis or ELISA.

Antibodies, fusion proteins, conjugated molecules, or compositions of the invention can be tested in vitro and in vivo for their ability to modulate the biological activity of immune cells, preferably human immune cells (e.g., T-cells, B-cells, and Natural Killer cells). The ability of an antibody, a fusion protein, a conjugated molecule, or a composition of the invention to modulate the biological activity of immune cells can be assessed by detecting the expression of antigens, detecting the proliferation of immune cells, detecting the activation of signaling molecules, detecting the effector function of immune cells, or detecting the differentiation of immune cells. Techniques known to those of skill in the art can be used for measuring these activities. For example, cellular proliferation can be assayed by $^3$H-thymidine incorporation assays and trypan blue cell counts. Antigen expression can be assayed, for example, by immunoassays including, but are not limited to, competitive and non-competitive assay systems using techniques such as Western blots, immunohistochemistry, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays and FACS analysis. The activation of signaling molecules can be assayed, for example, by kinase assays and electrophoretic shift assays (EMSAs).

Antibodies, fusion proteins, conjugated molecules, or compositions of the invention can also be tested for their ability to increase the survival period of animals, preferably mammals and most preferably humans, suffering from a disease, disorder, or infection by at least 25%, preferably at least 50%, at least 60%, at least 75%, at least 85%, at least 95%, or at least 99%. Further, antibodies, fusion proteins, conjugated molecules, or compositions of the invention can be tested for their ability reduce the hospitalization period of animals, preferably mammals and most preferably humans, suffering from a disease, disorder, or infection by at least 60%, preferably at least 75%, at least 85%, at least 95%, or at least 99%. Techniques known to those of skill in the art can be used to analyze the function of the antibodies or compositions of the invention in vivo.

5.9. Diagnostic Uses of Antibodies and Fusion Proteins

Labeled antibodies, fusion proteins, and conjugated molecules of the invention can be used for diagnostic purposes to detect, diagnose, or monitor diseases, disorders or infections. The invention provides for the detection or diagnosis of a disease, disorder or infection, comprising: (a) assaying the expression of an antigen in cells or a tissue sample of a subject using one or more antibodies that immunospecifically bind to the antigen; and (b) comparing the level of the antigen with a control level, e.g, levels in normal tissue samples, whereby an increase in the assayed level of antigen compared to the control level of the antigen is indicative of the disease, disorder or infection. The invention also provides for the detection or diagnosis of a disease, disorder or infection, comprising (a) assaying the expression of an antigen in cells or a tissue sample of a subject using one or fusion proteins or conjugated molecules of the invention that bind to the antigen; and (b) comparing the level of the antigen with a control level, e.g., levels in normal tissue samples, whereby an increase of antigen compared to the control level of the antigen is indicative of the disease, disorder or infection. Accordingly, the fusion protein or conjugated molecule comprises a bioactive molecule such as a ligand, cytokine or growth factor and the hinge-Fc region or fragments thereof, wherein the fusion protein or conjugated molecule is capable of binding to an antigen being detected.

Antibodies of the invention can be used to assay antigen levels in a biological sample using classical immunohistological methods as described herein or as known to those of skill in the art (e.g., see Jalkanen et al., *J. Cell. Biol.*, 101:976–985, 1985; Jalkanen et al., *J. Cell. Biol.*, 105: 3087–3096, 1987). Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, alkaline phosphatase, glucose oxidase; radioisotopes, such as iodine ($^{125}$I, $^{131}$I), carbon ($^{14}$C), sulfur ($^{35}$S), tritium ($^{3}$H), indium ($^{121}$In), and technetium ($^{99m}$Tc); luminescent labels, such as luminol; and fluorescent labels, such as fluorescein and rhodamine.

Fusion proteins can be used to assay antigen levels in a biological sample using, for example, SDS-PAGE and immunoassays known to those of skill in the art.

One aspect of the invention is the detection and diagnosis of a disease, disorder, or infection in a human. In one embodiment, diagnosis comprises: a) administering (for example, parenterally, subcutaneously, or intraperitoneally) to a subject an effective amount of a labeled antibody that immunospecifically binds to an antigen; b) waiting for a time interval following the administration for permitting the labeled antibody to preferentially concentrate at sites in the subject where the antigen is expressed (and for unbound labeled molecule to be cleared to background level); c) determining background level; and d) detecting the labeled antibody in the subject, such that detection of labeled antibody above the background level indicates that the subject has the disease, disorder, or infection. In accordance with this embodiment, the antibody is labeled with an imaging moiety which is detectable using an imaging system known to one of skill in the art. Background level can be determined by various methods including, comparing the amount of labeled molecule detected to a standard value previously determined for a particular system.

In another embodiment, diagnosis comprises: a) administering (for example, parenterally, subcutaneously, or intraperitoneally) to a subject an effective amount of a labeled fusion protein or conjugated molecule that binds to an antigen or some other molecule; b) waiting for a time interval following the administration for permitting the labeled fusion protein or conjugated molecule to preferentially concentrate at sites in the subject where the antigen or other molecule is expressed (and for unbound labeled molecule to be cleared to background level); c) determining background level; and d) detecting the labeled fusion protein or conjugated molecule in the subject, such that detection of labeled fusion protein above the background level indicates that the subject has the disease, disorder, or infection. In accordance with this embodiment, the fusion protein or conjugated molecule comprises a bioactive molecule such as a ligand, cytokine or growth factor and a hinge-Fc region or a fragment thereof, wherein said fusion protein or conjugated molecule is labeled with an imaging moiety and is capable of binding to the antigen being detected.

It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of $^{99m}$Tc. The labeled antibody will then preferentially accumulate at the location of cells which contain the specific protein. In vivo tumor imaging is described in S. W. Burchiel et al., "Immunopharmacokinetics of Radiolabeled Antibodies and Their Fragments," Chapter 13 in Tumor Imaging: The Radiochemical Detection of Cancer, S. W. Burchiel and B. A. Rhodes, eds., Masson Publishing Inc. (1982).

Depending on several variables, including the type of label used and the mode of administration, the time interval following the administration for permitting the labeled molecule to preferentially concentrate at sites in the subject and for unbound labeled molecule to be cleared to background level is 6 to 48 hours or 6 to 24 hours or 6 to 12 hours. In another embodiment the time interval following administration is 5 to 20 days or 5 to 10 days.

In one embodiment, monitoring of a disease, disorder or infection is carried out by repeating the method for diagnosing the disease, disorder or infection, for example, one month after initial diagnosis, six months after initial diagnosis, one year after initial diagnosis, etc.

Presence of the labeled molecule can be detected in the subject using methods known in the art for in vivo scanning. These methods depend upon the type of label used. Skilled artisans will be able to determine the appropriate method for detecting a particular label. Methods and devices that may be used in the diagnostic methods of the invention include, but are not limited to, computed tomography (CT), whole body scan such as position emission tomography (PET), magnetic resonance imaging (MRI), and sonography.

In a specific embodiment, the molecule is labeled with a radioisotope and is detected in the patient using a radiation responsive surgical instrument (Thurston et al., U.S. Pat. No. 5,441,050). In another embodiment, the molecule is labeled with a fluorescent compound and is detected in the patient using a fluorescence responsive scanning instrument. In another embodiment, the molecule is labeled with a positron emitting metal and is detected in the patient using positron emission-tomography. In yet another embodiment, the molecule is labeled with a paramagnetic label and is detected in a patient using magnetic resonance imaging (MRI).

5.10. Kits

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

The present invention provides kits that can be used in the above methods. In one embodiment, a kit comprises an antibody, fusion protein, or conjugated molecule, of the invention, preferably in a purified form, in one or more containers. In a specific embodiment, the kits of the present invention contain a substantially isolated antigen as a control. Preferably, the kits of the present invention further comprise a control antibody, fusion protein, or conjugated molecule which does not react with the antigen included in the kit. In another specific embodiment, the kits of the present invention contain a means for detecting the binding of an antibody, fusion protein, or conjugated molecule, to an antigen (e.g., the antibody, fusion protein, or conjugated molecule, may be conjugated to a detectable substrate such as a fluorescent compound, an enzymatic substrate, a radioactive compound or a luminescent compound, or a second antibody which recognizes the first antibody may be conjugated to a detectable substrate). In specific embodiments, the kit may include a recombinantly produced or chemically synthesized antigen. The antigen provided in the kit may also be attached to a solid support. In a more specific embodiment the detecting means of the above-described kit includes a solid support to which antigen is attached. Such a kit may also include a non-attached reporter-labeled anti-human antibody. In this embodiment, binding of the antibody to the antigen can be detected by binding of the said reporter-labeled antibody.

5.11 In Vitro and In Vivo Assays for Extended Half-Life of Modified IGG Hinge-FC Fragments The binding ability of modified IgGs and molecules comprising an IgG constant domain of FcRn fragment thereof to FcRn can be characterized by various in vitro assays. PCT publication WO 97/34631 by Ward discloses various methods in detail and is incorporated herein in its entirety by reference.

For example, in order to compare the ability of the modified IgG or fragments thereof to bind to FcRn with that of the wild type IgG, the modified IgG or fragments thereof and the wild type IgG can be radio-labeled and reacted with FcRn-expressing cells in vitro. The radioactivity of the cell-bound fractions can be then counted and compared. The cells expressing FcRn to be used for this assay are preferably endothelial cell lines including mouse pulmonary capillary endothelial cells (B10, D2.PCE) derived from lungs of B10.DBA/2 mice and SV40 transformed endothelial cells (SVEC) (Kim et al., *J. Immunol.*, 40:457–465, 1994) derived from C3H/HeJ mice. However, other types of cells, such as intestinal brush borders isolated from 10- to 14-day old suckling mice, which express sufficient number of FcRn can be also used. Alternatively, mammalian cells which express recombinant FcRn of a species of choice can be also utilized. After counting the radioactivity of the bound fraction of modified IgG or that of wild type, the bound molecules can be then extracted with the detergent, and the percent release per unit number of cells can be calculated and compared.

Affinity of modified IgGs for FcRn can be measured by surface plasmon resonance (SPR) measurement using, for example, a BIAcore 2000 (BIAcore Inc.) as described previously (Popov et al., *Mol. Immunol.*, 33:493–502, 1996; Karlsson et al., *J. Immunol. Methods*, 145:229–240, 1991, both of which are incorporated by reference in their entireties). In this method, FcRn molecules are coupled to a BIAcore sensor chip (e.g., CM5 chip by Pharmacia) and the binding of modified IgG to the immobilized FcRn is measured at a certain flow rate to obtain sensorgrams using BIA evaluation 2.1 software, based on which on- and off-rates of the modified IgG, constant domains, or fragments thereof, to FcRn can be calculated.

Relative affinities of modified IgGs or fragments thereof, and the wild type IgG for FcRn can be also measured by a simple competition binding assay. Unlabeled modified IgG or wild type IgG is added in different amounts to the wells of a 96-well plate in which FcRn is immobilize. A constant amount of radio-labeled wild type IgG is then added to each well. Percent radioactivity of the bound fraction is plotted against the amount of unlabeled modified IgG or wild type IgG and the relative affinity of the modified hinge-Fc can be calculated from the slope of the curve.

Furthermore, affinities of modified IgGs or fragments thereof, and the wild type IgG for FcRn can be also measured by a saturation study and the Scatchard analysis.

Transfer of modified IgG or fragments thereof across the cell by FcRn can be measured by in vitro transfer assay using radiolabeled IgG or fragments thereof and FcRn-expressing cells and comparing the radioactivity of the one side of the cell monolayer with that of the other side. Alternatively, such transfer can be measured in vivo by feeding 10- to 14-day old suckling mice with radiolabeled, modified IgG and periodically counting the radioactivity in blood samples which indicates the transfer of the IgG through the intestine to the circulation (or any other target tissue, e.g., the lungs). To test the dose-dependent inhibition of the IgG transfer through the gut, a mixture of radiolabeled and unlabeled IgG at certain ratio is given to the mice and the radioactivity of the plasma can be periodically measured (Kim et al., *Eur. J. Immunol.,* 24:2429–2434, 1994).

The half-life of modified IgG or fragments thereof can be measure by pharmacokinetic studies according to the method described by Kim et al. (*Eur. J. of Immuno.* 24:542, 1994), which is incorporated by reference herein in its entirety. According to this method, radiolabeled modified IgG or fragments thereof is injected intravenously into mice and its plasma concentration is periodically measured as a function of time, for example, at 3 minutes to 72 hours after the injection. The clearance curve thus obtained should be biphasic, that is, α-phase and β-phase. For the determination of the in vivo half-life of the modified IgGs or fragments thereof, the clearance rate in β-phase is calculated and compared with that of the wild type IgG.

6. EXAMPLES

The following examples illustrate the production, isolation, and characterization of modified hinge-Fc fragments that have longer in vivo half-lives.

6.1 Library Constuction

6.1.1 Reagents

All chemicals were of analytical grade. Restriction enzymes and DNA-modifying enzymes were purchased from New England Biolabs, Inc. (Beverly, Mass.). Oligonucleotides were synthesized by MWG Biotech, Inc. (High Point, N.C.). pCANTAB5E phagemid vector, anti-E-tag-horseradish peroxydase conjugate, TG1 *E. Coli* strain, IgG Sepharose 6 Fast Flow and HiTrap protein A columns were purchased from APBiotech, Inc. (Piscataway, N.J.). VCSM13 helper phage and the Quick change mutagenesis kit were obtained from Stratagene (La Jolla, Calif.). CJ236 *E. coli* strain was purchased from Bio-Rad (Richmond, Calif.). BCA Protein Assay Reagent Kit was obtained from Pierce (Rockford, Ill.). Lipofectamine 2000 was purchased from Invitrogen, Inc. (Carlsbad, Calif.).

6.1.2 Expression and Purification of Murine and Human FCRN

The amino acid sequences of human and mouse FeRn are SEQ ID NOs. 84 and 85, respectively (see also Firan et al., *Intern. Immunol.,* 13:993–1002, 2001 and Popov et al., *Mol. Immunol.,* 33:521–530, 1996, both of which are incorporated herein by reference in their entireties). Human FcRn was also obtained following isolation from human placenta cDNA (Clontech, Palo Alto, Calif.) of the genes for human β2-microglobulin (Kabat et al., 1991, Sequences of Proteins of Immunological Interest, U.S. Public Health Service, National Institutes of Health, Washington, D.C.) and codons −23 to 267 of the human α chain (Story et al., *J. Exp. Med.,* 180:2377–2381, 1994) using standard PCR protocols. Light and heavy chains along with their native signal sequence (Kabat et al., 1991, supra; Story et al., supra) were cloned in pFastBac DUAL and pFastBac I bacmids, respectively, and viral stocks produced in *Spodoptera frugiperda* cells (Sf9) according to the manufacturer's instructions (Invitrogen, Carlsbad, Calif.). High-Five cells were infected at a multiplicity of infection of 3 with the baculoviruses encoding α and β2 chains using commercially available protocols (Invitrogen). Recombinant human FcRn was purified as follows: supernatant of infected insect cells was dialyzed into 50 mM MES (2-N-[Morpholino]ethansulfonic acid) pH 6.0 and applied to a 10 ml human IgG Sepharose 6 Fast Flow column (APBiotech, Piscataway, N.J.). Resin was washed with 200 ml 50 mM MES pH 6.0 and FcRn eluted with 0.1 M Tris-Cl pH 8.0. Purified FcRn was dialyzed against 50 mM MES pH 6.0, flash frozen and stored at −70° C. The purity of proteins was checked by SDS-PAGE and HPLC.

6.1.3 Preparation of Taa-Containing ssDNA Uracil Template

Construction of the libraries was based on a site directed mutagenesis strategy derived from the Kunkel method (Kunkel et al., *Methods Enzymol.* 154:367–382, 1987). A human hinge-Fc gene spanning amino acid residues 226–478 (Kabat numbering, Kabat et al., 1991, supra) derived from MEDI-493 human IgG1 (Johnson et al., *J. Infect. Disease,* 176:1215–1224, 1997), was cloned into the pCANTAB5E phagemid vector as an SfiI/NotI fragment. Four libraries were generated by introducing random mutations at positions 251, 252, 254, 255, 256 (library 1), 308, 309, 311, 312, 314 (library 2), 385, 386, 387, 389 (library 3) and 428, 433, 434, 436 (library 4). Briefly, four distinct hinge-Fc templates were generated using PCR by overlap extension (Ho et al., *Gene,* 15:51–59, 1989), each containing one TAA stop codon at position 252 (library 1), 310 (library 2), 384 (library 3) or 429 (library 4), so that only mutagenized phagemids will give rise to Fc-displaying phage.

Each TAA-containing single-stranded DNA (TAAss-DNA) was then prepared as follows: a single CJ236 *E. coli* colony harboring one of the four relevant TAA-containing phagemids was grown in 10 ml 2×YT medium supplemented with 10 µg/ml chloramphenicol and 100 µg/ml ampicillin. At $OD_{600}=1$, VCSM13 helper phage was added to a final concentration of $10^{10}$ pfu/ml. After 2 hours, the culture was transferred to 500 ml of 2×YT medium supplemented with 0.25 µg/ml uridine, 10 µg/ml chloramphenicol, 30 µg/ml kanamycin, 100 µg/ml ampicillin and grown overnight at 37° C. Phage were precipitated with PEG6000 using standard protocols (Sambrook et al., 1989, *Molecular Cloning: A Laboratory Manual*, Cold Spring Harbor Press, Cold Spring Harbor, N.Y., Vols. 1–3) and purified using the Qiaprep Spin M13 Kit (Qiagen, Valencia, Calif.) according to the manufacturer's instructions. 10 to 30 µg of each uracil-containing TAAssDNA template was then combined with 0.6 µg of the following phosphorylated oligonucleotides (randomized regions underlined) in 50 mM Tris-HCl, 10 mM $MgCl_2$, pH 7.5 in a final volume of 250 µl:

Library 1:

5'-CATGTGACCTCAGG<u>SNNSNNSNN</u>GAT<u>SNNSNN</u>GGTGTCCTTGGGTTTTGGGGGG-3' (SEQ ID NO:120)

Library 2:

5'-GCACTTGTACTCCTTGCCATTSNNCCASNNSNNGTGSNNSNNGGTGAGGACGC-3' (SEQ ID NO:121)

Library 3:
5'-GGTCTTGTAGTTSNNCTC SNNSNNSNNATTGCTCTCCC-3' (SEQ ID NO:122)

Library 4:

5'-GGCTCTTCTGCGTSNNGTGSNNSNNCAGAGCCTCATGSNNCACGGAGCATGAG-3' (SEQ ID NO:123)

where N=A, C, T or G and S=G or C.

6.1.4 Synthesis of Heteroduplex DNA

Appropriate, degenerate oligonucleotides were phosphorylated in the presence of T4 polynucleotide kinase using the standard protocol. Ten to 30 µg of ssDNA U template and 0.6 µg of phosphorylated oligonucleotide were combined in 50 mM Tris-HCl containing 10 mM $MgCl_2$, pH 7.5, to a final volume of 250 µl and incubated at 90° C. for 2 minutes, 50° C. for 3 minutes, and 20° C. for 5 minutes. Synthesis of the heteroduplex DNA was carried out by adding 30 units of both T4 DNA ligase and T7 DNA polymerase in the presence of 0.4 mM ATP, 1 mM dNTPs and 6 mM DTT and the mixture was incubated for 4 hours at 20° C. The heteroduplex DNA thus produced was then purified and desalted using Qiagen Qiaquick DNA purification Kit (Qiagen, CA).

6.1.5 Electroporation

300 µl electrocompetent TG1 E. coli cells were electroporated with 1 to 5 µg of the heteroduplex DNA in a 2.5 kV field using 200 Ω and 25 µF capacitance until a library size of $1 \times 10^8$ (library 1 and 2) or $1 \times 10^7$ (library 3 and 4) was reached. The cells were resuspended in 2 ml SOC medium and the procedure was repeated 6 to 10 times. The diversity was assessed by titration of recombinant E. coli. The pulsed cells were incubated in 50 ml SOC medium for 30 minutes at 37° C. under agitation, centrifuged, and resuspended in 500 ml 2×YT containing 100 µg/ml ampicillin and $10^{10}$ pfu/ml of VCSM13 helper phage. The culture was incubated overnight at 37° C. and the cells were pelleted by centrifugation. The phage in the supernatant which express mutated hinge-Fc portion on its GIII-coat protein were precipitated with PEG6000 as previously described (Sambrook et al., 1989, supra) and resuspended in 5 ml of 20 mM MES, pH 6.0.

6.2 Panning of the Library

Phage were panned using an ELISA-based approach. A 96-well ELISA plate was coated with 100 µl/well of 0.01 mg/ml murine FcRn in sodium carbonate buffer, pH 9.0, at 4° C. overnight and then blocked with 4% skimmed milk at 37° C. for 2 hours. In each well of the coated plate, 100–150 µl of the phage suspension (about $10^{13}$ phage in total) in 20 mM MES, pH 6.0, containing 5% milk and 0.05% Tween 20, were placed and incubated at 37° C. for two to three hours with agitation.

After the incubation, the wells were washed with 20 mM MES, pH 6.0, containing 0.2% Tween 20 and 0.3 M NaCl about thirty times at room temperature. The bound phage were eluted with 100 µl/well of PBS, pH 7.4, at 37° C. for 30 minutes.

The eluted phage were then added to the culture of exponentially growing E. coli cells and propagation was carried out overnight at 37° C. in 250 ml 2×YT supplemented with 100 µg/ml ampicillin and $10^{10}$ pfu/ml of VCSM13 helper phage. Propagated phage were collected by centrifugation followed by precipitation with PEG and the panning process was repeated up to a total of six times.

For the phage library containing mutations in residues 308–314 (H310 and W313 fixed), the phage expressing hinge-Fc region with higher affinities for FcRn were enriched by each panning process as shown in Table IV. The panning results of the library for the mutations in the residues 251–256 (I253 fixed) and that of the library for the mutations in the residues 428–436 (H429, E430, A431, L432, and H435 fixed), are shown in Tables V and VI, respectively. Furthermore, the panning results of the library for the mutations in the residues 385–389 (E388 fixed) is shown in Table VII.

TABLE IV

PANNING OF LIBRARY (RESIDUES 308–314; H310 AND W313 FIXED) pCANTAB5E-KUNKEL-muFcRn (MURINE FcRn)

| PANNING | OUTPUT | | ENRICHMENT RATIO |
|---|---|---|---|
| | +FcRn | −FcRn | |
| 1st Round | $1.1 \times 10^5$ | $0.5 \times 10^5$ | 2 |
| 2nd Round | $1 \times 10^4$ | $0.2 \times 10^4$ | 5 |
| 3rd Round | $9 \times 10^4$ | $0.3 \times 10^4$ | 30 |
| 4th Round | $3 \times 10^5$ | $2 \times 10^4$ | 15 |

TABLE V

PANNING OF LIBRARY (RESIDUES 251–256; I253 FIXED) pCANTAB5E-KUNKEL-muFcRn

| PANNING | OUTPUT | | ENRICHMENT RATIO |
|---|---|---|---|
| | +FcRn | −FcRn | |
| 1st Round | $2.5 \times 10^5$ | $1 \times 10^5$ | 2.5 |
| 2nd Round | $6 \times 10^4$ | $2 \times 10^4$ | 3.0 |
| 3rd Round | $8 \times 10^5$ | $4 \times 10^4$ | 20 |
| 4th Round | $1.2 \times 10^6$ | $5 \times 10^4$ | 24 |
| 5th Round | $3.0 \times 10^6$ | $6 \times 10^4$ | 50 |

TABLE VI

PANNING OF LIBRARY (RESIDUES 428–436;
H429, E430, A431, L432, AND H435 FIXED)
pCANTAB5E-KUNKEL-muFcRn

| PANNING | OUTPUT | | ENRICHMENT RATIO |
|---|---|---|---|
| | +FcRn | −FcRn | |
| 1st Round | $2.3 \times 10^5$ | $0.9 \times 10^5$ | 2.5 |
| 2nd Round | $3 \times 10^4$ | $1 \times 10^4$ | 3 |
| 3rd Round | $2 \times 10^5$ | $2 \times 10^4$ | 10 |
| 4th Round | $8 \times 10^5$ | $5 \times 10^4$ | 16 |

TABLE VII

PANNING OF LIBRARY (RESIDUES 385–389; E388 FIXED)
pCANTAB5E-KUNKEL-muFcRn

| PANNING | OUTPUT | | ENRICHMENT RATIO |
|---|---|---|---|
| | +FcRn | −FcRn | |
| 1st Round | $4.2 \times 10^5$ | $3.8 \times 10^5$ | 1.1 |
| 2nd Round | $5 \times 10^4$ | $0.3 \times 10^4$ | 17 |
| 3rd Round | $3.5 \times 10^5$ | $1 \times 10^4$ | 35 |
| 4th Round | $5.5 \times 10^5$ | $4 \times 10^4$ | 14 |
| 5th Round | $7.5 \times 10^5$ | $5 \times 10^4$ | 15 |
| 6th Round | $2 \times 10^6$ | $1 \times 10^5$ | 20 |

6.3 Identification of Isolated Clones from Panning

After each panning process, phage were isolated and the nucleic acids encoding the expressed peptides which bound to FcRn were sequenced by a standard sequencing method such as by dideoxynucleotide sequencing (Sanger et al., *Proc. Natl. Acad. Sci USA,* 74:5463–5467, 1977) using a ABI3000 genomic analyzer (Applied Biosystems, Foster City, Calif.).

As a result of panning, two mutants were isolated from the phage library containing mutations in residues 308–314 (H310 and W313 fixed), thirteen mutants from the library for residues 251–256 (I253 fixed), six mutants from the library for residues 428–436 (H429, E430, A431, L432, and H435 fixed), and nine mutants from the library for residues 385–389 (E388 fixed). The mutants isolated from the libraries are listed in Table VIII.

TABLE VIII

MUTANTS ISOLATED BY PANNING

| LIBRARY | MUTANTS* | |
|---|---|---|
| 251–256 | Leu Tyr Ile Thr Arg Glu | (SEQ ID NO:90) |
| | Leu *Tyr* Tyr Ile Ser Arg Thr | (SEQ ID NO:91) |
| | Leu *Tyr* Tyr Ile Ser Arg *Ser* Ser | (SEQ ID NO:92) |
| | Leu *Tyr* Tyr Ile Ser Arg *Arg* Arg | (SEQ ID NO:93) |
| | Leu *Tyr* Tyr Ile Ser Arg *Gln* Gln | (SEQ ID NO:94) |
| | Leu *Trp* Trp Ile Ser Arg Thr | (SEQ ID NO:95) |
| | Leu Tyr Ile Ser Leu Gln | (SEQ ID NO:96) |
| | Leu Phe Ile Ser Arg Asp | (SEQ ID NO:97) |
| | Leu Phe Ile Ser Arg Thr | (SEQ ID NO:98) |
| | Leu Phe Ile Ser Arg Arg | (SEQ ID NO:99) |
| | Leu Phe Ile Thr Gly Ala | (SEQ ID NO:100) |
| | Leu Ser Ile Ser Arg Glu | (SEQ ID NO:101) |
| | Arg Thr Ile Ser Ile Ser | (SEQ ID NO:102) |
| 308–314 | Thr Pro His Ser Asp Trp Leu | (SEQ ID NO:103) |
| | Ile Pro His Glu Asp Trp Leu | (SEQ ID NO:104) |
| 385–389 | Arg Thr Arg Glu Pro | (SEQ ID NO:105) |
| | *Asp* Asp *Pro* Pro Pro Gln *Ser* Ser | (SEQ ID NO:106) |

TABLE VIII-continued

MUTANTS ISOLATED BY PANNING

| LIBRARY | MUTANTS* | |
|---|---|---|
| | Ser Asp Pro Glu Pro | (SEQ ID NO:107) |
| | Thr Ser His Glu Asn | (SEQ ID NO:108) |
| | Ser Lys Ser Glu Asn | (SEQ ID NO:109) |
| | His Arg Ser Glu Asn | (SEQ ID NO:110) |
| | Lys Ile Arg Glu Asn | (SEQ ID NO:111) |
| | Gly Ile Thr Glu Ser | (SEQ ID NO:112) |
| | Ser Met Ala Glu Pro | (SEQ ID NO:113) |
| 428–436 | Met His Gln Ala Leu *Arg* Arg *Tyr* Tyr His *His* His | (SEQ ID NO:114) |
| | Met His Glu Ala Leu His Phe His His | (SEQ ID NO:115) |
| | Met His Glu Ala Leu Lys Phe His His | (SEQ ID NO:116) |
| | Met His Glu Ala Leu Ser Tyr His Arg | (SEQ ID NO:117) |
| | Thr His Glu Ala Leu His Tyr His Thr | (SEQ ID NO:118) |
| | Met His Glu Ala Leu His Tyr His Tyr | (SEQ ID NO:119) |

*Substituting residues are indicated in bold face

The underlined sequences in Table VIII correspond to sequences that occurred 10 to 20 times in the final round of panning and the sequences in italics correspond to sequences that occurred 2 to 5 times in the final round of panning. Those sequences that are neither underlined nor italicized occurred once in the final round of panning.

6.4 Expression and Purification of Soluble Mutant Hinge-FC Region

The genes encoding mutated hinge-Fc fragments are excised with appropriate restriction enzymes and recloned into an expression vector, for example, VβpelBhis (Ward, *J. Mol. Biol.*, 224:885–890, 1992). Vectors containing any other type of tag sequence, such as c-myc tag, decapeptide tag (Huse et al., *Science*, 246:1275–1281, 1989), Flag™ (Immunex) tags, can be used. Recombinant clones, such as *E. coli*, are grown and induced to express soluble hinge-Fc fragments, which can be isolated from the culture media or cell lysate after osmotic shock, based on the tag used, or by any other purification methods well known to those skilled in the art and characterized by the methods as listed below.

6.5 Construction, Production and Purification of IgG1 Variants

Representative Fc mutations such as I253A, M252Y/S254T/T256E, M252W, M252Y, M252Y/T256Q, M252F/T256D, V308T/L309P/Q311S, G385D/Q386P/N389S, G385R/Q386T/P387R/N389P, H433K/N434F/Y436H, and N434F/Y436 were incorporated into the human IgG1 MEDI-493 (SYNAGIS®) (Johnson et al., 1997, supra). The heavy chain was subjected to site-directed mutagenesis using a Quick Change Mutagenesis kit (Stratagene, La Jolla, Calif.) according to the manufacturer's instructions and sequences were verified by didoxynucleotide sequencing using a ABI3000 (Applied Biosystems, Foster City, Calif.) sequencer. The different constructions were expressed transiently in human embryonic kidney 293 cells using a CMV immediate-early promoter and dicistronic operon in which IgG1/$V_H$ is cosecreted with IgG1/$V_L$ (Johnson et al., 1997, supra). Transfection was carried out using Lipofectamine 2000 (Invitrogen, Carlsbad, Calif.) and standard protocols. IgGs were purified from the conditioned media directly on 1 ml HiTrap protein A columns according to the manufacturer's instructions (APBiotech).

6.6 Characterization of Mutated Hinge-FC Region

6.6.1 In Vitro Characterization HPLC and SDS-Page

Following the purification, general characteristics such as molecular weight and bonding characteristics of the modified hinge-Fc fragments may be studied by various methods well known to those skilled in the art, including SDS-PAGE and HPLC.

FcRn Binding Assay

Binding activity of modified hinge-Fc fragments can be measured by incubating radio-labeled wild-type hinge-Fc or modified hinge-Fc with the cells expressing either mouse or human FcRn. Typically, endothelial cell lines such as SV40 transformed endothelial cells (SVEC) (Kim et al., *J. Immunol.*, 40:457–465, 1994) are used. After incubation with the hinge-Fc fragments at 37° C. for 16–18 hours, the cells are washed with medium and then detached by incubation with 5 mM $Na_2EDTA$ in 50 mM phosphate buffer, pH 7.5, for 5 minutes. The radioactivity per $10^7$ cells is measured.

Then, the cells are resuspended in 2 ml of 2.5 mg/ml CHAPS, 0.1 M Tris-HCl pH 8.0 containing 0.3 mg/ml PMSF, 25 mg/ml pepstatin and 0.1 mg/ml aprotinin and incubated for 30 minutes at room temperature. The cell suspension is then centrifuged and the supernatant separated. The radioactivity of the supernatant is measured and used to calculate the amount of the hinge-Fc fragments extracted per $10^7$ cells.

The $K_d$ for the interaction of wild type human IgG1 with murine and human FcRn (269 and 2527 nM, respectively) agree well with the values determined by others (265 and 2350 nM, respectively, Firan et al., 2001, supra). The I253A mutation virtually abolishes binding to human and murine FcRn, as reported by others (Kim et al., *Eur. J. Immunol.*, 29:2819–2825, 1991; Shields et al., *J. Biol. Chem.*, 276: 6591–6604, 2001). This is not the result of misfolding of the antibody as this mutant retains the same specific activity than the wild type molecule (SYNAGIS®) in a microneutralization assay (Johnson et al., 1997, supra; data not shown).

Human IgG1 mutants with increased binding affinity towards both murine and human FcRn were generated (Table VIII). Improvements in complex stability were overall less marked for the human IgG1-human FcRn pair than for the human IgG1-murine FcRn compared to wild type IgG1 were 30-($\Delta\Delta G$=2.0 kcal/mol for N434F/Y436H) and 11-($\Delta\Delta G$=1.4 kcal/mol for M252Y/S254Y/S254T/T256E) fold, respectively. However, ranking of the most critical positions remain unchanged when comparing human and murine FcRn: the largest increases in IgG1-murine FcRn complex stability ($\Delta\Delta G$>1.3 kcal/mol) occurred on mutations at positions 252, 254, 256 (M252Y/S254T/T256E and M252W) and 433, 434, 436 (H433K/N434F/Y436H and N434F/Y436H). Likewise, the same mutations were found to have the most profound impact on the IgG1-human FcRn interaction and also resulted in the largest increases in complex stability ($\Delta\Delta G$>1.0 kcal/mol). Substitutions at positions 308, 309, 311, 385, 386, 387 and 389 had little or no effect on the stability of the complexes involving human or murine FcRn ($\Delta\Delta G$<0.5 kcal/mol). Residues at the center of the Fc-FcRn combining site contribute significantly more to improvement in complex stability than residues at the periphery (FIG. 9).

Figure 1:
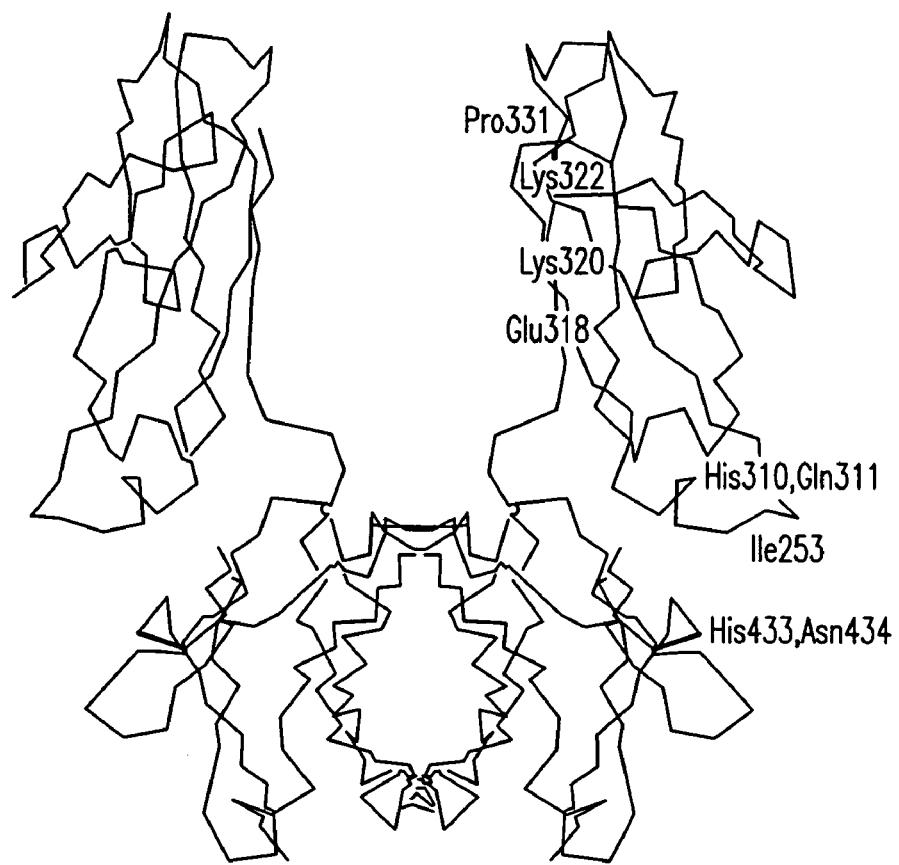
FIG. 1 shows the structure of the IgG hinge-Fc region indicating the locations of the residues identified to be involved in the interaction with the FcRn receptor (Ghetie et al., Immunology Today, 18(12):592–598, 1997).
Figure 5:
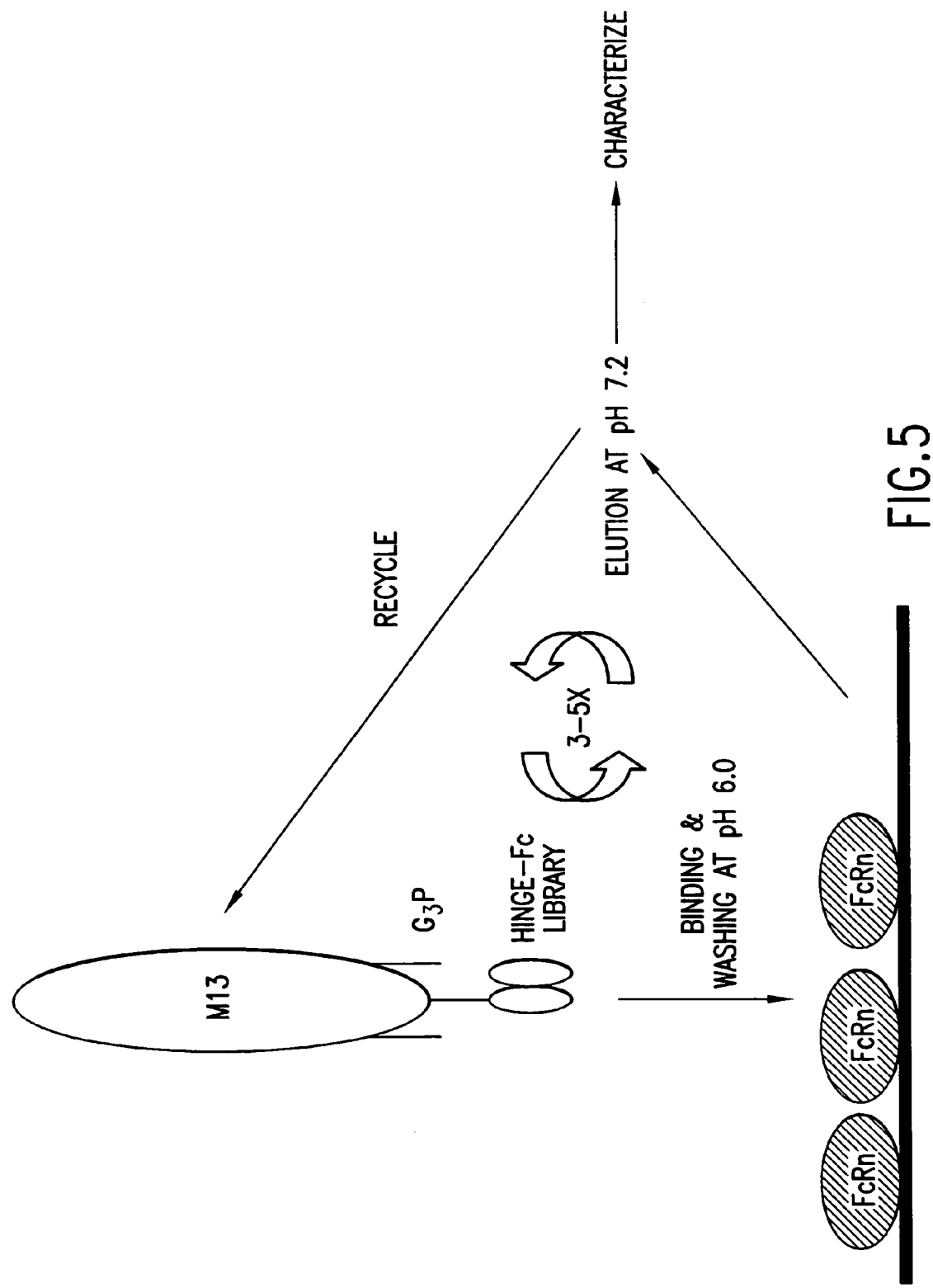
FIG. 5 shows a schematic diagram of panning process for the phage-displayed modified hinge-Fc library.
Figure 6:
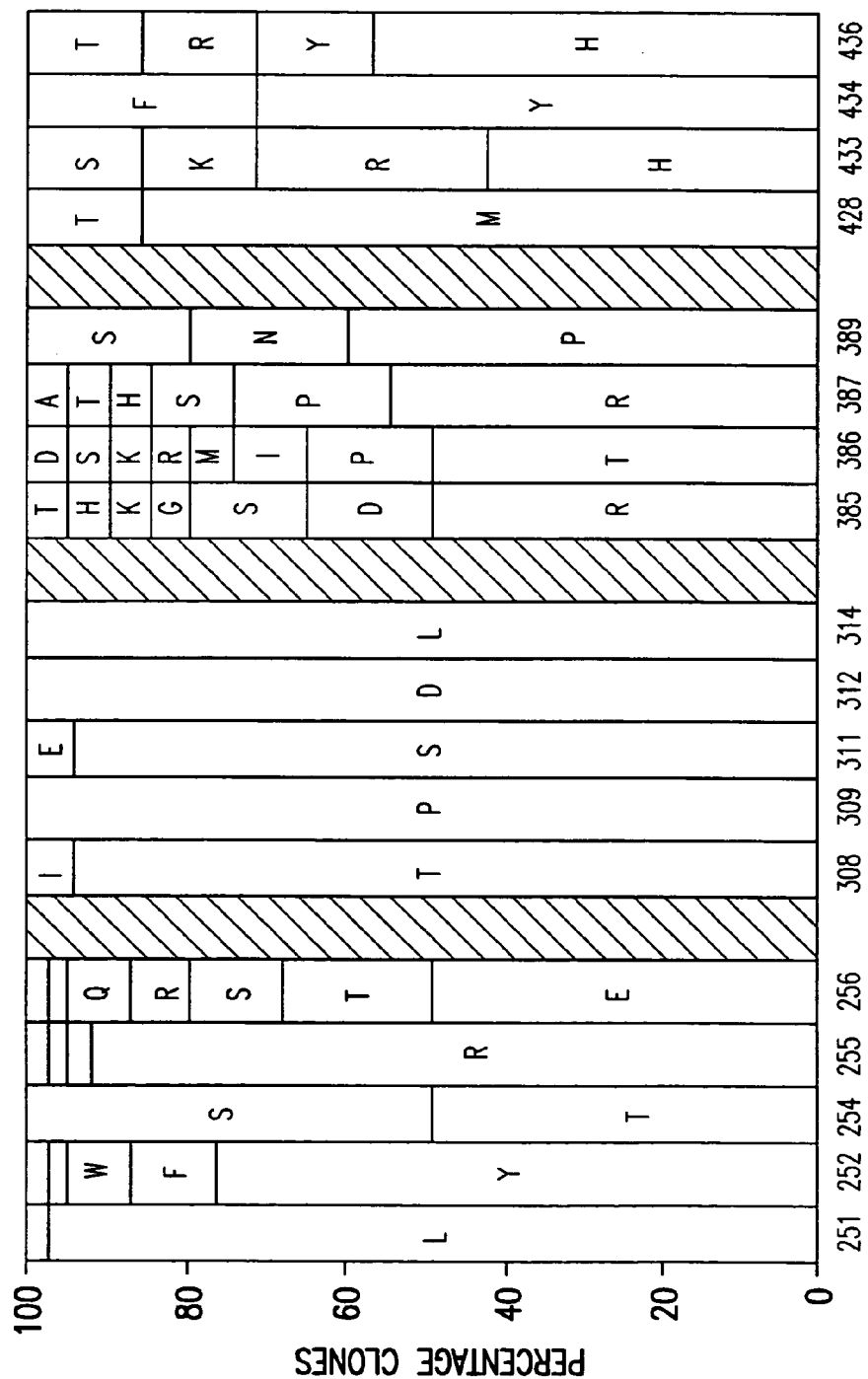
FIG. 6 shows a summary of the occurrence of selected mutant residues at the variant positions in the libraries screened.
Figure 7A:
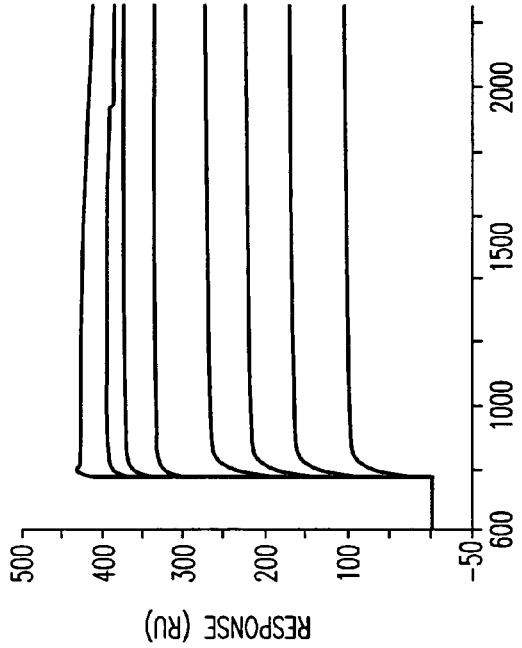
Figure 7B:
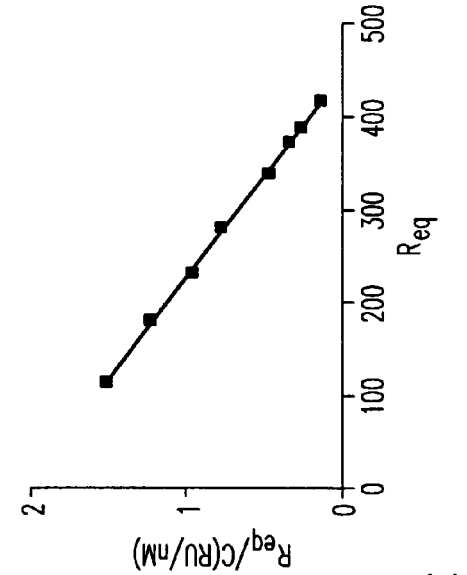
Figure 7C:
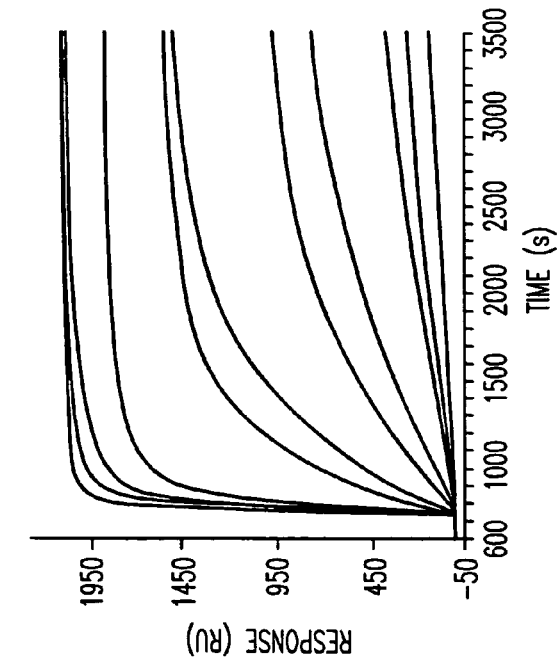
Figure 7D:
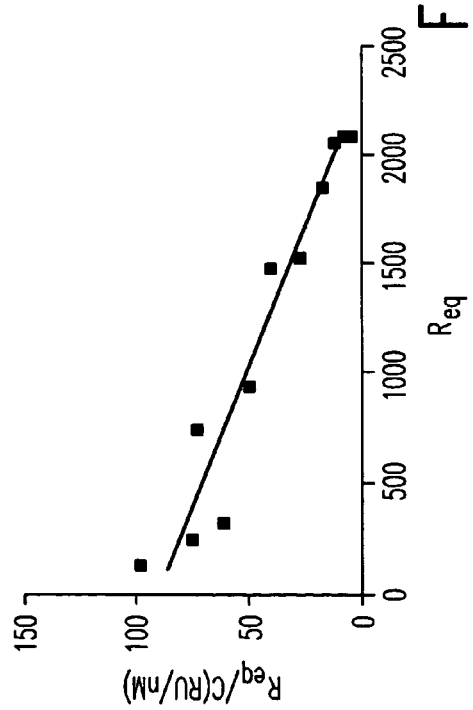

Efficient binding of human Fc to murine FcRn apparently requires the presence of several wild type Fc residues. For example, leucine is very conserved at 251, arginine at 255, aspartic acid at 310, leucine at 314 and methionine at 428 (FIG. 6). Another specificity trend is observed when one considers positions 308, 309, and 311 where threonine, proline, and serine, respectively, are very strongly favored over the corresponding wild type residues (FIG. 6). However, generation of this strong consensus sequences does not correlate with the magnitude of increase in affinity as V308T/L309P/Q311S binds less than 2-fold better than the wild type IgG1 to both human and murine FcRn (Table IX).

Increases in affinity can be strongly dependent upon residue substitution at one 'hot spot' position. For example, the single mutation M252Y causes an increase in binding to murine FcRn by 9-fold, whereas additional mutations bring little (M252Y/S254T/T256E) or no (M252Y/T256Q) added benefit. The same trend is observed for the human receptor, although to a lesser extent. Indeed, M252Y/S254T/T256E shows a marked improvement of 2.5-fold in affinity compared to M252Y. This probably reflects the differences between the binding site of human and murine FcRn (West and Bjorkman, *Biochemistry*, 39:9698–9708, 2000).

Phage-derived IgG1 mutants exhibiting a significant increase in affinity towards murine FcRn ($\Delta\Delta G$>1.3 kcal/mol) also showed significant binding activity to the receptor at pH 7.2 when compared to wild type IgG1 (FIGS. 8A–H). IgG1 mutants with moderate increase in affinity ($\Delta\Delta G$<0.3 kcal/mol) bound very poorly at pH 7.2 (data not shown). In contrast, IgG1 mutants with large ($\Delta\Delta G$>1.0 kcal/mol) increase in affinity towards human FcRn exhibited only minimal binding at pH 7.4 when compared to wild type IgG1 (FIGS. 8A–H).

TABLE IX

DISSOCIATION CONSTANTS AND RELATIVE FREE ENERGY CHANGES FOR THE BINDING OF IgG1/FC MUTANTS TO MURINE AND HUMAN FcRn*

| MUTANT | Dissociation Constant Fc/Murine FcRn (nM) | $\Delta\Delta G$ (kcal/mol) | Dissociation Constant Fc/Human FcRn (mM) | $\Delta\Delta G$ (kcal/mol) |
|---|---|---|---|---|
| wild type | 269 ± 1 | NA | 2527 ± 117 | NA |
| I253A | NB | NA | NB | NA |
| M252Y/S254T/T256E | 27 ± 6 | 1.4 | 225 ± 10 | 1.4 |
| M252W | 30 ± 1 | 1.3 | 408 ± 24 | 1.1 |
| M252Y | 41 ± 7 | 1.1 | 532 ± 37 | 0.9 |
| M252Y/T256Q | 39 ± 8 | 1.1 | 560 ± 102 | 0.9 |
| M252F/T256D | 52 ± 9 | 1.0 | 933 ± 170 | 0.6 |
| V308T/L309P/Q311S | 153 ± 23 | 0.3 | 1964 ± 84 | 0.1 |
| G385D/Q386P/N389S | 187 ± 10 | 0.2 | 2164 ± 331 | 0.1 |
| G385R/Q386T/P387R/N389P | 147 ± 24 | 0.4 | 1620 ± 61 | 0.3 |
| H433K/N434F/Y436H | 14 ± 2 | 1.8 | 399 ± 47 | 1.1 |
| N434F/Y436H | 9 ± 1 | 2.0 | 493 ± 7 | 1.0 |

*Affinity measurements were carried out by BIAcore as described above. Residue numbering is according to EU (Kabat et at., 1991, supra). Differences in free energy changes are calculated as the differences between the $\Delta g$s of wild type and mutant reactions ($\Delta\Delta G = \Delta G_{wild\ type} - \Delta G_{mutant}$). NB, no binding. NA, not-applicable.

FcRn-Mediated Transfer Assay

This assay follows the protocol disclosed in PCT publication WO 97/34631. Radiolabeled modified hinge-Fc fragments at various concentration (1 μg/ml–1 mg/ml) are added to the one side of the transwell and the transfer of the fragments mediated by FcRn-expressing monolayer of the cells can be quantitated by measuring the radioactivity on the other side of the transwell.

6.6.2 In Vivo Pharmacokinetic Study

In order to determine the half-life of the modified IgG hinge-Fc, modified hinge-Fc fragments are radiolabelled with $^{125}$I (approximate specific activity of $10^7$ cpm/μg) and dissolved in saline (pH 7.2). The solution is injected intravenously into BALB/c mice (Harlan, Indianapolis, Ind.), which have been given NaI-containing water previously to block the thyroid, in a volume not more than 150 μl and with a radioactivity of $10 \times 10^6$–$50 \times 10^6$ cpm. The mice are bled from the retro-orbital sinus at various time points, for example, at 3 minutes to 72 hours after the injection, into heparinized capillary tubes and the plasma collected from each sample is counted for radioactivity.

To generate the data provided in FIG. 10, 10 animals were used for each molecule assayed with 2.5 μg of antibody injected per animal. Antibody serum levels were determined using an anti-human IgG ELISA (FIG. 10). There seems to be an inverse correlation between affinity to mouse FcRn and persistence in serum. This might be due to the significant amount of binding of the mutants observed at pH 7.2, which leads to the sequestration (i.e., lack of release in the serum) of the molecules. Preliminary data (not shown) suggests increased transport of the mutants to the lung. Additionally, since the mutants exhibit lower levels of binding to human FcRn than murine FcRn (see FIGS. 8A–H), antibody serum levels are expected to be higher in primates and humans.

6.6.3 Surface Plasmon Resonance Analyses

The interaction of soluble murine and human FcRn with immobilized human IgG1 variants was monitored by surface plasmon resonance detection using a BIAcore 3000 instrument (Pharmacia Biosensor, Uppsala, Sweden). No aggregated material which could interfere with affinity measurements (van der Merwe et al., *EMBO J.,* 12:4945–4954, 1993; van der Merwe et al., *Biochemistry,* 33:10149–10160, 1994) was detected by gel filtration. Protein concentrations were calculated by the bicinchoninic acid (BCA) method for both human and murine FcRn or using the 1% extinction coefficient at 280 nm of 1.5 for IgG1 wild type and variants. The latter were coupled to the dextran matrix of a CM5 sensor chip (Pharmacia Biosensor) using an Amine Coupling Kit as described (Johnson et al., supra). The protein concentrations ranged from 3–5 μg/ml in 10 mM sodium acetate, pH 5.0. The activation period was set for 7 minutes at a flow rate of 10 μl/min and the immobilization period was set to between 10 and 20 minutes at a flow rate of 10 μl/min. Excess reactive esters were quenched by injection of 70 μl of 1.0 methanolamine hydrochloride, pH 8.5. This typically resulted in the immobilization of between 500 and 4000 resonance units (RU). Human and murine FcRn were buffer exchanged against 50 mM PBS buffer pH 6.0 containing 0.05% Tween 20. Dilutions were made in the same buffer. All binding experiments were performed at 25° C. with concentrations ranging from 120 to 1 μg/ml at a flow rate of 5 to 10 μl/min; data were collected for 25 to 50 minutes and three 1-minute pulses of PBS buffer pH 7.2 were used to regenerate the surfaces. FcRn was also flowed over an uncoated cell and the sensorgrams from these blank runs subtracted from those obtained with IgG1-coupled chips. Runs were analyzed using the software BIAevaluation 3.1 (Pharmacia). Association constants ($K_A$S) were determined from Scatchard analysis by measuring the concentration of free reactants and complex at equilibrium after correction for nonspecific binding. In equilibrium binding BIAcore experiments (Karlsson et al., 1991, supra; van der Merwe et al., 1993, supra; van der Merwe et al., 1994, supra; Raghavan et al., *Immunity,* 1:303–315, 1994; Malchiodi et al., *J. Exp. Med.,* 182:1833–1845, 1995), the concentration of the complex can be assessed directly as the steady-state response. The concentration of free analyte (human or murine FcRn) is equal to the bulk analyte concentration since analyte is constantly replenished during sample injection. The concentration of free ligand on the surface of the sensor chip can be derived from the concentration of the complex and from the total binding capacity of the surface as $K_A=R_{eq}/C(R_{max}-R_{eq})$ where C is the free analyte concentration, $R_{eq}$ is the steady-state response, and $R_{max}$ is the total surface binding capacity. Rearranging, the equation reads: $R_{eq}/C=K_A R_{max}-K_A R_{eq}$.

A plot of $R_{eq}/C$ versus $R_{eq}$ at different analyte concentrations thus gives a straight line from which $K_A$ can be calculated (see Table IX). Errors were estimated as the standard deviation for two or three independent determinations and were <20%.

Representative mutations identified after panning libraries 1 through 4 (FIG. 6, Table VIII) were introduced into the Fc portion of a human IgG1. Injection of different concentrations of human or murine FcRn over the immobilized IgG1 variants gave concentration-dependent binding. Typical resonance profiles for equilibrium binding of the mutant M252Y/S254T/T256E to murine and human FcRn are shown in FIGS. 7A and B. To estimate apparent $K_A$s, concentrations of FcRn ranging from 120 to 1 μg/ml were used. In all cases, equilibrium (or near-equilibrium) binding levels were reached within 50 minutes. To estimate the increase in RU resulting from the non specific effect of protein on the bulk refractive index, binding of FcRn to an uncoated cell was measured and the sensorgrams from these blank runs subtracted from those obtained with IgG1-coupled chips. The scatchard plots for the binding of the mutant M252Y/S254T/T256E to murine and human FcRn are shown in FIGS. 7C and D. The plots were all linear, and apparent $K_A$S were calculated from the relevant slopes. Measurements were carried out in duplicate or triplicate and confirmed that the immobilized IgGs retained their original binding activity.

Since there are two non-equivalent binding sites on mouse IgG1 for murine FcRn with affinities of <130 nM and 6 μM (Sanchez et al., *Biochemistry,* 38:9471–9476, 1999; Schuck et al., *Mol. Immunol.,* 36:1117–1125, 1999; Ghetie and Ward, *Ann. Rev. Immunol.,* 18:739–766, 2000), the receptor was used in solution to avoid avidity effects that arise when IgG1 binds to immobilized FcRn. Consistent with this, systematically higher affinities are observed when FcRn, rather than IgG, immobilized on the biosensor chip (Popov et al., 1996, supra; Vaughn and Bjorkman, *Biochemistry,* 36:9374–9380, 1997; Martin and Bjorkman, *Biochemistry,* 38:12639–12647; West and Bjorkman, *Biochemistry,* 39:9698–9708, 2000). Under our experimental BIAcore conditions, mainly interactions corresponding to the higher-affinity association (i.e. single liganded-recptor) are measured, according for the linearity of the scatchard plots (FIGS. 7C and D).

BIAcore analysis was also used to compare the affinity of wild type IgG1 and IgG1 mutants. Phage-derived IgG1 mutants exhibiting a significant increase in affinity towards murine FcRn at pH 6.0 ($\Delta\Delta G \geqq 1.0$ kcal/mol) also shoed significant binding to the mouse receptor at pH 7.2 with SPR $signal_{pH7.4}$/SPR $signal_{pH6.0}$>0.6 at saturation. IgG1 mutants with moderate increase in affinity towards murine FcRn at pH 6.0 ($\Delta\Delta G$<0.4 kcal/mol) bound very poorly to the mouse receptor at pH 7.2. In contrast, IgG1 mutants exhibiting large affinity increase towards human FcRn at pH 6.0 ($\Delta\Delta G \geqq 1.0$ kcal/mol) only showed minimal binding to the human receptor at pH 7.4 with SPR $signal_{pH7.4}$/SPR $signal_{pH6.0}$<0.15 at saturation.

Those skilled in the art will recognize, or be able to ascertain using no more routine experimentation, many equivalents to the specific embodiments of the invention described herein. Such equivalents are intended to be encompassed by the following claims.

All publications, patents and patent applications mentioned in this specification are herein incorporated by reference into the specification to the same extent as if each individual publication, patent or patent application was specifically and individually indicated to be incorporated herein by reference.

What is claimed is:

1. A modified IgG comprising a human IgG constant domain comprising one or more amino acid substitutions relative to a wild-type human IgG constant domain at one or more of amino acid residues 251–256, 285–290, 308–314, 385–389 and 428–436, numbered according to the EU index as in Kabat, wherein the modified IgG has an increased half-life compared to the half-life of an IgG having the wild-type human IgG constant domain, and wherein at least one of the amino acid substitutions is at amino acid residue 252, 254, 256, 309, 311, 433 or 434, and an amino acid substitution at amino acid residue 252 is a substitution with tyrosine, phenylalanine, tryptophan or threonine, an amino acid substitution at amino acid residue 254 is a substitution with threonine, an amino acid substitution at amino acid residue 256 is a substitution with serine, arginine, glutamine, glutamic acid, aspartic acid, or threonine, an amino acid substitution at amino acid residue 309 is a substitution with proline, an amino acid substitution at amino acid residue 311 is a substitution with serine, an amino acid substitution at amino acid residue 433 is a substitution with arginine, serine, isoleucine, proline, or glutamine, and an amino acid substitution at amino acid residue 434 is a substitution with histidine, phenylalanine, or tyrosine.

2. A modified IgG comprising a human IgG constant domain comprising amino acid substitutions relative to a wild-type human IgG constant domain at amino acid residues 252, 254 and 256, numbered according to the EU index as in Kabat, wherein the modified IgG has an increased half-life compared to the half-life of an IgG having the wild-type human IgG constant domain, and wherein the amino acid substitution at amino acid residue 252 is a substitution with tyrosine, the amino acid substitution at amino acid residue 254 is a substitution with threonine, and the amino acid substitution at amino acid residue 256 is a substitution with glutamic acid.

3. A modified IgG comprising a human IgG constant domain comprising amino acid substitutions relative to a wild-type human IgG constant domain at amino acid residues 252, 254, 256, 433, 434 and 436, numbered according to the EU index as in Kabat, wherein the modified IgG has an increased half-life compared to the half-life of an IgG having the wild-type human IgG constant domain, and wherein the amino acid substitution at amino acid residue 252 is a substitution with tyrosine, the amino acid substitution at amino acid residue 254 is a substitution with threonine, the amino acid substitution at amino acid residue 256 is glutamic acid, the amino acid substitution at amino acid residue 433 is a substitution with lysine, the amino acid substitution at amino acid residue 434 is a substitution with phenylalanine, and the amino acid substitution at amino acid residue 436 is a substitution with histidine.

4. A modified IgG comprising a non-human LgG constant domain comprising one or more amino acid substitutions relative to a wild-type non-human IgG constant domain at one or more amino acid residues 251–256, 285–290, 308–314, 385–389 and 428–436, numbered according to the EU index as in Kabat, wherein the modified IgG has an increased half-life compared to the half-life of an IgG having the wild-type non-human IgG constant domain, and wherein at least one of the amino acid substitutions is at amino acid residue 252, 254, 256, 309, 311, 433 or 434, and an amino acid substitution at amino acid residue 252 is a substitution with tyrosine, phenylalanine, tryptophan or threonine, an amino acid substitution at amino acid residue 254 is a substitution with threonine, an amino acid substitution at amino acid residue 256 is a substitution with serine, arginine, glutamine, glutamic acid, aspartic acid, alanine, asparagine or threonine, an amino acid substitution at amino acid residue 309 is a substitution with proline, an amino acid substitution at amino acid residue 311 is a substitution with serine, an amino acid substitution at amino acid residue 433 is a substitution with arginine, serine, isoleucine, proline, or glutamine, and an amino acid substitution at amino acid residue 434 is a substitution with histidine, phenylalanine, or tyrosine.

5. The modified IgG of claim 1, 2, 3, or 4 which has a higher affinity for FcRn than the IgG having the wild-type constant domain.

6. The modified IgG of claim 1, wherein an amino acid substitution at amino acid residue 385 is a substitution with arginine, aspartic acid, serine, threonine, histidine, lysine, alanine or glycine, an amino acid substitution at amino acid residue 386 is a substitution with threonine, proline, aspartic acid, serine, lysine, arginine, isoleucine, or methionine, an amino acid substitution at amino acid residue 387 is a substitution with arginine, proline, histidine, serine, threonine, or alanine, and an amino acid substitution at amino acid residue 389 is a substitution with proline, serine or asparagine.

7. The modified IgG of claim 4, wherein an amino acid substitution at amino acid residue 385 is a substitution with arginine, aspartic acid, serine, threonine, histidine, lysine, alanine or glycine, an amino acid substitution at amino acid residue 386 is a substitution with threonine, proline, aspartic acid, serine, lysine, arginine, isoleucine, or methionine, an amino acid substitution at amino acid residue 387 is a substitution with arginine, proline, histidine, serine, threonine, or alanine, and an amino acid substitution at amino acid residue 389 is a substitution with proline, serine or asparagine.

8. The modified IgG of claim 1, 2, 3 or 6 which is a human or humanized IgG.

9. The modified IgG of claim 8 which is $IgG_1$, $IgG_2$, $IgG_3$ or $IgG_4$.

10. The modified IgG of claim 4 or 7 which is a non-human IgG.

11. The modified IgG of claim 10 which is $IgG_1$, $IgG_{2a}$, $IgG_{2b}$, $IgG_{2c}$ or $IgG_3$.

12. The modified IgG of claim 1, wherein the IgG constant domain is an $IgG_1$ constant domain.

13. The modified IgG of claim 2, 3 or 6, wherein the IgG constant domain is an $IgG_1$ constant domain.

14. The modified IgG of claim 1, 2, 3 or 6, wherein the IgG constant domain is an $IgG_1$, $IgG_2$, $IgG_3$ or $IgG_4$ constant domain.

15. The modified IgG of claim 12, wherein an amino acid substitution at amino acid residue 252 is a substitution with tyrosine, phenylalanine, tryptophan or threonine, an amino acid substitution at amino acid residue 254 is a substitution with threonine, an amino acid substitution at amino acid residue 256 is a substitution with serine, arginine, glutamine, glutamic acid, or aspartic acid, an amino acid substitution at amino acid residue 309 is a substitution with proline, an amino acid substitution at amino acid residue 311 is a substitution with serine, an amino acid substitution at amino acid residue 433 is a substitution with arginine, serine, isoleucine, proline or glutamine, and an amino acid substitution at amino acid residue 434 is a substitution with histidine, phenylalanine, or tyrosine.

16. The modified IgG of claim 15, wherein an amino acid substitution at amino acid residue 385 is a substitution with arginine, aspartic acid, serine, threonine, histidine, lysine or alanine, an amino acid substitution at amino acid residue 386 is a substitution with threonine, proline, aspartic acid, serine, lysine, arginine, isoleucine, or methionine, an amino acid substitution at amino acid residue 387 is a substitution with arginine, histidine, serine, threonine, or alanine, and an amino acid substitution at amino acid residue 389 is a substitution with proline or serine.

17. The modified IgG of claim 10 which is a rodent, donkey, sheep, rabbit, goat, guinea pig, camel, horse or chicken IgG.

18. The modified IgG of claim 4, wherein the non-human IgG constant domain is a rodent, donkey, sheep, rabbit, goat, guinea pig, camel, horse or chicken IgG constant domain.

19. The modified IgG of claim 1, 2, 3, 4, 6, 7, 15 or 16 which inimunospecifically binds to an RSV antigen.

20. The modified IgG of claim 1, 2, 3, 6, 15 or 16 which comprises the heavy chain variable domain and light chain variable domain of palivizumab (SEQ ID NOS.: 7 and 8).

21. The modified IgG of claim 1, 2, 3, 6, 15 or 16 which comprises the heavy chain variable domain and light chain variable domain of A4B4L1FR-S28R (SEQ ID NOS.:48 and 11).

22. A pharmaceutical composition comprising the modified IgG of claim 1, 2, 3, 4, 6, 7, 15 or 16 and a pharmaceutically acceptable carrier.

23. A pharmaceutical composition comprising the modified IgG of claim 19 and a pharmaceutically acceptable carrier.

24. A pharmaceutical composition comprising the modified IgG of claim 20 and a pharmaceutically acceptable carrier.

25. A pharmaceutical composition comprising the modified IgG of claim 21 and a pharmaceutically acceptable carrier.

26. A kit comprising the modified IgG of claim 1, 2, 2, 4, 6, 7, 15 or 16, in a container, and instructions for use.

27. A kit comprising the modified IgG of claim 19, in a container, and instructions for use.

28. A kit comprising the modified IgG of claim 20, in a container, and instructions for use.

29. A kit comprising the modified IgG of claim 21, in a container, and instructions for use.

30. The modified IgG of claim 1, 2, 3, 6, 15 or 16 which comprises the variable heavy (VH) complementarily determining region (CDR)1, VH CDR2, VH CDR3, variable light (VL) CDR1, VL CDR2 and VL CDR3 of palivizumab (SEQ ID NOS.: 1–6, respectively).

31. The modified IgG of claim 1, 2, 3, 6, 15 or 16 which comprises the VH CDR1, VH CDR2, VH CDR3, VL CDR1, VL CDR2 and VL CDR3 of A4B4L1FR-S28R (SEQ ID NOS.: 10, 19, 20, 39, 5, and 6, respectively).

* * * * *

UNITED STATES PATENT AND TRADEMARK OFFICE
CERTIFICATE OF CORRECTION

| | | |
|---|---|---|
| PATENT NO. | : 7,083,784 B2 | Page 1 of 1 |
| APPLICATION NO. | : 10/020354 | |
| DATED | : August 1, 2006 | |
| INVENTOR(S) | : William Dall'Acqua, Leslie S. Johnson and Elizabeth Sally Ward | |

It is certified that error appears in the above-identified patent and that said Letters Patent is hereby corrected as shown below:

On the title page, please correct the assignee to read as follows:

(73) Assignee: MedImmune, Inc., Gaithersburg, MD (US); Board of Regents, The University of Texas System, Austin, TX (US).

Col. 133, line 14, please amend Claim 19 to read as follows:

19. The modified IgG of claim 1, 2, 3, 4, 5, 6, 7, 15 or 16 which immunospecifically binds to an RSV antigen.

Signed and Sealed this

Eighth Day of January, 2008

JON W. DUDAS
*Director of the United States Patent and Trademark Office*

UNITED STATES PATENT AND TRADEMARK OFFICE
CERTIFICATE OF CORRECTION

PATENT NO. : 7,083,784 B2
APPLICATION NO. : 10/020354
DATED : August 1, 2006
INVENTOR(S) : Dall'Acqua et al.

It is certified that error appears in the above-identified patent and that said Letters Patent is hereby corrected as shown below:

Column 1, lines 9-12, please revise as follows:

Delete: "This invention was made, in part, with United States Government support under award number AI39167 from the National Institute of Health. The United States Government may have certain rights in the invention."

And Insert: --This invention was made with government support under Grant Number AI39167 awarded by the National Institute of Health. The government has certain rights in the invention.--

Signed and Sealed this

Ninth Day of November, 2010

David J. Kappos
*Director of the United States Patent and Trademark Office*